United States Patent
Sivakumar et al.

(10) Patent No.: US 8,563,596 B2
(45) Date of Patent: Oct. 22, 2013

(54) ENANTIOMERICALLY PURE COMPOUNDS FOR THE TREATMENT OF PROLIFERATIVE DISORDERS

(75) Inventors: Meenakshi Sivakumar, Maharashtra (IN); Malcolm Mascarenhas, Maharashtra (IN); Ankush Sarde, Maharashtra (IN); Pramod Kumar Jadhav, Maharashtra (IN); Manoj Shukla, Maharastra (IN); Kalpana Joshi, Maharashtra (IN); Maggie Rathos, Maharashtra (IN)

(73) Assignee: Piramal Enterprises Limited, Mumbai (IN)

( * ) Notice: Subject to any disclaimer, the term of this patent is extended or adjusted under 35 U.S.C. 154(b) by 803 days.

(21) Appl. No.: 12/305,815

(22) PCT Filed: Jun. 21, 2006

(86) PCT No.: PCT/IB2006/052002
§ 371 (c)(1),
(2), (4) Date: Dec. 19, 2008

(87) PCT Pub. No.: WO2007/148158
PCT Pub. Date: Dec. 27, 2007

(65) Prior Publication Data
US 2010/0179210 A1  Jul. 15, 2010

(51) Int. Cl.
| A01N 43/36 | (2006.01) |
| A61K 31/40 | (2006.01) |
| C07D 405/00 | (2006.01) |
| C07D 409/00 | (2006.01) |
| C07D 411/00 | (2006.01) |
| C07D 207/00 | (2006.01) |

(52) U.S. Cl.
USPC .................. 514/422; 548/525; 548/532

(58) Field of Classification Search
USPC .................. 514/422; 548/525, 532
See application file for complete search history.

(56) References Cited

U.S. PATENT DOCUMENTS

2004/0106581 A1* 6/2004 Lal et al. .................. 514/100

OTHER PUBLICATIONS

Vippagunta et al. Advanced Drug Delivery Reviews, 2001, vol. 48, pp. 3-26.*

\* cited by examiner

*Primary Examiner* — Samira Jean-Louis
(74) *Attorney, Agent, or Firm* — Frommer Lawrence & Haug LLP

(57) ABSTRACT

The present invention relates to an enantiomerically pure (+)-trans enantiomer of a compound represented by the following formula (I):

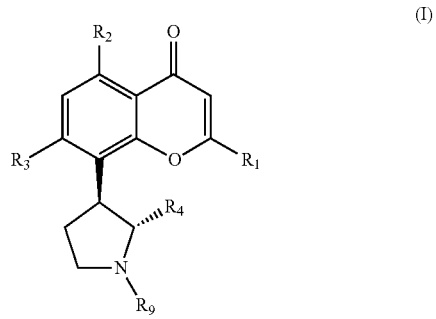

wherein $R_1$, $R_2$, $R_3$, $R_4$ and $R_9$ are as defined in the specification; enantiomerically pure intermediates thereof, to processes for the preparation of the enantiomerically pure compound and its intermediates, and to a pharmaceutical composition comprising the enantiomerically pure compound. The compound of formula (I) is useful for the treatment of diseases or disorders mediated by the inhibition of cyclin dependant kinase, such as cancer.

9 Claims, 3 Drawing Sheets

ENANTIOMERICALLY PURE COMPOUNDS FOR THE TREATMENT OF PROLIFERATIVE DISORDERS

FIELD OF INVENTION

The present invention relates to enantiomerically pure (+)-trans enantiomer of pyrrolidines substituted with flavones represented by formula (I), enantiomerically pure intermediates thereof, processes for their respective preparation, their use as active ingredients in pharmaceuticals, particularly for the treatment of proliferative disorders such as cancer, and pharmaceutical compositions comprising them.

BACKGROUND OF INVENTION

Regulators of the cell cycle have gained widespread importance in proliferative diseases. Cyclin-dependent kinases (CDKs) are a family of enzymes which become activated in specific phases of the cell cycle.

A wide variety of diseases are characterized by uncontrolled cell proliferation that results from some fault in the regulatory pathways in the cell cycle [e.g. overexpression of cyclins or deletions of genes encoding CKIs (CDK inhibitory proteins)]. The overexpression of cyclinD1 leads to the deregulation of CDK4-D1 kinase activity and thereby contributes to uncontrolled cell proliferation. With knowledge of the role of CDKs in cell cycle regulation and the discovery that approximately 90% of all neoplasias are associated with CDK hyperactivation leading to the inactivation of the Rb pathway, CDKs are attractive targets for the development of anti-tumor drugs.

The prominent role of CDK/cyclin kinase complexes, in particular CDK4/cyclin D1 kinase complexes, in the induction of cell proliferation and their deregulation in tumors, makes them ideal targets for developing highly specific anti-proliferative agents.

Flavopiridol and its analogs are well known as effective CDK inhibitors and offer a potential approach to anti-proliferative therapy.

The applicant's co-pending published US Patent application no. 2004/0106581 describes novel compounds useful in inhibiting CDKs and having good selectivity and cytotoxicity against various proliferative cell lines. This patent application is incorporated herein by reference in its entirety. The novel compounds disclosed in the aforesaid patent application, have two chiral centers and hence, can exist as four enantiomers i.e. (+)-trans, (−)-trans, (+)-cis and (−)-cis.

It is well known in the art that the enantiomers of a given chemical compound, despite sharing identical chemical composition, can have very different actions when placed in biological systems. It is often the case that one enantiomer provide the beneficial effects while the opposite enantiomer may be deleterious or inert. Thus, advantages associated with the administration of the racemic mixture may be retained by using a single enantiomer of the compound without associated adverse side effects.

The studies specifically establish that the CDK inhibitory activity and the anti-proliferative activity is due to the (+)-trans enantiomer of pyrrolidines substituted with flavones represented by formula (I) rather than the (−)-trans enantiomer.

It would be desirable for the (+)-trans enantiomer of pyrrolidines substituted with flavones, the compounds of formula (I), to be available in a form substantially free of its (−)-trans enantiomer to provide a safe and an effective method for the treatment of diseases or disorders mediated by inhibition of cyclin dependant kinases (CDKs) and also for the treatment of diseases associated with excessive cell proliferation such as cancer.

In view of this finding, the present inventors have developed a new process for the preparation of an enantiomerically pure (+)-trans enantiomer of pyrrolidines substituted with flavones represented by formula (I).

SUMMARY OF INVENTION

The present invention relates to an enantiomerically pure (+)-trans enantiomer of pyrrolidines substituted with flavones represented by the following formula (I) (herein after referred to as compounds of formula (I)) and to a metabolite, prodrug, pharmaceutically acceptable salt, pharmaceutically acceptable solvate or polymorph thereof:

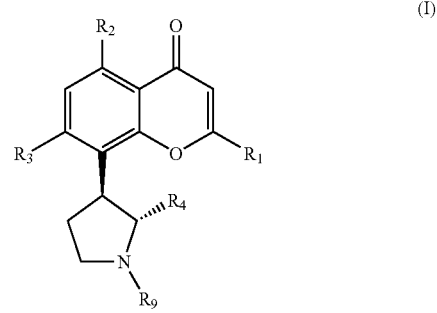

wherein the definitions of $R_1$, $R_2$, $R_3$, $R_4$ and $R_9$ are provided hereinafter in the detailed description.

This invention also relates to a process for the preparation of the enantiomerically pure compound of formula (I), or a metabolite, prodrug, pharmaceutically acceptable salt or pharmaceutically acceptable solvate thereof. The process produces the (+)-trans enantiomer with high chemical and enantiomeric purity and in high yield.

This invention also relates to intermediates used in the process for the preparation of the enantiomerically pure compound of formula (I).

This invention further relates to a process for the resolution of a compound of formula (VIA) and its derivatives, which compound is a key intermediate for the preparation of the enantiomerically pure compound of formula (I).

This invention still further relates to a pharmaceutical composition for the treatment of a disease or a disorder in a mammal, mediated by inhibition of CDKs, comprising a therapeutically effective amount of the enantiomerically pure compound of formula (I) or a salt, solvate or prodrug thereof, as the active ingredient, and a pharmaceutically acceptable carrier.

This invention still further relates to a pharmaceutical composition for the treatment of a disease or a disorder in a mammal, associated with excessive cell proliferation, comprising a therapeutically effective amount of the enantiomerically pure compound of formula (I) or a salt, solvate or prodrug thereof as the active ingredient, and a pharmaceutically acceptable carrier.

This invention still further relates to a method for the treatment of a disease or a disorder mediated by inhibition of CDK to a mammal in need thereof, comprising administering to said mammal an effective amount of the enantiomerically pure (+)-trans enantiomer of a compound of formula (I) or a metabolite, prodrug, pharmaceutically acceptable salt, pharmaceutically acceptable solvate or polymorph thereof.

This invention still further relates to a method for the treatment of a disease or a disorder in a mammal, associated with excessive cell proliferation, comprising a therapeutically effective amount of the enantiomerically pure compound of formula (I) or a salt, solvate, or prodrug thereof as the active ingredient, and a pharmaceutically acceptable carrier.

DETAILED DESCRIPTION OF THE INVENTION

Figure 1:
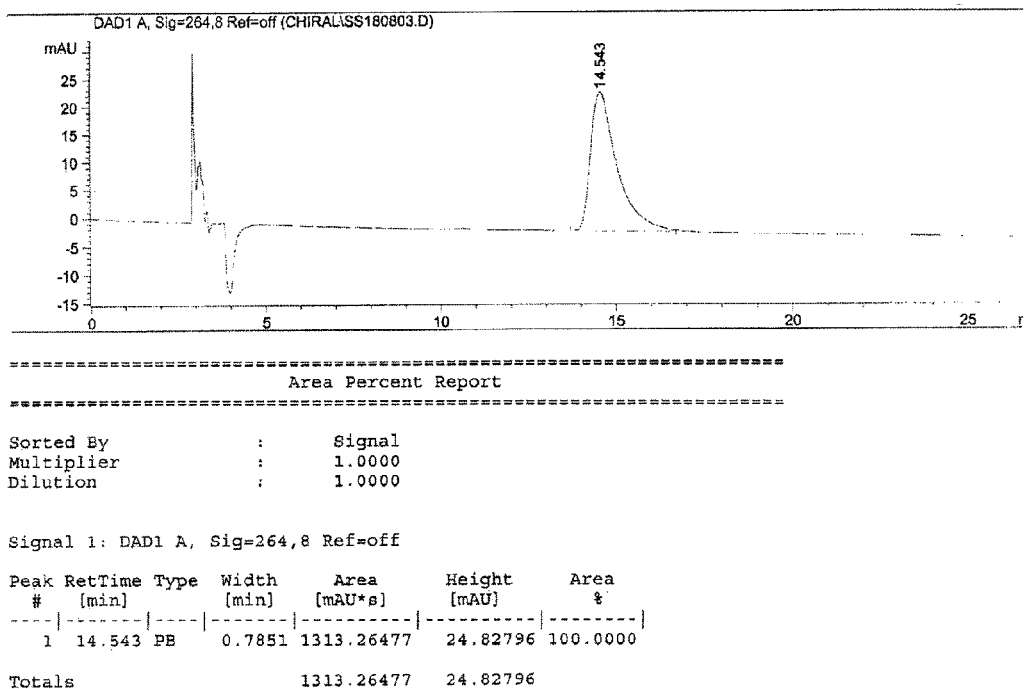
FIG. 1: Chiral HPLC (Chiralcel OD-H (250×4.6 mm) Column) of (−)-trans-[1-methyl-3-(2,4,6-trimethoxyphenyl)-pyrrolidin-2-yl]-methanol obtained as described in Example 5.

The compounds of formula (I) of the present invention are useful in inhibiting CDKs, particularly CDK4/cyclinD1 complexes and find use in anti-proliferative therapies for diseases characterized by excessive cell growth such as cancers, cardiovascular abnormalities, inflammation and arthritis, nephrological disorders, parasitology, psoriasis, Alzheimer's disease, immunological disorders involving unwanted proliferation of leukocytes, restenosis and other proliferative smooth muscle disorders, viral infections, and mycotic infections.

The present invention is specifically directed to an enantiomerically pure compound of formula (I) and to a metabolite, prodrug, pharmaceutically acceptable salt, pharmaceutically acceptable solvate or polymorph thereof. As is mentioned hereinbefore the compounds disclosed in the applicant's co-pending published US Patent application no. 2004/0106581 have two chiral centers and hence, can exist as four enantiomers namely (+)-trans, (−)-trans, (+)-cis and (−)-cis. More particularly, the present invention relates to an enantiomerically pure (+)-trans enantiomer of pyrrolidines substituted with flavones represented herein by formula (I).

The efficacy of the racemic compound disclosed in the published US Patent application no. 2004/0106581 and its separate enantiomers have been extensively studied by the present inventors. It has been observed that only the (+)-trans enantiomer is active. The present invention has made the provision of an enantiomerically pure (+)-trans enantiomer represented herein by formula (I) possible thereby enabling a possible reduction in the required dose of the drug and its side effects.

Listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

The terms "flavone" or "chromone" or their analogs mean compounds that can be represented by the following basic structure:

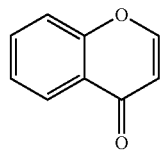

As used herein, the term "alkyl" refers to the radical of saturated aliphatic groups, including straight-chain alkyl groups and branched-chain alkyl groups. Furthermore, unless stated otherwise, the term "alkyl" includes unsubstituted alkyl groups as well as alkyl groups, which are substituted by one or more different substituents.

Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or tert-butyl.

The terms "alkoxy" as used herein refers to an alkyl group, as defined above, having an oxygen radical attached thereto. Representative alkoxyl groups include methoxy, ethoxy, propoxy, t-butoxy and the like.

The terms "alkenyl" refer to unsaturated aliphatic groups analogous in length and possible substitution to the alkyls described above, but that contain at least one double, for example 1, 2 or 3 double bonds, provided that the double bonds are not located within a cyclic alkyl group in such a manner that an aromatic system results. Examples of alkenyl groups include vinyl, 1-propenyl, 2-propenyl, 2-butenyl, 2-methyl-1-propenyl or 3-methyl-2-butenyl. Furthermore, unless otherwise stated, the terms "alkenyl" include unsubstituted and substituted alkenyl groups.

The term "aryl" as used herein refers to monocyclic or polycyclic hydrocarbon groups having up to 14 ring carbon atoms in which at least one carbocyclic ring is present that has a conjugated pi electron system. Examples of $(C_6-C_{14})$-aryl residues are phenyl, naphthyl, biphenyl, fluorenyl or anthracenyl. Examples of $(C_6-C_{10})$-aryl residues are phenyl or naphthyl. Unless stated otherwise, and irrespective of any specific substituents bonded to aryl groups which are indicated in the definition of the compounds of formula (I), aryl residues, for example phenyl, naphthyl or fluorenyl, can in general be unsubstituted or substituted by one or more, for example 1, 2, 3, 4 or 5, identical or different substituents. Unless stated otherwise, substituents that can be present in substituted aryl groups are: halogen, alkyl, alkenyl, alkynyl, fluoromethyl, difluoromethyl, trifluoromethyl, hydroxyl, aryloxy, amino, cyano, nitro, thiol, imine, amide or carbonyl (such as carboxyl, formate, carbamide, an ester, ketone or aldehyde), sulfhydryl, silyl ether, thiocarbonyl (such as thioester, thioacetate or thioformate), sulfonyl, aminoacid ester, or a heterocycle which is saturated, partially unsaturated or aromatic. Aryl residues can be bonded via any desired position, and in substituted aryl residues the substituents can be located in any desired position.

The term "heterocycle" refers to a saturated, partially unsaturated or aromatic ring containing five or six ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, nitro, cyano, $SR_7$, $C_1$-$C_4$-alkyl, fluoromethyl, difluoromethyl, trifluoromethyl, $C_1$-$C_4$-alkoxy, hydroxyl, carboxy, $C_1$-$C_4$- alkoxycarbonyl, C$_1$-C$_4$-alkylenehydroxyl, CONH$_2$, CONR$_5$R$_6$, SO$_2$NR$_5$R$_6$, cycloalkyl, NR$_5$R$_6$.

The term "heteroatom" as used herein means an atom of any element other than carbon or hydrogen. Preferred heteroatoms are nitrogen, oxygen, sulfur and phosphorous.

Halogen is fluorine, chlorine, bromine or iodine, preferably fluorine, chlorine or bromine.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

It should be noted that any heteroatom with unsatisfied valences is assumed to have the hydrogen atom to satisfy the valences.

The term "racemic" or "racemate", and other like terms refer to generally equimolar proportions of a (+)-enantiomer and a (−)-enantiomer of a compound in a composition.

The term "enantiomerically pure" refers to a compound or compounds that is or are present in enantiomeric excess of greater than 95%. Preferably, the enantiomeric excess is greater than 97%. More preferably, the enantiomeric excess is greater than 99%.

The term "enantiomeric excess" refers to a difference between the amount of one enantiomer and the amount of the other enantiomer that is present in the product mixture. Thus for example, enantiomeric excess of 96% refers to a product mixture having 98% of one enantiomer and 2% of the other enantiomer.

The term "substantially free" means that the amount of the (+)-trans enantiomer predominates the composition relative to the (−)-trans enantiomer of the compound of formula (I). More specifically, this means that the amount of the (+)-trans enantiomer relative to the (−)-trans enantiomer by weight is at least about 95%, more preferably greater than 97%.

As used herein, the term "prodrugs" refers to compound forms which are transformed in vivo to the parent compound according to the invention, for example, by hydrolysis in blood. Thus, prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Such metabolically cleavable groups form a class well known to practitioners of the art.

The term "pharmaceutically acceptable salt(s)", as used herein, unless otherwise indicated, includes salts of basic or acidic groups of the compound of the invention, which groups are capable of forming salts. In case the compounds according to formula (I) contain one or more acidic or basic groups, the invention also comprises their corresponding pharmaceutically or toxicologically acceptable salts. Compounds of formula (I) which contain one or more basic groups, i.e. groups which can be protonated and can be used according to the invention in the form of their addition salts with non-toxic inorganic or organic acids. Examples of suitable inorganic acids include: boric acid, perchloric acid, hydrochloric acid, hydrobromic acid, sulfuric acid, sulfamic acid, phosphoric acid, nitric acid and other inorganic acids known to the person skilled in the art. Examples of suitable organic acids include: acetic acid, propionic acid, succinic acid, glycolic acid, gluconic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, ketoglutaric acid, benzenesulfonic acid, glycerophosphoric acid and other organic acids known to the person skilled in the art. The compounds of formula (I) which contain acidic groups can be used according to the invention, for example, as alkali metal salts like lithium (Li), sodium (Na), and potassium (K) salts. The pharmaceutically acceptable salts of the present invention can be synthesized from the subject compound which contains a basic or acidic moiety by conventional chemical methods. Generally the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, THF, dioxane or mixtures of these solvents.

The present invention furthermore includes all solvates of compounds of formula (I), for example hydrates or adducts with alcohols and also derivatives and prodrugs of the compounds of formula (I) which contain physiologically tolerable and cleavable groups, for example esters and amides.

Various polymorphs of compounds of formula (I) forming part of this invention may be prepared by crystallization of compounds of formula (I) under different conditions. For example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

Where the stereochemistry is depicted in the structures it represents a relative rather than an absolute configuration.

The present invention relates to an enantiomerically pure compound of formula (I), to a metabolite, prodrug, pharmaceutically acceptable salt, pharmaceutically acceptable solvate or polymorph thereof.

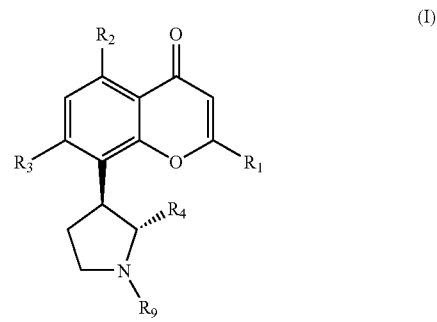

(I)

wherein,

R$_1$ is phenyl, which is unsubstituted or substituted by 1, 2, or 3 identical or different substituents selected from: halogen, nitro, cyano, fluoromethyl, difluoromethyl, trifluoromethyl, C$_1$-C$_4$-alkoxy, hydroxyl, carboxy, C$_1$-C$_4$-alkoxycarbonyl, C$_1$-C$_4$-alkylenehydroxyl, CONH$_2$, CONR$_5$R$_6$, SO$_2$NR$_5$R$_6$, cycloalkyl, NR$_5$R$_6$, SR$_7$; or is a heterocycle, which is a saturated, partially unsaturated or aromatic ring containing five or six ring atoms of which 1, 2 or 3 are identical or different heteroatoms selected from: nitrogen, oxygen and sulfur, and where the heterocycle is unsubstituted or substituted by 1, 2, or 3 identical or different substituents selected from: halogen, nitro, cyano, $C_1$-$C_4$-alkyl, fluoromethyl, difluoromethyl, trifluoromethyl, $C_1$-$C_4$-alkoxy, hydroxyl, carboxy, $C_1$-$C_4$-alkoxycarbonyl, $C_1$-$C_4$-alkylenehydroxyl, $CONH_2$, $CONR_5R_6$, $SO_2NR_5R_6$, cycloalkyl, $NR_5R_6$ and $SR_7$;

wherein $R_5$ and $R_6$ are each independently selected from: hydrogen, $C_1$-$C_4$-alkyl, $C_1$-$C_4$-alkoxycarbonyl, $C_1$-$C_4$-alkylcarbonyl, aryl; or $R_5$ and $R_6$ together with the nitrogen atom to which they are bonded may form a five or six membered ring which may optionally contain an additional heteroatom; and $R_7$ may be selected from hydrogen, $C_1$-$C_4$-alkyl, aryl, $SR_{10}$ wherein $R_{10}$ may be selected from $C_1$-$C_4$-alkyl or aryl;

$R_2$ and $R_3$ are each independently selected from: halogen, hydroxyl and $OR_8$;

wherein $R_8$ is substituted or unsubstituted $C_1$-$C_{10}$-alkyl, $C_1$-$C_4$-alkanoyl, substituted or unsubstituted aroyl;

$R_4$ is $C_1$-$C_4$-alkylenehydroxyl; and $R_9$ is hydrogen or $C_1$-$C_4$-alkyl.

In alternative preferred embodiments of the enantiomerically pure compounds of formula (I), the groups $R_1$-$R_3$ and $R_9$, independently from each other, have the preferred meanings given below:

$R_1$ is phenyl, which is unsubstituted or substituted by 1, 2, or 3 identical or different substituents selected from: halogen, nitro, cyano, $C_1$-$C_4$-alkyl, fluoromethyl, difluoromethyl, trifluoromethyl, $C_1$-$C_4$-alkoxy, hydroxyl, carboxy, $C_1$-$C_4$-alkoxycarbonyl, $C_1$-$C_4$-alkylenehydroxyl, $CONH_2$, $CONR_8R_8$, $SO_2NR_5R_6$, cycloalkyl, $NR_5R_6$ and $SR_7$;

$R_2$ and $R_3$ are $OR_8$, where $R_8$ is as defined and is the same or different for $R_2$ and $R_3$;

$R_9$ is $C_1$-$C_4$-alkyl;

or a metabolite, prodrug, pharmaceutically acceptable salt, pharmaceutically acceptable solvate or polymorph of the preferred embodiments.

According to present invention, the most preferred enantiomerically pure compound of formula (I), or a salt or prodrug thereof, is selected from:

(+)-trans-2-(2-Chlorophenyl)-8-(2-hydroxymethyl-1-methyl-pyrrolidin-3-yl)-5,7-dimethoxy-chromen-4-one;

(+)-trans-2-(2-Chlorophenyl)-5,7-dihydroxy-8-(2-hydroxymethyl-1-methyl-pyrrolidin-3-yl)-chromen-4-one;

(+)-trans-2-(2-Chlorophenyl)-5,7-dihydroxy-8-(2-hydroxymethyl-1-methyl-pyrrolidin-3-yl)-chromen-4-one hydrochloride;

(+)-trans-2-(2-Chloro-5-fluorophenyl)-8-(2-hydroxymethyl-1-methyl-pyrrolidin-3-yl)-5,7-dimethoxy-chromen-4-one, (+)-trans-2-(2-Chloro-5-fluorophenyl)-5,7-dihydroxy-8-(2-hydroxymethyl-1-methyl-pyrrolidin-3-yl)-chromen-4-one;

(+)-trans-2-(2-Chloro-5-fluorophenyl)-5,7-dihydroxy-8-(2-hydroxymethyl-1-methyl-pyrrolidin-3-yl)-chromen-4-one hydrochloride;

(+)-trans-2-(2-Bromo-5-fluorophenyl)-8-(2-hydroxymethyl-1-methyl-pyrrolidin-3-yl)-5,7-dimethoxy-chromen-4-one;

(+)-trans-2-(2-Bromo-5-fluorophenyl)-5,7-dihydroxy-8-(2-hydroxymethyl-1-methyl-pyrrolidin-3-yl)-chromen-4-one;

(+)-trans-2-(2-Bromo-5-fluorophenyl)-5,7-dihydroxy-8-(2-hydroxymethyl-1-methyl-pyrrolidin-3-yl)-chromen-4-one hydrochloride;

(+)-trans-2-(2-Bromo-5-fluorophenyl)-5,7-dihydroxy-8-(2-hydroxymethyl-1-methyl-pyrrolidin-3-yl)-chromen-4-one methane sulfonate;

(+)-trans-2-(2,4-Dichloro-5-fluorophenyl)-8-(2-hydroxymethyl-1-methyl-pyrrolidin-3-yl)-5,7-dimethoxy-chromen-4-one;

(+)-trans-2-(2,4-Dichloro-5-fluorophenyl)-5,7-dihydroxy-8-(2-hydroxymethyl-1-methyl-pyrrolidin-3-yl)-chromen-4-one;

(+)-trans-2-(2,4-Dichloro-5-fluorophenyl)-5,7-dihydroxy-8-(2-hydroxymethyl-1-methyl-pyrrolidin-3-yl)-chromen-4-one hydrochloride (+)-trans-2-(2,4-Dichloro-5-fluorophenyl)-5,7-dihydroxy-8-(2-hydroxymethyl-1-methyl-pyrrolidin-3-yl)-chromen-4-one methane sulfonate;

(+)-trans-2-(2,4-Dichloro-5-fluorophenyl)-5,7-dihydroxy-8-(2-hydroxymethyl-1-methyl-pyrrolidin-3-yl)-chromen-4-one citrate;

(+)-trans-2-(2,4-Dichloro-5-fluorophenyl)-5,7-dihydroxy-8-(2-hydroxymethyl-1-methyl-pyrrolidin-3-yl)-chromen-4-one tartrate;

(+)-trans-2-(2,4-Dichloro-5-fluorophenyl)-5,7-dihydroxy-8-(2-hydroxymethyl-1-methyl-pyrrolidin-3-yl)-chromen-4-one maleate;

(+)-trans-2-(2,4-Dichloro-5-fluorophenyl)-5,7-dihydroxy-8-(2-hydroxymethyl-1-methyl-pyrrolidin-3-yl)-chromen-4-one acetate;

(+)-trans-2-(2,4-Dichloro-5-fluorophenyl)-5,7-dihydroxy-8-(2-hydroxymethyl-1-methyl-pyrrolidin-3-yl)-chromen-4-one sulfate;

(+)-trans-2-(2,4-Dichloro-5-fluorophenyl)-5,7-dihydroxy-8-(2-hydroxymethyl-1-methyl-pyrrolidin-3-yl)-chromen-4-one nitrate;

(+)-trans-2-(2,4-Dichlorophenyl)-8-(2-hydroxymethyl-1-methyl-pyrrolidin-3-yl)-5,7-dimethoxy-chromen-4-one;

(+)-trans-2-(2,4-Dichlorophenyl)-5,7-dihydroxy-8-(2-hydroxymethyl-1-methyl-pyrrolidin-3-yl)-chromen-4-one;

(+)-trans-2-(2,4-Dichlorophenyl)-5,7-dihydroxy-8-(2-hydroxymethyl-1-methyl-pyrrolidin-3-yl)-chromen-4-one hydrochloride;

(+)-trans-2-(4-Bromo-2-chlorophenyl)-8-(2-hydroxymethyl-1-methyl-pyrrolidin-3-yl)-5,7-dimethoxy-chromen-4-one;

(+)-trans-2-(4-Bromo-2-chlorophenyl)-5,7-dihydroxy-8-(2-hydroxymethyl-1-methyl-pyrrolidin-3-yl)-chromen-4-one;

(+)-trans-2-(4-Bromo-2-chlorophenyl)-5,7-dihydroxy-8-(2-hydroxymethyl-1-methyl-pyrrolidin-3-yl)-chromen-4-one hydrochloride;

(+)-trans-2-(2-Chloro-4-cyanophenyl)-8-(2-hydroxymethyl-1-methyl-pyrrolidin-3-yl)-5,7-dimethoxy-chromen-4-one;

(+)-trans-2-(2-Chloro-4-cyanophenyl)-8-(2-hydroxymethyl-1-methyl-pyrrolidin-3-yl)-5,7-dimethoxy-chromen-4-one hydrochloride;

(+)-trans-2-(2-Chloro-4-cyanophenyl)-5,7-dihydroxy-8-(2-hydroxymethyl-1-methyl-pyrrolidin-3-yl)-chromen-4-one;

(+)-trans-2-(2-Chloro-4-cyanophenyl)-5,7-dihydroxy-8-(2-hydroxymethyl-1-methyl-pyrrolidin-3-yl)-chromen-4-one hydrochloride;

(+)-trans-2-(2-Chloro-4-trifluoromethylphenyl)-8-(2-hydroxymethyl-1-methyl-pyrrolidin-3-yl)-5,7-dimethoxy-chromen-4-one;

(+)-trans-2-(2-Chloro-4-trifluoromethylphenyl)-5,7-dihydroxy-8-(2-hydroxymethyl-1-methyl-pyrrolidin-3-yl)-chromen-4-one;

(+)-trans-2-(2-Chloro-4-trifluoromethylphenyl)-5,7-dihydroxy-8-(2-hydroxymethyl-1-methylpyrrolidin-3-yl)-chromen-4-one hydrochloride;

(+)-trans-2-(2-Chloro-4-nitrophenyl)-8-(2-hydroxymethyl-1-methyl-pyrrolidin-3-yl)-5,7-dimethoxy-chromen-4-one;

(+)-trans-2-(2-Chloro-4-nitrophenyl)-8-(2-hydroxymethyl-1-methyl-pyrrolidin-3-yl)-5,7-dimethoxy-chromen-4-one hydrochloride;

(+)-trans-2-(2-Chloro-4-nitrophenyl)-8-(2-hydroxymethyl-1-methyl-pyrrolidin-3-yl)-5,7-dimethoxy-chromen-4-one gluconate;

(+)-trans-2-(2-Chloro-4-nitrophenyl)-5,7-dihydroxy-8-(2-hydroxymethyl-1-methyl-pyrrolidin-3-yl)-chromen-4-one;

(+)-trans-2-(2-Chloro-4-nitrophenyl)-5,7-dihydroxy-8-(2-hydroxymethyl-1-methyl-pyrrolidin-3-yl)-chromen-4-one hydrochloride;

(+)-trans-2-(4-Amino-2-chlorophenyl)-8-(2-hydroxymethyl-1-methyl-pyrrolidin-3-yl)-5,7-dimethoxy-chromen-4-one;

(+)-trans-2-(4-Amino-2-chlorophenyl)-5,7-dihydroxy-8-(2-hydroxymethyl-1-methyl-pyrrolidin-3-yl)-chromen-4-one;

(+)-trans-2-(2-Chloro-4-methylaminophenyl)-5,7-dihydroxy-8-(2-hydroxymethyl-1-methyl-pyrrolidin-3-yl)-chromen-4-one;

(+)-trans-2-(4-Amino-2-chlorophenyl)-5,7-dihydroxy-8-(2-hydroxymethyl-1-methyl-pyrrolidin-3-yl)-chromen-4-one hydrochloride;

(+)-trans-2-(2-Chloro-4-methylaminophenyl)-5,7-dihydroxy-8-(2-hydroxymethyl-1-methyl-pyrrolidin-3-yl)-chromen-4-one hydrochloride;

(+)-trans-2-(2-Chloro-4-pyrrolidin-1-yl-phenyl)-8-(2-hydroxymethyl-1-methyl-pyrrolidin-3-yl)-5,7-dimethoxy-chromen-4-one;

(+)-trans-2-(2-Chloro-4-pyrrolidin-1-yl-phenyl)-5,7-dihydroxy-8-(2-hydroxy-methyl-1-methyl-pyrrolidin-3-yl)-chromen-4-one;

(+)-trans-2-(2-Chloro-4-pyrrolidin-1-yl-phenyl)-5,7-dihydroxy-8-(2-hydroxy-methyl-1-methyl-pyrrolidin-3-yl)-chromen-4-one hydrochloride;

(+)-trans-2-(2-Chloro-4-isopropylaminophenyl)-8-(2-hydroxymethyl-1-methyl-pyrrolidin-3-yl)-5,7-dimethoxy-chromen-4-one;

(+)-trans-2-(2-Chloro-4-isopropylaminophenyl)-5,7-dihydroxy-8-(2-hydroxy-methyl-1-methyl-pyrrolidin-3-yl)-chromen-4-one;

(+)-trans-2-(2-Chloro-4-isopropylaminophenyl)-5,7-dihydroxy-8-(2-hydroxy-methyl-1-methyl-pyrrolidin-3-yl)-chromen-4-one hydrochloride;

(+)-trans-2-(2,4-Dibromophenyl)-8-(2-hydroxymethyl-1-methyl-pyrrolidin-3-yl)-5,7-dimethoxy-chromen-4-one;

(+)-trans-2-(2,4-Dibromophenyl)-5,7-dihydroxy-8-(2-hydroxymethyl-1-methyl-pyrrolidin-3-yl)-chromen-4-one;

(+)-trans-2-(2,4-Dibromophenyl)-5,7-dihydroxy-8-(2-hydroxymethyl-1-methyl-pyrrolidin-3-yl)-chromen-4-one hydrochloride;

(+)-trans-2-(2-Bromo-4-chlorophenyl)-8-(2-hydroxymethyl-1-methyl-pyrrolidin-3-yl)-5,7-dimethoxy-chromen-4-one;

(+)-trans-2-(2-Bromo-4-chlorophenyl)-5,7-dihydroxy-8-(2-hydroxymethyl-1-methyl-pyrrolidin-3-yl)-chromen-4-one;

(+)-trans-2-(2-Bromo-4-chlorophenyl)-5,7-dihydroxy-8-(2-hydroxymethyl-1-methyl-pyrrolidin-3-yl)-chromen-4-one hydrochloride;

(+)-trans-2-(2-Chlorophenyl)-5-hydroxy-8-(2-hydroxymethyl-1-methyl-pyrrolidin-3-yl)-7-methoxy-chromen-4-one;

(+)-trans-2-(2-Chlorophenyl)-5-hydroxy-8-(2-hydroxymethyl-1-methyl-pyrrolidin-3-yl)-7-methoxy-chromen-4-one hydrochloride;

(+)-trans-2-(2-Chlorophenyl)-5-hydroxy-8-(2-hydroxymethyl-1-methyl-pyrrolidin-3-yl)-7-methoxy-chromen-4-one gluconate;

(+)-trans-2-(2-Chlorophenyl)-5-hydroxy-8-(2-hydroxymethyl)-1-methyl-pyrrolidin-3-yl)-7-(2-methoxy-ethoxymethoxy)-chromen-4-one;

(+)-trans-2-(2-Chlorophenyl)-5-hydroxy-8-(2-hydroxymethyl)-1-methyl-pyrrolidin-3-yl)-7-(2-methoxy-ethoxymethoxy)-chromen-4-one gluconate;

(+)-trans-2-(2-Chlorophenyl)-8-(2-hydroxymethyl-1-methyl-pyrrolidin-3-yl)-5,7-dimethoxy-chromen-4-one hydrochloride;

(+)-trans-2-(2-Chlorophenyl)-8-(2-hydroxymethyl-1-methyl-pyrrolidin-3-yl)-5,7-dimethoxy-chromen-4-one citrate;

(+)-trans-2-(2-Chlorophenyl)-8-(2-hydroxymethyl-1-methyl-pyrrolidin-3-yl)-5,7-dimethoxy-chromen-4-one tartarate;

(+)-trans-2-(2-Chlorophenyl)-8-(2-hydroxymethyl-1-methyl-pyrrolidin-3-yl)-5,7-dimethoxy-chromen-4-one glutamate;

(+)-trans-2-(2-Chloro-phenyl)-8-(2-hydroxymethyl-1-methyl-pyrrolidin-3-yl)-5,7-dimethoxy-chromen-4-one maleate;

(+)-trans-2-(2-Chlorophenyl)-8-(2-hydroxymethyl-1-methyl-pyrrolidin-3-yl)-5,7-dimethoxy-chromen-4-one nitrate;

(+)-trans-2-(2-Chlorophenyl)-8-(2-hydroxymethyl-1-methyl-pyrrolidin-3-yl)-5,7-dimethoxy-chromen-4-one acetate;

(+)-trans-2-(2-Chlorophenyl)-8-(2-hydroxymethyl-1-methyl-pyrrolidin-3-yl)-5,7-dimethoxy-chromen-4-one gluconate;

(+)-trans-Acetic acid 3-[2-(2-chlorophenyl)-5,7-dihydroxy-4-oxo-4H-chromen-8-yl]-1-methyl-pyrrolidin-2-yl methyl ester;

(+)-trans-Acetic acid 3-[2-(2-chlorophenyl)-5,7-dihydroxy-4-oxo-4H-chromen-8-yl]-1-methyl-pyrrolidin-2-yl methyl ester hydrochloride;

(+)-trans-Acetic acid 8-(2-acetoxymethylpyrrolidin-3-yl)-2-(2-chloro-phenyl)-5-hydroxy-4-oxo-4H-chromen-7-yl ester;

(+)-trans-Benzoic acid 8-(2-benzoyloxymethylpyrrolidin-3-yl)-2-(2-chloro phenyl)-5-hydroxy-4-oxo-4H-chromen-7-yl ester;

(+)-trans-Benzoic acid 8-(2-benzoyloxymethylpyrrolidin-3-yl)-2-(2-chloro phenyl)-5-hydroxy-4-oxo-4H-chromen-7-yl ester hydrochloride;

(+)-trans-Octanoic acid 2-(2-chlorophenyl)-5-hydroxy-8-(1-methyl-2-octanoyloxymethyl-pyrrolidin-3-yl)-4-oxo-4H-chromen-7-yl ester;

(+)-trans-Acetic acid 3-[2-(2-Chlorophenyl)-5-hydroxy-7-methoxy-4-oxo-4H-chromen-8-yl]-1-methyl-pyrrolidin-2-ylmethyl ester; and (+)-trans-Acetic acid 3-[2-(2-chlorophenyl)-5-hydroxy-7-(2-methoxy ethoxymethoxy)-4-oxo-4H-chromen-8-yl]-1-methyl-pyrrolidin-2-ylmethyl ester.

According to another embodiment of the present invention, a process for the preparation of an enantiomerically pure compound of formula (I) is provided. One approach known in the art provides a single enantiomer by separating a racemic mixture of the compound at the end of the reaction sequence. The present approach is to separate enantiomers several steps earlier in the sequence and thereby provide an efficient process. The present inventors have identified a racemic compound represented by formula (VIA) below as ideal for the separation.

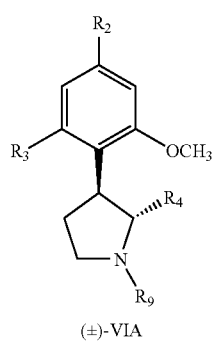

(±)-VIA wherein $R_2$, $R_3$, $R_4$ and $R_9$ are as defined, or a pharmaceutically acceptable salt thereof.

The resolution process of the present invention comprises reacting a racemic compound represented by formula ((±)-VIA) with a chiral auxiliary in the presence of a single solvent to obtain the corresponding mixture of diastereomeric salts of the (+)- and (−)-enantiomers of a compound of the formula (VIA), separating the respective diastereomeric salts and treating the diastereomeric salt of the (−)-enantiomer with a base to obtain the free base of the desired (−)-enantiomer of the compound represented by the following formula.

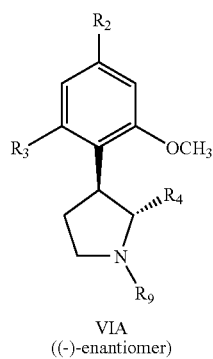

VIA
((−)-enantiomer)

In the resolution process according to the present invention, the chiral auxiliary is selected from: (−)-dibenzoyl tartaric acid ((−)-DBTA), (+)-dibutyl tartaric acid, (−)-dibutyl tartaric acid, (+)-ketopinic acid, (−)-ketopinic acid, (+)-camphor-10-sulfonic acid, (−)-camphor-10-sulfonic acid, (+)camphoric acid and (−)-camphoric acid. The most preferred chiral auxiliary is (−)-dibenzoyl tartaric acid ((−)-DBTA).

The single solvent used in the resolution step may be selected from: methanol, isopropanol, diisopropyl ether, ethyl acetate and chloroform. The most preferred solvent is methanol.

The base may be selected from: sodium bicarbonate, sodium carbonate and potassium carbonate. The most preferred base is sodium carbonate.

More particularly, there is provided a process for the resolution of a racemic compound of formula (VIA), wherein $R_2$ and $R_3$ are methoxy, $R_9$ is methyl and $R_4$ is hydroxymethyl, the compound being chemically known as (±)-trans[1-methyl-3-(2,4,6-trimethoxy-phenyl)-pyrrolidin-2-yl]methanol (designated herein as Compound A).

A process for the resolution of compound A is described in the applicant's co-pending published US Patent Application No. 2004/010658. This process involves numerous crystallization and recrystallisation steps. The resolved compound (−)-trans-[1-methyl-3-(2,4,6-trimethoxy-phenyl)-pyrrolidin-2-yl]-methanol (designated herein as Compound B) was obtained in a yield of 22-30% and reported optical rotation was −17.7° (c=1.1, methanol).

In a preferred embodiment of the present invention, a process involving resolution of the intermediate compound of formula (VIA), specifically the compound A, comprises reacting compound A with (−)-DBTA ((−)-dibenzoyl tartaric acid) as a chiral auxiliary methanol to yield the crystallized dibenzoyl tartarate salts of (+)- and (−)-trans-[1-methyl-3-(2, 4,6-trimethoxy-phenyl)-pyrrolidin-2-yl]-methanol. The preferred (−)-dibenzoyl tartarate salt of compound B is then converted to its free base by treatment of the diastereomeric salt with sodium carbonate.

The enantiomeric purity of compound B obtained by the process of the present invention was evaluated and compared with that obtained by using the resolution process reported in the aforesaid published US Patent Application No. 2004/0106581 using chiral HPLC. It was established that compound B obtained according to the process of the present invention is a single isomer with a 100% e.e. Whereas compound B was obtained in 88.3% e.e when prepared according to the process disclosed in the US Patent Application No. 2004/0106581.

Thus, not only do the single enantiomers obtained by the process according to the present invention have greater enantiomeric purity in comparison to the single enantiomers obtained by the known process, but the process according to the present invention is simpler and more cost effective than the known process as it involves a single step reaction to obtain the diastereomeric salt, namely the dibenzoyl tartrate salt. The present process involves single crystallization. Use of the chiral auxiliary (−)-DBTA has the additional advantage that it is comparatively cheaper than (+)-DBTA, which is used in the process reported in the published US Patent Application no. 2004/0106581, thereby reducing the overall cost of production.

The racemic compound of formula (VIA), a key intermediate in the preparation of the compound of formula (I), can be prepared as outlined in following Scheme 1.

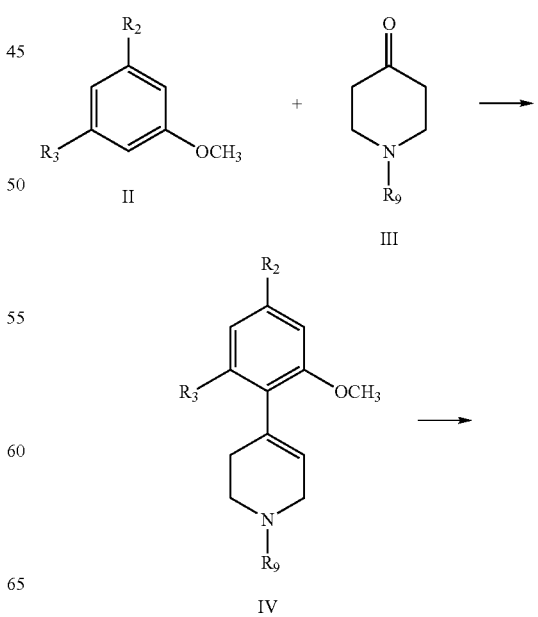

SCHEME 1

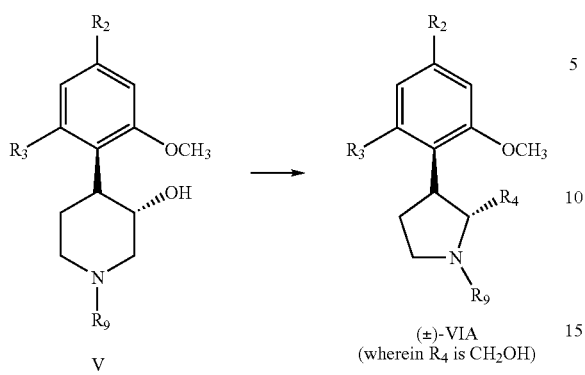

(±)-VIA
(wherein R₄ is CH₂OH)

V

The preparation steps up to the compound of formula (V) starting from the compound of formula (II) are described in U.S. Pat. No. 4,900,727, which is incorporated herein by reference. In the conversion of the compound of formula (V) to that of formula (VIA) in the above scheme, the hydroxyl function on the piperidine ring may be converted to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol. The ring contraction involved in this step may be effected before flavone formation as depicted in the above scheme or it may be done after building the flavone with the desired substitutions.

One embodiment of the present invention is an enantiomerically pure (−)-trans enantiomer of a compound of the formula (VIA) as defined above, where the enantiomeric purity is as defined.

Another embodiment of the present invention is the use of the enantiomerically pure (−)-trans enantiomer of an intermediate compound of the formula (VIA) as defined, for the preparation of an enantiomerically pure compound of the formula (I) as defined. By using an intermediate having a high enantiomeric purity as a starting compound in the process, the resultant (+)-trans enantiomer of pyrrolidines substituted with flavone represented by formula (I) produced by the process has a correspondingly high enantiomeric purity.

According to a preferred embodiment of the present invention, there is provided a process for the preparation of an enantiomerically pure (+)-trans enantiomer of a compound of formula (I), or a pharmaceutically acceptable salt thereof, from the resolved enantiomerically pure (−)-trans enantiomer of the intermediate compound of formula (VIA), which process comprises:

(a) treating the resolved enantiomerically pure (−)-trans enantiomer of the intermediate compound of formula (VIA),

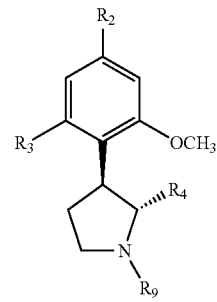

VIA wherein R₂, R₃, R₄ and R₉ are as defined, with acetic anhydride in the presence of a Lewis acid catalyst to obtain a resolved acetylated compound of formula (VIIA),

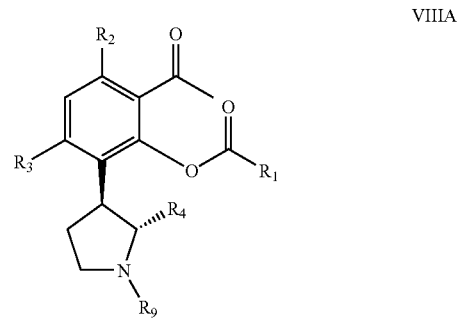

VIIA wherein R₂, R₃ and R₉ are as defined and R₄ is CH₂OC(O)CH₃;

(b) reacting the resolved acetylated compound of formula (VIIA) with an acid of formula R₁COOH or an acid chloride of formula R₁COCl or an acid anhydride of formula (R₁CO)₂O or an ester of formula R₁COOCH₃, wherein R₁ is as defined hereinabove, in the presence of a base and a solvent to obtain a resolved compound of formula (VIIIA)

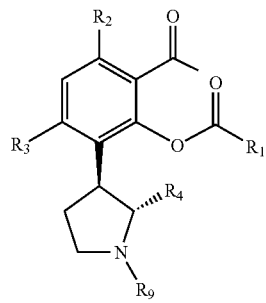

VIIIA wherein R₁, R₂, R₃ and R₉ are as defined herein above and R₄ is CH₂OC(O)CH₃;

(c) treating the resolved compound of formula (VIIIA) with a base in a suitable solvent to obtain the corresponding resolved β-diketone compound of formula (IXA);

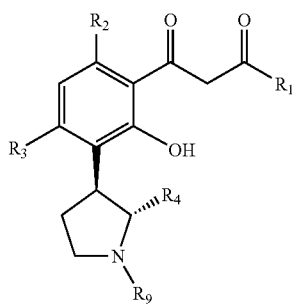

wherein $R_1$, $R_2$, $R_3$ and $R_9$ are as defined herein above and $R_4$ is $CH_2OC(O)CH_3$;

(d) treating the resolved β-diketone compound of formula (IXA) with an acid such as hydrochloric acid to obtain the corresponding cyclized compound of formula (XA),

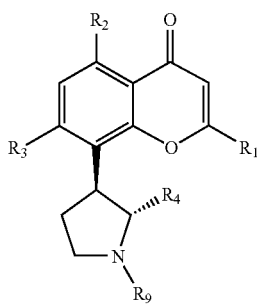

wherein $R_1$, $R_2$, $R_3$ and $R_9$ are as defined herein above, $R_4$ is $CH_2OH$;

(e) subjecting the compound of formula (XA) to dealkylation by heating it with a dealkylating agent at a temperature ranging from 120-180° C. to obtain the (+)-trans enantiomer of the compound of formula (I) (wherein $R_2$ and $R_3$ represent hydroxy) and, optionally, converting the subject compound into its pharmaceutically acceptable salt.

The Lewis acid catalyst utilized in the step (a) above may be selected from: $BF_3$, $Et_2O$, zinc chloride, aluminium chloride and titanium chloride.

The base utilized in the process step (b) may be selected from triethylamine, pyridine and a DCC-DMAP combination.

It will be apparent to those skilled in the art, the rearrangement of the compound of formula (VIIIA) to the corresponding β-diketone compound of formula (IXA) is known as a Baker-Venkataraman rearrangement (J. Chem. Soc., 1381 (1933) and Curr. Sci., 4, 214 (1933)).

The base used in the process step (c) may be selected from: lithium hexamethyldisilazide, sodium hexamethyldisilazide, potassium hexamethyldisilazide, sodium hydride and potassium hydride. Most preferred base is lithium hexamethyldisilazide.

The dealkylating agent used in process step (e) for the dealkylation of the compound of formula (IXA) may be selected from: pyridine hydrochloride, boron tribromide, boron trifluoride etherate and aluminium trichloride. Most preferred dealkylating agent is pyridine hydrochloride.

An alternative process for the preparation the compound of formula (I) comprises the steps of:

(i) hydrolysing the resolved acetylated compound of formula (VIIA) (obtained in step (a) of the process described hereinabove) with a base in the presence of a solvent to obtain the corresponding resolved alcohol of formula (XIA);

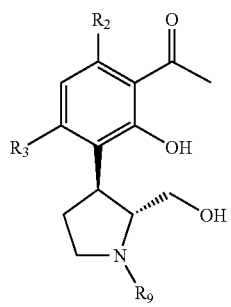

wherein $R_2$, $R_3$ and $R_9$ are as defined hereinabove;

(ii) treating the resolved compound of formula XIA with an acid of formula $R_1COOH$ or an acid chloride of formula $R_1COCl$ or an acid anhydride of formula $(R_1CO)_2O$, or an ester of formula $R_1COOCH_3$, wherein $R_1$ is as defined hereinabove, in the presence of a base and a suitable solvent under an atmosphere of nitrogen, followed by acid catalyzed cyclisation to obtain a compound of formula (XA);

(iii) subjecting the resolved compound of formula (XA) to dealkylation by heating it with a dealkylating agent at a temperature ranging from 120-180° C. to obtain the resolved (+)-enantiomer of the compound of formula (I) (wherein $R_2$ and $R_3$ represent hydroxyl group) and optionally, converting the resultant compound into its pharmaceutically acceptable salt.

In step (i) of the alternative process, the base may be selected from sodium hydroxide and potassium hydroxide and the solvent may be selected from: methanol and ethanol.

In step (ii) of the alternative process, the base may be selected from sodium hydride and potassium hydride and the solvent may be selected from: dimethylformamide, tetrahydrofuran and 1,4-dioxane.

The present invention also relates to all the resolved intermediates which are critical for the synthesis of the enntiomerically pure (+)-trans enantiomer of a compound of general formula (I).

More particularly the enantiomerically pure intermediates which are included within the scope of the present invention are compounds of formula (VIA), (VIIA), (VIIIA), (IXA), (XA) and (XIA):

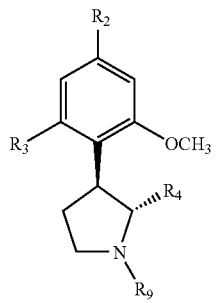

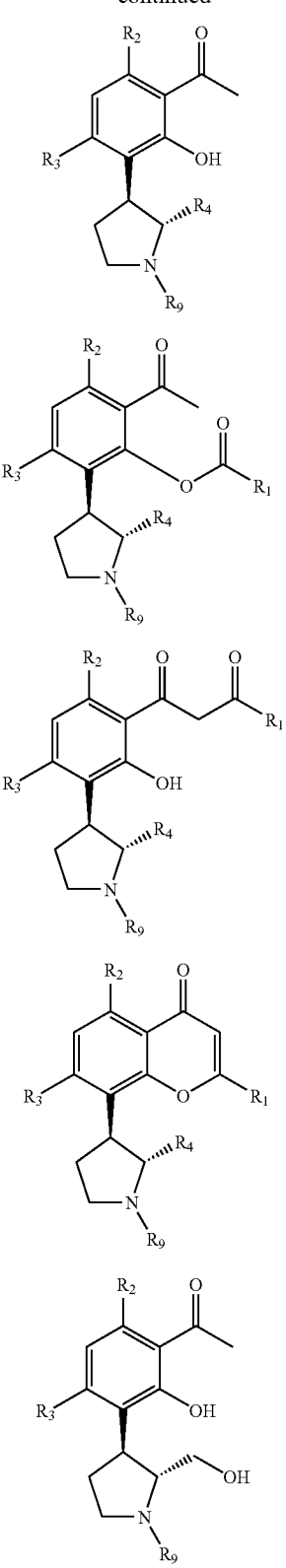

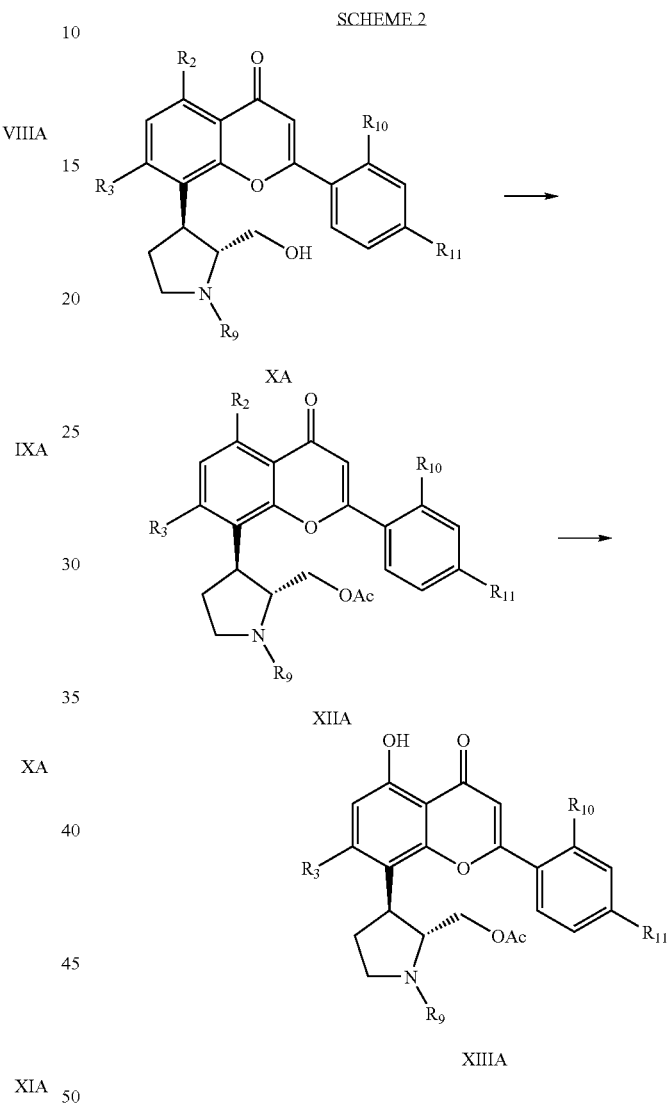

is phenyl substituted by $R_{10}$ and $R_{11}$ wherein $R_{10}$ and $R_{11}$ independently represent a group selected from: halogen, nitro, cyano, $C_1$-$C_4$-alkyl, fluoromethyl, difluoromethyl, trifluoromethyl, $C_1$-$C_4$-alkoxy, hydroxyl, carboxy, $C_1$-$C_4$-alkoxycarbonyl, $C_1$-$C_4$-alkylenehydroxyl, $CONH_2$, $CONR_5R_6$, $SO_2NR_5R_6$, cycloalkyl, $NR_5R_6$, $SR_7$; and $R_4$ is $CH_2OH$] is carried out as depicted in the following Scheme 2.

In the compounds of formula (VIA), (VIIA), (VIIIA), (IXA), (XA) and (XIA) the substituents $R_1$, $R_2$, $R_3$, $R_4$ and $R_9$ are as defined herein above.

In a specific embodiment of the present invention, selective demethylation of the compound of formula (XA) [wherein $R_1$ is phenyl substituted by $R_{10}$ and $R_{11}$...

As illustrated in Scheme 2 above, the hydroxy group in the compound of formula (XA) is protected with a suitable protecting group such as an acetyl group by treating the said compound of formula (XA) with an appropriate reagent like acetyl chloride or acetic anhydride in the presence of a base selected from: sodium hydride, potassium hydride, pyridine, triethylamine and dimethylaminopyridine(DMAP) to obtain the acetylated compound of formula XIIA. The compound of formula XIIA is then treated with a demethylating agent such as boron trifluoride etherate to obtain the compound of formula XIIIA.

This invention also encompasses prodrugs of the enantiomerically pure compounds of formula (I) and pharmaceutical compositions containing the same and methods of treatment through administering such prodrugs.

Another aspect of the present invention is to provide a process for the preparation of a prodrug of a resolved compound of formula (I), which process comprises, treating the resolved compound of formula (I), wherein $R_2$ and $R_3$ are hydroxyl, with an acid or acid chloride in the presence of a base to yield a prodrug of the resolved compound of formula (I), wherein $R_2$ is hydroxy, $R_3$ is hydroxy, OCOR or OR, and $R_4$ is alkyleneOH or alkyleneOC(O)R; wherein R is alkyl or aryl. One such prodrug is a compound of the formula (XIVA).

An example of the preparation of a prodrug of the enantiomerically pure compound of formula (I) is depicted in the following Scheme 3

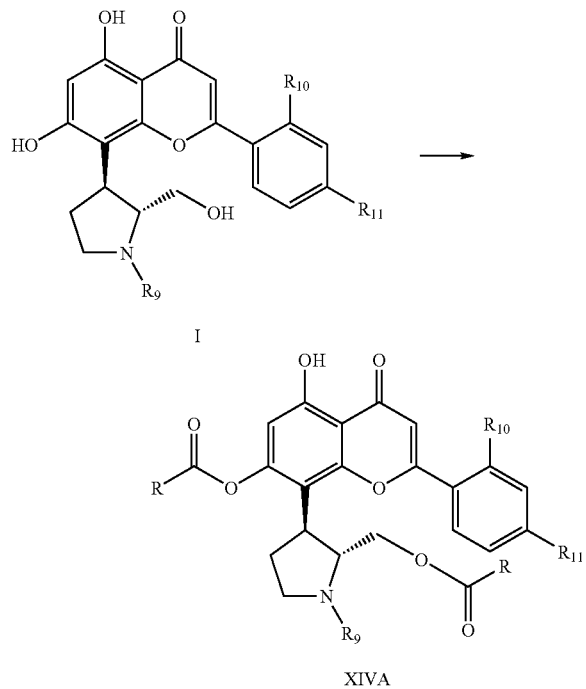

The process comprises reacting the enantiomerically pure compound of formula (I), wherein, $R_2$ and $R_3$ are hydroxy groups, with an acid or an acid chloride in the presence of a base selected from: sodium hydride, potassium hydride, pyridine, trimethylamine and DMAP to yield the enantiomerically pure (+)-trans enantiomer prodrug of formula (XIVA), wherein $R_2$ is hydroxy, $R_3$ is OC(O)R, $R_4$ is alkyleneOC(O)R; where R is alkyl or aryl. In the compounds of formula XIVA and I, $R_{10}$ and $R_{11}$ are as defined above.

According to the present invention, the compounds of the general formula (I) are inhibitors of CDKs, particularly CDK/cyclin complexes and find use in antiproliferative therapies for diseases characterized by excessive cell growth such as cancers, cardiovascular abnormalities, nephrological disorders, psoriasis, parasitalogy, Alzheimer's disease, inflammation and arthritis, immunological disorders involving unwanted proliferation of leukocytes, restenosis and other proliferative smooth muscle disorders, viral infections, and mycotic infections.

The present invention thus relates to the enantiomerically pure compounds of the formula (I), and/or their pharmaceutically acceptable salts and/or their prodrugs for use as pharmaceuticals (or medicaments), to the use of the enantiomerically pure compounds of the formula (I) and/or their physiologically tolerable salts and/or their prodrugs for the production of pharmaceuticals for the inhibition of cell proliferation or for the therapy or prophylaxis of the diseases mentioned above, for example for the production of pharmaceuticals for the therapy and prophylaxis of cancer, inflammation and arthritis, psoriasis, bone diseases, mycotic or viral infections, cardiovascular disorders, Alzheimers's disease etc., and to methods of treatment aiming at such purposes including methods for said therapies and prophylaxes. The present invention furthermore relates to pharmaceutical compositions that contain an effective amount of at least one enantiomerically pure compound of the formula (I) and/or its physiologically tolerable salts and/or its prodrugs in addition to a customary pharmaceutically acceptable carrier, optionally, with other active anti-proliferative agents, and to a process for the production of a pharmaceutical, which comprises bringing at least one enantiomerically pure compound of formula (I) into a suitable administration form using a pharmaceutically suitable and physiologically tolerable carrier and, if appropriate, further suitable active compounds and/or additives. These compositions can be prepared by applying known techniques in the art such as those taught in "*Remington's Pharmaceutical Sciences*", published by Mack Publishing Co. or "*Pharmaceutical Dosage Form and Drug Delivery Systems*" (Sixth Edition), published by Williams & Wilkins, (1995), each of which is hereby incorporated by reference.

The present invention also relates to a method for the preparation of a medicament for the treatment or prevention of disorders associated with excessive cell proliferation, characterized in that at least one enantiomerically pure compound of the general formula (I) is used as the pharmaceutically active substance.

The pharmaceutical compositions normally contain about 1 to 99%, preferably about 5 to 70%, most preferably from about 10 to about 30% by weight of the enantiomerically pure compounds of the formula (I) and/or their physiologically tolerable salts and/or their prodrugs. The amount of the active ingredient of the enantiomerically pure compound of the formula (I) and/or its physiologically tolerable salts and/or its prodrugs in the pharmaceutical compositions normally is from about 5 to 500 mg. The dose of the enantiomerically pure compounds of this invention, which is to be administered, can cover a wide range. The dose to be administered daily is to be selected to suit the desired effect. About 20 to 1,000 mg are preferably administered daily per patient. If required, higher or lower daily doses can also be administered. Actual dosage levels of the active ingredients in the pharmaceutical compositions of this invention may be varied so as to obtain an amount of the active ingredient which is effective to achieve the desired therapeutic response for a particular patient, composition, and mode of administration without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

The pharmaceuticals can be administered orally, including sublingually, for example in the form of pills, tablets, coated tablets, capsules, granules, powders, syrups or elixirs. Administration, however, can also be carried out: rectally or vaginally, for example in the form of suppositories; parentally, for example intravenously, intramuscularly or subcutaneously, including by the use of infusion techniques, in the form of injectable sterile solutions or suspensions; topically, for example in the form of creams, ointments, lotions, foams, gels, emulsions, solutions, tinctures, magmas or transdermal patches; or by other routes, for example ophthalmically, optically, nasally, or in other forms, for example, aerosols, inhalants or nasal sprays.

The pharmaceutical compositions according to the invention are prepared in a manner known per se and familiar to one skilled in the art. Pharmaceutically acceptable inert inorganic and/or organic carriers and/or additives can be used in addition to the compound(s) of the formula (I) and/or its (their) physiologically tolerable salts and/or its (their) prodrugs. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, wax, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned. Additives that may be used are, for example, fillers, antioxidants, dispersants, emulsifiers, defoamers, flavor corrigants, preservatives, solubilizers or colorants.

Commonly used pharmaceutically acceptable carriers and additives which can be used as appropriate to formulate the composition for its intended route of administration are well known in the art and include those carriers and additives described in the applicant's published US patent application no. 2004/0106581.

The pharmaceutical compositions can also contain two or more enantiomerically pure compounds of the formula (I) and/or their physiologically tolerable salts and/or their prodrugs. Furthermore, in addition to at least one enantiomerically pure compound of the formula (I) and/or its physiologically tolerable salts and/or its prodrugs, the pharmaceutical compositions can also contain one or more other therapeutically or prophylactically active ingredients. Thus, the compounds of the present invention may be used as drugs in the treatment of proliferative disorders either alone or as part of combined therapies. For instance, the enantiomerically pure compounds of the present invention may be used in combination with known anti-cancer, cytostatic, and cytotoxic agents. If formulated as a fixed dose, such combination products employ the compounds of the present invention within the dosage range described above and the other pharmaceutically active agent within its approved dosage range. For example, the CDK inhibitor olomoucine has been found to act synergistically with known cytotoxic agents in inducing apoptosis (J. Cell Sci., 1995, 108, 2897). The enantiomerically pure compounds of general formula (I) may be used sequentially with known drugs such as anticancer or cytotoxic agents when a combination formulation is inappropriate.

Optional anti-proliferative agents which can be added to the composition include but are not limited to compounds listed on the cancer chemotherapy drug regimens in the 13$^{th}$ Edition of the Merck Index, (1996) (NB Year or edition requires correction), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin, epirubicin, etoposide, fluorouracil, hexamethylmelamine, hydroxyurea, ifosfamide, leucovorin, lomustine, mechlorethamine, 6-mercaptopurine, mesna, methotrexate, mitomycin C, mitoxantrone, prednisolone, prednisone, procarbazine, streptozocin, tamoxifen, thioguanine, vinblastine, vincristine, vindesine.

Other anti-proliferative agents suitable for use with the composition of the invention include but are not limited to those compounds acknowldeged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, vinorelbine.

Optional cyclin-dependent kinase (CDK) inhibiting agents which can be added to the composition include but are not limited to alsterpaullone, butyrolactone I, CDK2 inhibitor, CDK2/Cyclin Inhibitory Peptide I, CDK2/Cyclin Inhibitory Peptide II, 2-(2-hydroxyethylamino)-6-(3-chloroanilino)-9-isopropylpurine, indirubin-3'-monoxime, kenpaullone, olomoucine, iso-olomoucine, $N^9$-isopropyl-olomoucine, purvalanol A, roscovitine, (S)-isomer roscovitine and WHI-P180 [4-(3'-hydroxyphenyl)amino-6,7-dimethoxyquinazoline] (from Calbiochem Signal Transduction Catalog & Technical Resource 2001).

It is understood that modifications that do not substantially affect the activity of the various embodiments of this invention are included within the invention disclosed herein. Accordingly, the following examples are intended to illustrate but not to limit the present invention.

EXAMPLES

The following abbreviations are used herein:
$BF_3$: Boron trifluoride diethyl etherate
Conc.: Concentrated
THF: Tetrahydrofuran
EtOAc: Ethyl acetate
MeOH: Methanol
IPA: Isopropanol
DBTA: Dibenzoyl tartaric acid
DMF: N,N-Dimethyl formamide
DCC: N,N-dicyclohexylcarbodiimide
DMAP: (N,N-dimethylamino)pyridine
HCl: Hydrochloric acid
$NaBH_4$: Sodium borohydride
NaOH: Sodium hydroxide
$Na_2CO_3$: Sodium carbonate Example 1

1-Methyl-4-(2,4,6-trimethoxyphenyl)-1,2,3,6-tetrahydropyridine 1-methyl-4-piperidone (340 g, 3.0 mol) was added slowly, to a solution of 1,3,5-trimethoxybenzene (500 g, 2.97 mol) in glacial acetic acid (600 mL), maintaining the temperature of the reaction mixture below 40° C. Conc. HCl (450 mL) was added over 20 min. The temperature was raised to 85-90° C. and the reaction mixture was stirred for 3.5 h. It was allowed to cool to 40° C., poured over crushed ice (4 kg) and stirred for 20 min. The precipitate of unreacted 1,3,5-trimethoxybenzene was filtered off. The filtrate was basified, below 10° C., to pH 11-12 using a 50% aqueous NaOH solution. The off white solid obtained was filtered, washed with water and dried to obtain the compound, 1-methyl-4-(2,4,6-trimethoxyphenyl)-1,2,3,6-tetrahydropyridine.

Yield: 580 g (74%);
mp: 112-114° C.;
IR (KBr): 3045, 2900, 2837, 1600, 1585 cm$^{-1}$;
$^1$H NMR (CDCl$_3$, 300 MHz): δ 6.15 (s, 2H), 5.55 (s, 1H), 3.85 (s, 3H), 3.75 (s, 6H), 3.10 (d, 2H), 2.55 (t, 2H), 2.40 (s, 3H), 2.35 (m, 2H);
MS (EI): m/z 263 (M$^+$).

Example 2

(±)-trans-1-Methyl-4-(2,4,6-trimethoxyphenyl)-piperidin-3-ol

Boron trifluoride diethyl etherate (300 mL, 2.36 mol) was added slowly with stirring, under an atmosphere of nitrogen, at 0° C., to a solution of compound of example (1) (300 g, 1.14 mol) and NaBH$_4$ (75 g, 1.97 mol) in dry THF (2.25 L). The temperature of the reaction mixture was slowly raised to 55° C. and stirred for 1.5 h. It was cooled to 30° C. Ice cold water (100 mL) was slowly added followed by acidification with conc. HCl (375 mL). The reaction mixture was stirred for 1 h. at 50-55° C. It was cooled to 30° C. and basified using 50% aqueous NaOH solution to pH 11-12. Hydrogen peroxide (30%, 225 mL) was added over 0.5 h. The reaction mixture was stirred at 55-60° C. for 1.5 h. It was cooled to 30° C. and sufficient water was added to dissolve the precipitated salts. The organic layer was separated and the aqueous portion extracted with ethyl acetate(2×1 L). The organic extracts were dried (anhydrous Na$_2$SO$_4$) and concentrated. The crude viscous brown oil obtained was treated with 4N HCl (1.2 L) and extracted with ethyl acetate (2×500 mL). The aqueous portion was cooled, basified with 50% aqueous sodium hydroxide solution and extracted using ethyl acetate (2×1 L). The organic extract was dried (anhydrous Na$_2$SO$_4$) and concentrated to give the compound, (±)-trans-1-methyl-4-(2,4,6-trimethoxy-phenyl)-piperidin-3-ol Yield: 210 g (65.6%);
mp: 96-97° C.;
IR (KBr): 3582, 3374, 3017 cm$^{-1}$;
$^1$H NMR (CDCl$_3$, 300 MHz): δ 6.15 (s, 2H), 4.40 (m, 1H), 3.79 (s, 3H), 3.74 (s, 6H), 3.20 (dd, 1H), 3.00 (m, 1H), 2.80 (m, 1H), 2.40 (m, 1H), 2.37 (s, 3H), 2.00 (m, 1H), 1.90 (t, 1H), 1.52 (m, 1H);
MS (CI): m/z 282 (M+1).

Example 3

(±)-trans-Acetic acid-1-methyl-3-(2,4,6-trimethoxyphenyl)-pyrrolidin-2-yl methyl ester Methanesulfonyl chloride (30.27 mL, 44.8 g, 0.4 mol) was added drop wise to a cooled and stirred solution of compound of example (2) (100 g, 0.35 mol) and triethylamine (71.88 g, 0.7 mol) in dry THF (1.0 L). The reaction mixture was further stirred for 45 min. at 0° C. The precipitate of triethylamine HCl was filtered and washed with dry THF (2×100 mL). The filtrate was added dropwise to a refluxing suspension of sodium acetate (115 g, 1.40 mol) in 2-propanol (1.0 L). The reaction mixture was refluxed for a further 15 min., diluted with EtOAc (1.0 L) and salts were filtered. The mixture of salts was washed with EtOAc (2×100 mL). The combined filtrate was concentrated to give a gum. Water (50 mL) was added to the gum with stirring to obtain a solid which was filtered and dried to yield the compound, (±)-trans-acetic acid 1-methyl-3-(2,4,6-trimethoxy-phenyl)-pyrrolidin-2-yl methyl ester.

Yield: 90 g (81%);
mp: 74-77° C.;
$^1$H NMR (CDCl$_3$, 300 MHz): δ 6.13 (s, 2H), 4.00 (m, 2H), 3.81 (m, 1H), 3.79 (s, 3H), 3.76 (s, 6H), 3.20 (m, 1H), 2.75 (m, 1H), 2.69 (m, 1H), 2.47 (s, 3H), 2.00 (m, 2H), 1.99 (s, 3H).

Example 4

(±)-trans-[1-Methyl-3-(2,4,6-trimethoxyphenyl)-pyrrolidin-2-yl]-methanol

A 10% aqueous NaOH solution (596 mL) was added to a solution of the compound of example (3) (241 g, 0.75 mol) in methanol (596 mL). The reaction mixture was stirred at 50° C. for 45 min. It was concentrated to a gum and then poured into ice-cold water (2 L). The resulting solid was filtered to obtain the compound, (±)-trans-[1-methyl-3-(2,4,6-trimethoxy-phenyl)-pyrrolidin-2-yl]-methanol.

Yield: 198 g (94%);
mp: 82-85° C.;
IR (KBr): 3421, 3009, 1607 cm$^{-1}$;
$^1$H NMR (CDCl$_3$, 300 MHz): δ 6.15 (s, 2H), 3.92 (m, 1H), 3.80 (s, 9H), 3.60 (dd, 1H), 3.45 (d, 1H), 3.20 (m, 1H), 2.78 (m, 1H), 2.50 (m, 1H), 2.42 (s, 3H), 2.00 (m, 1H), 1.92 (m, 1H);
MS (ES+): m/z 282 (M+1).

Example 5

(−)-trans-[1-Methyl-3-(2,4,6-trimethoxyphenyl)-pyrrolidin-2-yl]-methanol (−)-DBTA (321.7 g, 897.7 mmol) was added to the compound of example (4) (250 g, 889.6 mmol) followed by addition of methanol (1715 mL). The mixture was refluxed for 10 min., stirred slowly at room temperature for 3 h., the crystallised salt was filtered and dried.

Yield: 185 g (30%);
mp: 102-105° C.;
$[α]_D^{25}$=−82.66° (c=0.7, methanol).

The salt was stirred with 10% aqueous solution of Na$_2$CO$_3$ (765 mL) and EtOAc (200×3 mL) to obtain the free base in the EtOAc layer. The EtOAc layer was concentrated to obtain the compound, (−)-trans-[1-methyl-3-(2,4,6-trimethoxy-phenyl)-pyrrolidin-2-yl]-methanol.

Yield: 80 g (98.3%);
$[α]_D^{25}$=−20.0° (c=0.7, methanol);
$^1$H NMR (CDCl$_3$, 300 MHz): δ 6.13 (s, 2H), 3.90 (m, 1H), 3.79 (s, 9H), 3.57 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

This compound was subjected to chiral HPLC. Chiral HPLC was done using column Chiralcel OD-H (250×4.6 mm) and solvent system haxane:ethanol (92:08) with TFA (0.4%). The results are recorded at 264 nm with solvent flow rate of 1 mL/min. As depicted in FIG. 1, the chiral HPLC showed 100% e.e of the compound, (−)-trans-[1-Methyl-3-(2,4,6-trimethoxy-phenyl)-pyrrolidin-2-yl]-methanol.

Example 6

(−)-trans-Acetic acid-3-(3-acetyl-2-hydroxy-4,6-dimethoxyphenyl)-1-methyl-pyrrolidin-2-yl methyl ester $BF_3$-etherate (25.2 g, 178 mmol) was added dropwise, with stirring, at 0° C., under $N_2$ atmosphere to a solution of the compound of example (5) (10 g, 35.58 mmol) in acetic anhydride (19.48 mL, 176 mmol). The reaction mixture was stirred at room temperature for 2 h. It was poured over crushed ice (1 kg), basified using a saturated aqueous $Na_2CO_3$ solution and extracted using EtOAc (3×200 mL). The organic extract was washed with brine, dried (anhydrous $Na_2SO_4$) and concentrated to obtain the compound, (−)-trans-acetic acid 3-(3-acetyl-2-hydroxy-4,6-dimethoxy-phenyl)-1-methyl-pyrrolidin-2-yl methyl ester.

Yield: 10 g (83%);
$^1$H NMR ($CDCl_3$, 300 MHz): δ14.20 (s, 1H), 5.96 (s, 1H), 4.10 (d, 2H), 3.90 (s, 3H), 3.89 (s, 3H), 3.85 (m, 1H), 3.26 (m, 1H), 2.82 (m, 1H), 2.74 (m, 1H), 2.66 (s, 3H), 2.52 (s, 3H), 2.21 (m, 2H), 2.10 (s, 3H).

Example 7

(−)-trans-1-[2-Hydroxy-3-(2-hydroxymethyl-1-methylpyrrolidin-3-yl)-4,6-dimethoxyphenyl)-ethanone To a solution of the compound of example (6) (10 g, 28.4 mmol) in methanol (25 mL) was added with stirring, at room temperature, a 10% aqueous NaOH (25 mL) solution. The temperature of the reaction mixture was raised to 50° C. for 45 min. It was cooled to room temperature, acidified using conc. HCl and concentrated to remove methanol. It was basified using a saturated aqueous $Na_2CO_3$ solution. The compound, (−)-trans-1-[2-hydroxy-3-(2-hydroxymethyl-1-methyl-pyrrolidin-3-yl)-4,6-dimethoxy-phenyl)-ethanone, was filtered, washed with water and dried.

Yield: 7.14 g (82%);
IR (KBr): 3400, 3121, 3001, 1629, 1590 $cm^{-1}$;
$^1$H NMR ($CDCl_3$, 300 MHz): δ 5.96 (s, 1H), 3.93 (m, 1H), 3.90 (s 3H), 3.88 (s, 3H), 3.59 (dd, 1H), 3.37 (d, 1H), 3.13 (m, 1H), 2.75 (m, 1H), 2.61 (s, 3H), 2.59 (m, 1H), 2.37 (s, 3H), 2.00 (m, 2H);
MS (ES+): m/z 310 (M+1).

Example 8

(+)-trans-2-(2-Chlorophenyl)-8-(2-hydroxymethyl-1-methylpyrrolidin-3-yl)-5,7-dimethoxy-chromen-4-one Sodium hydride (50%, 0.54 g, 11.25 mmol) was added in portions to a solution of the compound of example (7) (0.7 g., 2.2 mmol) in dry DMF (15 mL) at 0° C., under nitrogen atmosphere and with stirring. After 10 min., methyl 2-chlorobenzoate (1.15 g., 6.75 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated $Na_2CO_3$ (pH 10) and extracted using $CHCl_3$ (3×200 mL). The organic layer was dried (anhydrous $Na_2SO_4$) and concentrated. To the residue, conc. HCl (25 mL) was added and stirred at room temperature for 2 h. The reaction mixture was poured over crushed ice (300 g) and made basic using a saturated aqueous $Na_2CO_3$ solution. The mixture was extracted using $CHCl_3$ (3×200 mL). The organic extract was washed with water, dried (anhydrous $Na_2SO_4$) and concentrated to obtain the compound, (+)-trans-2-(2-chloro-phenyl)-8-(2-hydroxymethyl-1-methyl-pyrrolidin-3-yl)-5,7-dimethoxy-chromen-4-one.

Yield: 0.67 g (64%);
mp: 91-93° C.;
$[\alpha]_D^{25}$=+5.8° (c=0.7, methanol);
IR (KBr): 3431, 1648, 1598, 1571 $cm^{-1}$;
$^1$H NMR ($CDCl_3$, 300 MHz): δ 7.70 (dd, 1H), 7.52 (m, 1H), 7.45 (m, 2H), 6.50 (s, 1H), 6.44 (s, 1H), 4.17 (m, 1H), 4.00 (s, 3H), 3.97 (s, 3H), 3.64 (dd, 1H), 3.40 (d, 1H), 3.15 (m, 1H), 2.74 (d, 1H), 2.52 (m, 1H), 2.32 (s, 3H), 2.00 (m, 2H);
MS (ES+): m/z 430 (M+1).

Example 9

(+)-trans-2-(2-Chlorophenyl)-5,7-dihydroxy-8-(2-hydroxymethyl-1-methyl-pyrrolidin-3-yl)-chromen-4-one Molten pyridine hydrochloride (4.1 g, 35.6 mmol) was added to the compound of example (8) (0.4 g, 0.9 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (5 mL), stirred for 30 min., filtered and dried to obtain the compound, (+)-trans-2-(2-chloro-phenyl)-5,7-dihydroxy-8-(2-hydroxymethyl-1-methyl-pyrrolidin-3-yl)-chromen-4-one.

Yield: 0.25 g (70%);
IR (KBr): 3422, 3135, 1664, 1623, 1559 $cm^{-1}$;
$^1$H NMR ($CDCl_3$, 300 MHz): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H);
MS (ES+): m/z 402 (M+1);
Analysis: $C_{21}H_{20}ClNO_5$ C, 62.24 (62.71); H, 5.07 (4.97); N, 3.60 (3.48); Cl, 9.01 (8.83).

Example 10

(+)-trans-2-(2-Chlorophenyl)-5,7-dihydroxy-8-(2-hydroxymethyl-1-methyl-pyrrolidin-3-yl)-chromen-4-one hydrochloride The compound of example (9) (0.2 g, 0.48 mmol) was suspended in IPA (5 mL) and 3.5% HCl (25 mL) was added. The suspension was heated to get a clear solution. The solution was cooled and solid filtered to obtain the compound, (+)-trans-2-(2-Chlorophenyl)-5,7-dihydroxy-8-(2-hydroxymethyl-1-methyl-pyrrolidin-3-yl)-chromen-4-one hydrochloride.

Yield: 0.21 g (97%);
mp: 188-192° C.;
$[\alpha]_D^{25}$=+21.3° (c=0.2, methanol);
$^1$H NMR ($CD_3OD$, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H);
MS (ES+): m/z 402 (M+1)(free base).

Figure 3:
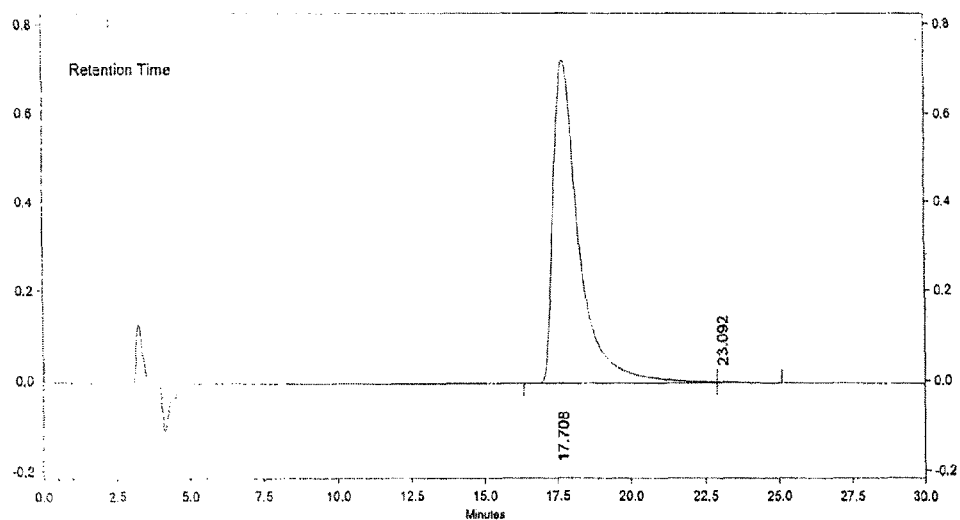
FIG. 3: Chiral HPLC (Chiralcel OD-H (250×4.6 mm) Column) of (+)-trans-2-(2-chlorophenyl)-5,7-dihydroxy-8-(2-hydroxymethyl-1-methyl-pyrrolidin-3-yl)-chromen-4-one hydrochloride obtained as described in Example 10.

This compound was subjected to chiral HPLC. Chiral HPLC was done using column Chiralcel OD-H (250×4.6 mm) and solvent system haxane:ethanol (92:08) with TFA (0.4%). The results are recorded at 264 nm with solvent flow rate of 1 mL/min. As depicted in FIG. 3, the chiral HPLC showed 100% e.e of the compound, (+)-trans-2-(2-chlorophenyl)-5,7-dihydroxy-8-(2-hydroxy-methyl-1-methyl-pyrrolidin-3-yl)-chromen-4-one hydrochloride

Example 11

(+)-trans-2-(2-Chloro-5-fluorophenyl)-8-(2-hydroxymethyl-1-methyl-pyrrolidin-3-yl)-5,7-dimethoxy-chromen-4-one Sodium hydride (50%, 0.776 g, 16 mmol) was added in portions to a solution of compound of example (7) (1.0 g, 3.2 mmol) in dry DMF (25 mL) at 0° C., under nitrogen atmosphere and with stirring. After 10 min., methyl 2-chloro-5-fluorobenzoate (1.22 g, 6.4 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated $Na_2CO_3$ (pH 10) and extracted using $CHCl_3$ (3×200 mL). The organic layer was dried (anhydrous $Na_2SO_4$) and concentrated. To the residue, conc. HCl (25 mL) was added and stirred at room temperature for 2 h. The reaction mixture was poured over crushed ice (300 g) and made basic using a saturated aqueous $Na_2CO_3$ solution. The mixture was extracted using $CHCl_3$ (3×200 mL). The organic extract was washed with water, dried (anhydrous $Na_2SO_4$) and concentrated to obtain the compound, (+)-trans-2-(2-chloro-5-fluoro-phenyl)-8-(2-hydroxymethyl-1-methyl-pyrrolidin-3-yl)-5,7-dimethoxy-chromen-4-one.

Yield: 0.9 g (63%);
$^1$H NMR ($CDCl_3$, 300 MHz): δ 7.57 (m, 1H), 7.46 (m, 1H), 7.16 (m, 1H), 6.58 (s, 1H), 6.45 (s 1H), 4.15 (m, 1H), 4.00 (s, 3H), 3.97 (s, 3H), 3.63 (dd, 1H), 3.32 (d, 1H), 3.13 (m, 1H), 2.61 (m, 1H), 2.53 (m, 1H), 2.29 (s, 3H), 2.00 (m, 2H); MS (CI):

m/z 448 (M+1).

Example 12

(+)-trans-2-(2-Chloro-5-fluorophenyl)-5,7-dihydroxy-8-(2-hydroxymethyl-1-methylpyrrolidin-3-yl)-chromen-4-one Molten pyridine hydrochloride (8.0 g, 69.5 mmol) was added to compound of example (11) (0.8 g, 1.78 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (10 mL), stirred for 30 min., filtered and dried to obtain the compound, (+)-trans-2-(2-chloro-5-fluoro-phenyl)-5,7-dihydroxy-8-(2-hydroxymethyl-1-methyl-pyrrolidin-3-yl)-chromen-4-one.

Yield: 0.45 g (60%);
mp: 253-254° C.;
IR (KBr): 3450, 1665 $cm^{-1}$;
$^1$H NMR (DMSO $d_6$, 300 MHz): δ 12.70 (s, 1H), 7.75 (m, 2H), 7.54 (m, 1H), 6.55 (s, 1H), 6.14 (s, 1H), 3.80 (m, 1H), 3.51 (m, 3H), 2.94 (m, 2H), 2.46 (s, 3H), 2.15 (m, 1H), 1.86 (m, 1H);
MS (ES+): m/z 420 (M+1);
Analysis: $C_{21}H_{19}ClFNO_6$ C, 60.2 (60.08); H, 4.53 (4.56); N, 3.86 (3.34); Cl, 8.17 (8.44).

Example 13

(+)-trans-2-(2-Chloro-5-fluorophenyl)-5,7-dihydroxy-8-(2-hydroxymethyl-1-methylpyrrolidin-3-yl)-chromen-4-one hydrochloride Compound of example (12) (0.1 g, 0.244 mmol) was suspended in IPA (5 mL) and 3.5% HCl (25 mL) was added. The suspension was heated to get a clear solution. The solution was cooled and solid filtered to obtain the compound, (+)-trans-2-(2-chloro-5-fluoro-phenyl)-5,7-dihydroxy-8-(2-hydroxymethyl-1-methyl-pyrrolidin-3-yl)-chromen-4-one hydrochloride.

Yield: 0.108 g (100%);
$[α]_D^{25}$=+18.05° (c=0.7, methanol);
$^1$H NMR ($CD_3OD$, 300 MHz): δ 7.67 (m, 2H), 7.37 (m, 1H), 6.60 (s, 1H), 6.37 (s, 1H), 4.25 (m, 1H), 3.90 (m, 2H), 3.69 (m, 1H), 3.60 (dd, 1H), 3.45 (m, 1H), 2.98 (s, 3H), 2.52 (m, 1H), 2.29 (m, 1H);
MS (ES+): m/z 420 (M−36.5).

Example 14

(+)-trans-2-(2-Bromo-5-fluorophenyl)-8-(2-hydroxymethyl-1-methyl-pyrrolidin-3-yl)-5,7-dimethoxy-chromen-4-one Compound of example (7) (6 g, 19.42 mmol) in dry DMF (60 mL) was reacted with methyl 2-bromo-5-fluorobenzoate (6.7 g, 28.75 mmol) in the presence of NaH (50%, 3.88 g, 80.8 mmol) at 0° C., under nitrogen atmosphere. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated $Na_2CO_3$ (pH 10) and extracted using $CHCl_3$ (3×200 mL). The organic layer was dried (anhydrous $Na_2SO_4$) and concentrated. To the residue, conc. HCl (25 mL) was added and stirred at room temperature for 2 h. The reaction mixture was poured over crushed ice (300 g) and made basic using a saturated aqueous $Na_2CO_3$ solution. The mixture was extracted using $CHCl_3$ (3×200 mL). The organic extract was washed with water, dried (anhydrous $Na_2SO_4$) and concentrated to obtain the compound, (+)-trans-2-(2-bromo-5-fluoro-phenyl)-8-(2-hydroxymethyl-1-methyl-pyrrolidin-3-yl)-5,7-dimethoxy-chromen-4-one.

Yield: 3.94 g (41.2%);
$^1$H NMR ($CDCl_3$, 300 MHz): δ 7.65 (m, 1H), 7.45 (m, 1H), 7.10 (m, 1H), 6.47 (s, 1H), 6.45 (s, 1H), 4.15 (m, 1H), 4.00 (s, 3H), 3.97 (s, 3H), 3.64 (dd, 1H), 3.35 (d, 1H), 3.10 (m, 1H), 2.64 (m, 1H), 2.45 (m, 1H), 2.27 (s, 3H), 2.00 (m, 2H);
MS (ES+): m/z 493 (M+1).

Example 15

(+)-trans-2-(2-Bromo-5-fluorophenyl)-5,7-dihydroxy-8-(2-hydroxymethyl-1-methylpyrrolidin-3-yl)-chromen-4-one Molten pyridine hydrochloride (39 g, 339 mmol) was added to compound of example (14) (3.9 g, 7.92 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (40 mL), stirred for 30 min., filtered and dried to obtain the compound, (+)-trans-2-(2-bromo-5-fluoro-phenyl)-5,7-dihydroxy-8-(2-hydroxymethyl-1-methyl-pyrrolidin-3-yl)-chromen-4-one Yield: 1.4 g (38.14%);
mp: 145-147° C.;
IR (KBr): 3650, 1640 cm$^{-1}$;
$^1$H NMR (CDCl$_3$+TFA, 300 MHz): δ 12.40 (s, 1H), 7.55 (m, 1H), 7.28 (m, 1H), 7.00 (m, 1H), 6.31 (s, 1H), 6.28 (s, 1H), 3.98 (m, 1H), 3.68 (m, 2H), 3.50 (m, 2H), 3.15 (m, 1H), 2.80 (s, 3H), 2.30 (m, 1H), 2.08 (m, 1H);
MS (ES+): m/z 465 (M+1).

Example 16

(+)-trans-2-(2-Bromo-5-fluorophenyl)-5,7-dihydroxy-8-(2-hydroxymethyl-1-methylpyrrolidin-3-yl)-chromen-4-one hydrochloride Compound of example (15) (1.0 g) was converted to its hydrochloride salt by suspending in IPA (5 mL) and 3.5% HCl (25 mL). The suspension was heated to get a clear solution. The solution was cooled and solid filtered to obtain the compound, (+)-trans-2-(2-bromo-5-fluoro-phenyl)-5,7-dihydroxy-8-(2-hydroxy-methyl-1-methyl-pyrrolidin-3-yl)-chromen-4-one hydrochloride.

Yield: 1.0 g (93%); MS (ES+): m/z 465 (M+1)(free base).

Example 17

(+)-trans-2-(2-Bromo-5-fluorophenyl)-5,7-dihydroxy-8-(2-hydroxymethyl-1-methylpyrrolidin-3-yl)-chromen-4-one methane sulfonate Compound of example (15) (1.97 g, 4.25 mmol) in methanol (5 mL) was treated with methane sulfonic acid solution in methanol (0.408 g, 4.25 mmol). A clear solution obtained was concentrated to obtain the title compound, (+)-trans-2-(2-bromo-5-fluoro-phenyl)-5,7-dihydroxy-8-(2-hydroxymethyl-1-methyl-pyrrolidin-3-yl)-chromen-4-one methane sulfonate.

Yield: 2.3 g (96.63%);
$^1$H NMR (D$_2$O, 300 MHz): δ 7.58 (m, 1H), 7.20 (m, 1H), 7.11 (m, 1H), 6.30 (s, 1H), 6.02 (s, 1H), 4.02 (m, 1H), 3.85 (m, 2H), 3.45 (m, 2H), 3.35 (m, 1H), 2.83 (s, 3H), 2.70 (s, 3H), 2.20 (m, 2H);
Analysis: C$_{22}$H$_{23}$BrNFO$_8$S.H$_2$O, C, 46.08 (45.68); H, 4.61 (4.35); N, 2.63 (2.42), Br, 14.73 (13.81); S, 4.99 (5.54);
MS (ES+): m/z 465 (M+1), free base.

Example 18

(+)-trans-2-(2,4-Dichloro-5-fluorophenyl)-8-(2-hydroxymethyl-1-methyl-pyrrolidin-3-yl)-5,7-dimethoxy-chromen-4-one Compound of example (7) (0.8 g, 2.58 mmol) in dry DMF (10 mL) was reacted with 2,4-dichloro-5-fluoro-benzoyl chloride (0.887 g, 3.9 mmol) in the presence of NaH (50%, 0.62 g, 12.9 mmol) at 0° C., under nitrogen atmosphere. The reaction mixture was stirred at 25° C. for 2 h. Methanol was added carefully below 20° C. The reaction mixture was poured over crushed ice (100 g), acidified with 1:1 HCl (pH 2) and extracted using EtOAc (2×50 mL). The aqueous layer was basified using a saturated Na$_2$CO$_3$ (pH 10) and extracted using CHCl$_3$ (3×100 mL). The organic layer was dried (anhydrous Na$_2$SO$_4$) and concentrated. To the residue, conc. HCl (10 mL) was added and stirred at room temperature for 2 h. The reaction mixture was poured over crushed ice (100 g) and made basic using a saturated aqueous Na$_2$CO$_3$ solution. The mixture was extracted using CHCl$_3$ (3×100 mL). The organic extract was washed with water, dried (anhydrous Na$_2$SO$_4$) and concentrated to obtain the title compound, (+)-trans-2-(2,4-dichloro-5-fluoro-phenyl)-8-(2-hydroxymethyl-1-methyl-pyrrolidin-3-yl)-5,7-dimethoxy-chromen-4-one.

Yield: 0.54 g (43.4%);
$^1$H NMR (CDCl$_3$, 300 MHz): δ 7.75 (d, 1H), 7.57 (d, 1H), 6.60 (s, 1H), 6.45 (s, 1H), 4.20 (m, 1H), 3.99 (s, 3H), 3.97 (s, 3H), 3.65 (dd, 1H), 3.36 (d, 1H), 3.20 (m, 1H), 2.65 (m, 2H), 2.38 (s, 3H), 2.10 (m, 2H);
MS (ES+): m/z 482 (M+1).

Example 19

(+)-trans-2-(2,4-Dichloro-5-fluorophenyl)-5,7-dihydroxy-8-(2-hydroxymethyl-1-methyl-pyrrolidin-3-yl)-chromen-4-one Molten pyridine hydrochloride (5.5 g, 47.6 mmol) was added to compound of example (18) (0.53 g, 1.1 mmol) and heated at 180° C. for 1.5 h. The reaction mixture was cooled to 25° C., diluted with MeOH (10 mL) and basified using Na$_2$CO$_3$ to pH 10. The mixture was filtered and the organic layer was concentrated. The residue was suspended in water (5 mL), stirred for 30 min., filtered and dried to obtain the compound, (+)-trans-2-(2,4-dichloro-5-fluoro-phenyl)-5,7-dihydroxy-8-(2-hydroxymethyl-1-methylpyrrolidin-3-yl)-chromen-4-one.

Yield: 0.29 g (58%);
IR (KBr): 3422, 1664, 1618, 1401 cm$^{-1}$;
$^1$H NMR (CDCl$_3$+DMSO d$_6$, 300 MHz): δ 7.50 (m, 2H), 6.42 (s, 1H), 6.19 (s, 1H), 4.04 (m, 1H), 3.71 (m, 2H), 3.16 (m, 2H), 2.88 (m, 1H), 2.58 (s, 3H), 2.36 (m, 1H), 1.92 (m, 1H);
MS (ES+): m/z 454 (M+1).

Example 20

(+)-trans-2-(2,4-Dichloro-5-fluorophenyl)-5,7-dihydroxy-8-(2-hydroxymethyl-1-methylpyrrolidin-3-yl)-chromen-4-one hydrochloride Compound of example (19) (0.89 g, 1.96 mmol) was converted to its hydrochloride salt by suspending in IPA (5 mL) and 3.5% HCl (25 mL). The suspension was heated to get a clear solution. The solution was cooled and solid filtered to obtain the compound, (+)-trans-2-(2,4-dichloro-5-fluorophenyl)-5,7-dihydroxy-8-(2-hydroxymethyl-1-methylpyrrolidin-3-yl)-chromen-4-one hydrochloride.

Yield: 0.91 g (92%);
$^1$H NMR (CD$_3$OD, 300 MHz): δ 7.86 (m, 2H), 6.65 (s, 1H), 6.38 (s, 1H), 4.26 (q, 1H), 3.87 (m, 2H), 3.71 (m, 1H), 3.60 (dd, 1H), 3.56 (q, 1H), 2.99 (s, 3H), 2.55 (m, 1H), 2.28 (m, 1H); IR (KBr): 3386, 1657 cm$^{-1}$.
MS (ES+): m/z 454 (M−36.5);
Analysis: C$_{21}$H$_{19}$Cl$_3$FNO$_5$, C, 51.08 (51.35); H, 4.26 (3.87); N, 3.13 (2.85), Cl, 21.99 (21.70).

Example 21

(+)-trans-2-(2,4-Dichloro-5-fluorophenyl)-5,7-dihydroxy-8-(2-hydroxymethyl-1-methylpyrrolidin-3-yl)-chromen-4-one methane sulfonate Methanesulfonic acid (0.012 g, 0.125 mmol) was added to the suspension of compound of example (19) (0.05 g, 0.11 mmol) in methanol (2 mL). It was stirred for 5 min. at 25° C. to obtain clear solution. The solvent was removed under reduced pressure to obtain residue. The residue was washed twice with dry ether (2×5 mL) and dried under high vacuum (0.1 mm) to obtain the compound,(+)-trans-2-(2,4-dichloro-5-fluorophenyl)-5,7-dihydroxy-8-(2-hydroxy methyl-1-methylpyrrolidin-3-yl)-chromen-4-one methane sulfonate.

Yield: 0.054 g (90%);
Analysis: $C_{22}H_{22}Cl_2FNO_8S.2.5H_2O$ C, 44.26 (44.34); H, 4.42 (4.53); N, 2.58 (2.35); Cl, 12.11 (11.92).

Example 22

(+)-trans-2-(2,4-Dichloro-5-fluorophenyl)-5,7-dihydroxy-8-(2-hydroxymethyl-1-methylpyrrolidin-3-yl)-chromen-4-one citrate Citric acid monohydrate (0.023 g, 0.11 mmol) was added to the suspension of compound of example (19) (0.05 g, 0.11 mmol) in methanol (2 mL). It was stirred for 10 min. at 50-55° C. The reaction mixture was concentrated and solid was dried to obtain the compound, (+)-trans-2-(2,4-dichloro-5-fluorophenyl)-5,7-dihydroxy-8-(2-hydroxymethyl-1-methyl-pyrrolidin-3-yl)-chromen-4-one citrate Yield: 0.065 g (91.5%);
Analysis: $C_{27}H_{26}Cl_2FNO_{12}$C, 49.75 (50.17); H, 4.25 (4.05); N, 2.60 (2.17); Cl, 10.69 (10.97).

Example 23

(+)-trans-2-(2,4-Dichloro-5-fluorophenyl)-5,7-dihydroxy-8-(2-hydroxymethyl-1-methylpyrrolidin-3-yl)-chromen-4-one tartarate Tartaric acid (0.016 g, 0.11 mmol) was added to the suspension of compound of example (19) (0.05 g, 0.11 mmol) in methanol (2 mL). It was stirred for 10 min. at 50-55° C. The reaction mixture was concentrated and solid was dried to obtain the compound, (+)-trans-2-(2,4-dichloro-5-fluorophenyl)-5,7-dihydroxy-8-(2-hydroxymethyl-1-methyl-pyrrolidin-3-yl)-chromen-4-one tartarate.

Yield: 0.06 g (90.19%);
Analysis: $C_{25}H_{24}Cl_2FNO_{11}.2.0H_2$C, 47.43 (46.84); H, 4.13 (4.37); N, 2.40 (2.18); Cl, 10.77 (11.08).

Example 24

(+)-trans-2-(2,4-Dichloro-5-fluorophenyl)-5,7-dihydroxy-8-(2-hydroxymethyl-1-methylpyrrolidin-3-yl)-chromen-4-one maleate Maleic acid (0.0127 g, 0.11 mmol) was added to the suspension of compound of example (19) (0.05 g, 0.11 mmol) in methanol (2 mL). It was stirred for 5 min. at 50° C. to get clear solution. The reaction mixture was concentrated and solid was dried to obtain the compound, (+)-trans-2-(2,4-dichloro-5-fluoro-phenyl)-5,7-dihydroxy-8-(2-hydroxymethyl-1-methylpyrrolidin-3-yl)-chromen-4-one maleate.

Yield: 0.059 g (90.19%);
Analysis: $C_{25}H_{22}Cl_2FNO_9.1.5H_2O$ C, 50.54 (50.23); H, 4.08 (4.18); N, 2.31 (2.34); Cl, 11.83 (11.88).

Example 25

(+)-trans-2-(2,4-Dichloro-5-fluorophenyl)-5,7-dihydroxy-8-(2-hydroxymethyl-1-methylpyrrolidin-3-yl)-chromen-4-one acetate Acetic acid (0.0065 mL, 0.0068 g, 0.11 mmol) was added to the suspension of compound of example (19) (0.05 g, 0.11 mmol) in methanol (2 mL). It was stirred for 5 min. at 50-55° C. to get clear solution. The reaction mixture was concentrated and solid was dried to obtain the title compound.

Yield: 0.05 g (88.33%);
Analysis: $C_{23}H_{22}Cl_2FNO_9$C, 53.67 (53.71); H, 4.63 (4.31); N, 3.08 (2.72); Cl, 13.93 (13.79).

Example 26

(+)-trans-2-(2,4-Dichloro-5-fluorophenyl)-5,7-dihydroxy-8-(2-hydroxymethyl-1-methylpyrrolidin-3-yl)-chromen-4-one sulfate $H_2SO_4$ solution (5% methanolic solution, 60 µL, 0.055 mmol) was added to the suspension of compound of example (19) (0.025 g, 0.055 mmol) in methanol (2 mL). It was stirred for 5 min at 50-55° C. The reaction mixture was concentrated and solid was dried to obtain the compound, (+)-trans-2-(2,4-dichloro-5-fluoro phenyl)-5,7-dihydroxy-8-(2-hydroxymethyl-1-methylpyrrolidin-3-yl)-chromen-4-one sulfate.

Yield: 0.025 g (82.24%);
MS (ES−): m/z 550 (M−1).

Example 27

(+)-trans-2-(2,4-Dichloro-5-fluorophenyl)-5,7-dihydroxy-8-(2-hydroxymethyl-1-methylpyrrolidin-3-yl)-chromen-4-one nitrate $HNO_3$ solution (5% methanolic solution, 70 µL, 0.055 mmol) was added to the suspension of compound of example (19) (0.025 g, 0.055 mmol) in methanol (2 mL). It was stirred for 5 min. at 50-55° C. to get clear solution. The reaction mixture was concentrated and solid was dried to obtain the compound, (+)-trans-2-(2,4-dichloro-5-fluorophenyl)-5,7-dihydroxy-8-(2-hydroxymethyl-1-methylpyrrolidin-3-yl)-chromen-4-one nitrate.

Yield: 0.025 g (87.81%);
MS (ES−): m/z 515 (M−1).

Example 28

(+)-trans-2,4-Dichloro-benzoic acid 2-(2-acetoxymethyl-1-methylpyrrolidin-3-yl)-6-acetyl-3,5-dimethoxy-phenyl ester A mixture of the compound of example (6) (3 g, 8.9 mmol), 2,4-dichlorobenzoic acid (1.79 g, 9.3 mmol), DCC (3.87 g, 18.7 mmol) and DMAP (1.148 g, 9.3 mmol) were dissolved in dichloromethane (50 mL) and stirred at room temperature for 12 hrs. The reaction mixture was cooled to 0° C. The precipitated dicyclohexylurea was filtered, the organic layer was concentrated and the residue was purified by column chromatography with 1% methanol in chloroform and 0.01% ammonia as eluent to give the compound, (+)-trans-2,4-dichloro-benzoic acid 2-(2-acetoxymethyl-1-methyl-pyrrolidin-3-yl)-6-acetyl-3,5-dimethoxy-phenyl ester, which was used in further reaction without characterisation.

Yield: 4.48 g (100%)

Example 29

(+)-trans-2-(2,4-Dichlorophenyl)-8-(2-hydroxymethyl-1-methylpyrrolidin-3-yl)-5,7-dimethoxy-chromen-4-one To a solution of n-BuLi (1.6 M in hexane, 10.67 mL, 17 mmol) in THF (25 mL), maintained at 0° C. under nitrogen atmosphere, hexamethyldisilazane (3.56 mL, 17 mmol) was added dropwise and stirred for 15 min. To this, a solution of the compound of example (28)(4.48 g, 8.5 mmol) in THF (25 mL) was added drop wise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8-9. The aqueous layer was extracted with chloroform (3×50 mL). The organic layer was washed with water (25 mL), brine (25 mL) and dried over anhydrous $Na_2SO_4$. The organic layer was concentrated under reduced pressure and dried under vacuum to yield acetic acid 3-{3-[3-(2,4-dichlorophenyl)-3-oxopropionyl]-2-hydroxy-4,6-dimethoxyphenyl}-1-methyl pyrrolidin-2-ylmethyl ester as a brown solid (4.6 g). This ester was dissolved in conc. HCl (50 mL) and stirred for 3 hrs. to effect cyclisation. At the end of 3 hrs, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to yield the compound, (+)-trans-2-(2,4-dichlorophenyl)-8-(2-hydroxymethyl-1-methylpyrrolidin-3-yl)-5,7-dimethoxy-chromen-4-one as a yellow solid.

Yield: 3.2 g (81%);

$^1$H NMR (CDCl$_3$, 300 MHz): δ 7.74 (d, 1H), 7.55 (d, 1H), 7.42 (dd, 1H), 6.56 (s, 1H), 6.47 (s, 1H), 4.2 (m, 1H), 4.02 (s, 3H), 3.99 (s, 3H), 3.68 (dd, 1H), 3.39 (dd, 1H), 3.23 (m, 1H), 2.75 (m, 1H), 2.63 (m, 1H), 2.40 (s, 3H), 2.07 (m, 2H);

MS (ES+): m/z 464 (M+1).

Example 30

(+)-trans-2-(2,4-Dichlorophenyl)-5,7-dihydroxy-8-(2-hydroxymethyl-1-methyl pyrrolidin-3-yl)-chromen-4-one A mixture of the compound of example (29)(3.2 g, 7.35 mmol), pyridine hydrochloride (3.2 g, 6.91 mmol) and a catalytic amount of quinoline was heated at 180° C. for a period of 2.5 hrs. The reaction mixture was diluted with methanol (50 mL) and basified with solid $Na_2CO_3$ to pH 10. The reaction mixture was filtered, and washed with methanol. The organic layer was concentrated and the residue purified by column chromatography using 0.01% ammonia and 3% methanol in chloroform as eluent to yield the compound, (+)-trans-2-(2,4-dichlorophenyl)-5,7-dihydroxy-8-(2-hydroxymethyl-1-methyl pyrrolidin-3-yl)-chromen-4-one, as a yellow solid.

Yield: 0.98 g (30%);

$^1$H NMR (CDCl$_3$, 300 MHz): δ 12.5 (s, 1H), 7.54 (m, 2H), 7.40 (m, 1H), 6.40 (s, 1H), 6.28 (s, 1H), 4.08 (m, 1H), 3.89 (m, 2H), 3.28 (m, 2H), 2.84 (m, 1H), 2.65 (s, 3H), 2.45 (m, 1H), 1.95 (m, 1H);

MS (ES+): m/z 436 (M+1).

Example 31

(+)-trans-2-(2,4-Dichlorophenyl)-5,7-dihydroxy-8-(2-hydroxymethyl-1-methyl pyrrolidin-3-yl)-chromen-4-one hydrochloride The compound of example (30) (0.4 g, 0.9 mmol) was suspended in methanol (2 mL) and treated with ethereal HCl and the organic solvent was evaporated to obtain the compound, (+)-trans-2-(2,4-dichloro-phenyl)-5,7-dihydroxy-8-(2-hydroxymethyl-1-methyl-pyrrolidin-3-yl)-chromen-4-one hydrochloride.

Yield: 0.4 g (92%);

$^1$H NMR (CD$_3$OD, 300 MHz): δ 7.80 (d, 1H), 7.30 (d, 1H), 7.54 (dd, 1H), 6.58 (s, 1H), 6.37 (s, 1H), 4.25 (m, 1H), 3.90 (m, 2H), 3.59 (m, 2H), 3.41 (m, 1H), 2.98 (s, 3H), 2.52 (m, 1H), 2.29 (m, 1H);

MS (ES−): m/z 470 (M−1).

Example 32

(+)-trans-4-Bromo-2-chlorobenzoic acid 2-(2-acetoxymethyl-1-methyl-pyrrolidin-3-yl)-6-acetyl-3,5-dimethoxyphenyl ester A mixture of the compound of example (6)(1.95 g, 5.5 mmol), 4-bromo-2-chlorobenzoic acid (1.44 g, 6.1 mmol), DCC (2.29 g, 11 mmol) and DMAP (0.68 g, 5.5 mmol) were dissolved in dichloromethane (50 mL) and stirred at room temperature for 12 hrs. The reaction mixture was cooled to 0° C., the precipitated dicyclohexylurea was filtered and the organic layer concentrated and residue purified by column chromatography with 1% methanol in chloroform and 0.01% ammonia as eluent to give the compound, (+)-trans-4-bromo-2-chlorobenzoic acid 2-(2-acetoxymethyl-1-methyl-pyrrolidin-3-yl)-6-acetyl-3,5-dimethoxy-phenyl ester Yield: 2.8 g (88.7%);

MS (ES+): m/z 569 (M+1).

Example 33

(+)-trans-2-(4-Bromo-2-chloro-phenyl)-8-(2-hydroxymethyl-1-methylpyrrolidin-3-yl)-5,7-dimethoxy-chromen-4-one To a solution of n-BuLi (15% solution in hexane, 4.23 mL, 10 mmol) in THF (25 mL), maintained at 0° C. under nitrogen atmosphere, hexamethyldisilazane (2.1 mL, 10 mmol) was added dropwise and stirred for 15 min. To this, a solution of the compound of example (32)(2.8 g, 5 mmol) in THF (25 mL) was added drop wise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8-9. The aqueous layer was extracted with chloroform (3×50 mL). The organic layer was washed with water (25 mL), brine (25 mL) and dried over anhydrous $Na_2SO_4$. The organic layer was concentrated under reduced pressure and dried under vacuum to yield acetic acid 3-{3-[3-(4-bromo-2-chloro-phenyl)-3-oxo-propionyl]-2-hydroxy-4,6-dimethoxy-phenyl}-1-methyl-pyrrolidin-2-ylmethyl ester as a brown solid (2.65 g). This ester was dissolved in conc. HCl (20 mL) and stirred for 3 hrs. to effect cyclisation. At the end of 3 hrs, the reaction mixture was basified with solid $NaHCO_3$ to pH 8-9. The aqueous layer was extracted with chloroform (50×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.01% ammonia as eluent to yield the compound, (+)-trans-2-(4-bromo-2-chloro-phenyl)-8-(2-hydroxymethyl-1-methylpyrrolidin-3-yl)-5,7-dimethoxy-chromen-4-one, as a yellow solid.

Yield: 1.4 g (59%);
$^1$H NMR (CDCl$_3$, 300 MHz): δ 7.69 (d, 1H), 7.66 (d, 1H), 7.55 (dd, 1H), 6.55 (s, 1H), 6.45 (s, 1H), 4.19 (m, 1H), 4.00 (s, 3H), 3.98 (s, 3H), 3.66 (dd, 1H), 3.38 (m, 1H), 3.23 (m, 1H), 2.75 (m, 1H), 2.63 (m, 1H), 2.40 (s, 3H), 2.10 (m, 2H);
MS (ES+): m/z 509 (M+1).

Example 34

(+)-trans-2-(4-Bromo-2-chlorophenyl)-5,7-dihydroxy-8-(2-hydroxymethyl-1-methylpyrrolidin-3-yl)-chromen-4-one A mixture of the compound of example (33)(1.4 g, 2.75 mmol), pyridine hydrochloride (1.4 g, 12 mmol) and a catalytic amount of quinoline was heated at 180° C. for a period of 2.5 hrs. The reaction mixture was diluted with methanol (50 mL) and basified with solid Na$_2$CO$_3$ to pH 10. The reaction mixture was filtered, and washed with methanol. The organic layer was concentrated and the residue purified by column chromatography using 0.01% ammonia and 3% methanol in chloroform as eluent to yield the compound, (+)-trans-2-(4-bromo-2-chlorophenyl)-5,7-dihydroxy-8-(2-hydroxymethyl-1-methyl-pyrrolidin-3-yl)-chromen-4-one, as a yellow solid.

Yield: 0.88 g (60.6%);
$^1$H NMR (CDCl$_3$, 300 MHz): δ 7.91 (m, 1H), 7.87 (m, 1H), 7.69 (m, 1H), 6.41 (s, 1H), 6.15 (s, 1H), 4.03 (m, 1H), 3.77 (dd, 1H), 3.66 (dd, 1H), 3.47 (m, 1H), 3.33 (m, 1H), 3.18 (m, 1H), 2.76 (s, 3H), 2.24 (m, 2H);
MS (ES+): m/z 481 (M+1).

Example 35

(+)-trans-2-(4-Bromo-2-chlorophenyl)-5,7-dihydroxy-8-(2-hydroxymethyl-1-methylpyrrolidin-3-yl)-chromen-4-one hydrochloride The compound of example (34) (0.48 g, 1.0 mmol) was suspended in methanol (2 mL) and treated with ethereal HCl and the organic solvent evaporated to obtain the compound, (+)-trans-2-(4-bromo-2-chlorophenyl)-5,7-dihydroxy-8-(2-hydroxymethyl-1-methylpyrrolidin-3-yl)-chromen-4-one hydrochloride.

Yield: 0.4 g (93%);
$^1$H NMR (CD$_3$OD, 300 MHz): δ 7.87 (m, 1H), 7.71 (m, 2H), 6.58 (s, 1H), 6.38 (s, 1H), 4.28 (m, 1H), 3.90 (m, 2H), 3.73 (m, 1H), 3.59 (m, 1H), 3.45 (m, 1H), 2.99 (s, 3H), 2.58 (m, 1H), 2.28 (m, 1H);
MS (ES−): m/z 515 (M−1).

Example 36

(+)-trans-2-Chloro-4-cyano-benzoic acid 2-(2-acetoxymethyl-1-methylpyrrolidin-3-yl)-6-acetyl-3,5-dimethoxy-phenyl ester A mixture of the compound of example (6)(3.84 g, 10 mmol), 2-chloro-4-cyano-benzoic acid (2.48 g, 13 mmol), DCC (4.51 g, 21 mmol) and DMAP (1.34 g, 10 mmol) were dissolved in dichloromethane (50 mL) and stirred at room temperature for 12 hrs. The reaction mixture is cooled to 0° C., the precipitated dicyclohexylurea was filtered and the organic layer concentrated and the residue purified by column chromatography with 1% methanol in chloroform and 0.01% ammonia as eluent to give the compound, (+)-trans-2-chloro-4-cyanobenzoic acid 2-(2-acetoxymethyl-1-methylpyrrolidin-3-yl)-6-acetyl-3,5-dimethoxyphenyl ester.

Yield: 3.5 g (62%);
$^1$H NMR (CDCl$_3$, 300 MHz): δ 8.19 (d, 1H), 7.79 (s, 1H), 7.69 (d, 1H), 6.45 (s, 1H), 4.10 (m, 1H), 3.93 (s, 6H), 3.48 (m, 2H), 3.11 (m, 1H), 2.72 (m, 1H), 2.48 (s, 3H), 2.35 (s, 3H), 2.10 (m, 1H), 1.92 (m, 2H), 1.74 (s, 3H);
MS (ES+): m/z 515 (M+1).

Example 37

(+)-trans-2-(2-Chloro-4-cyano-phenyl)-8-(2-hydroxymethyl-1-methyl-pyrrolidin-3-yl)-5,7-dimethoxy-chromen-4-one To a solution of n-BuLi (1.6 M solution in hexane, 17 mL, 27 mmol) in THF (50 mL), maintained at 0° C. under nitrogen atmosphere, hexamethyldisilazane (5.7 mL, 27 mmol) was added dropwise and stirred for 15 min. To this, a solution of the compound of example (36)(5.6 g, 10 mmol) in THF (50 mL) was added drop wise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8-9. The aqueous layer was extracted with chloroform (3×75 mL). The organic layer was washed with water (50 mL), brine (50 mL) and dried over anhydrous Na$_2$SO$_4$. The organic layer was concentrated under reduced pressure and dried under vacuum to yield acetic acid 3-{3-[3-(2-chloro-4-cyano-phenyl)-3-oxo-propionyl]-2-hydroxy-4,6-dimethoxy-phenyl}-1-methyl-pyrrolidin-2-ylmethyl ester as oil (6.1 g). This ester was dissolved in conc. HCl (60 mL) and stirred for 3 hrs. to effect cyclisation. At the end of 3 hrs, the reaction mixture was basified with solid NaHCO$_3$ to pH 8-9. The aqueous layer was extracted with chloroform (50×3 mL) and washed with water (25 mL) and brine (25 mL). The organic layer was dried over anhydrous Na$_2$SO$_4$, concentrated under reduced pressure and dried over vacuum. The residue was purified by column chromatography with 3% methanol in chloroform and 0.01% ammonia as eluent to yield the compound, (+)-trans-2-(2-chloro-4-cyano-phenyl)-8-(2-hydroxymethyl-1-methyl-pyrrolidin-3-yl)-5,7-dimethoxy-chromen-4-one, as a yellow solid.

Yield: 0.75 g (15%);
IR (KBr): 3431, 2233, 1648, 1599 cm$^{-1}$,
$^1$H NMR (CDCl$_3$, 300 MHz): δ 8.20 (d, 1H), 8.04 (s, 1H), 7.88 (d, 1H), 6.65 (s, 1H), 6.46 (s, 1H), 4.25 (m, 1H), 4.01 (s, 3H), 3.99 (s, 3H), 3.70 (m, 1H), 3.35 (m, 2H), 2.75 (m, 2H), 2.43 (s, 3H), 2.10 (m, 2H);
MS (ES+): m/z 455 (M+1).

Example 38

(+)-trans-2-(2-Chloro-4-cyano-phenyl)-8-(2-hydroxymethyl-1-methyl-pyrrolidin-3-yl)-5,7-dimethoxy-chromen-4-one hydrochloride The compound of example (37) (20 mg, 0.046 mmol) was suspended in methanol (2 mL) and treated with ethereal HCl and the organic solvent evaporated to get the compound, (+)-trans-2-(2-chloro-4-cyano-phenyl)-8-(2-hydroxymethyl-1-methyl-pyrrolidin-3-yl)-5,7-dimethoxy-chromen-4-one hydrochloride.

Yield: 20 mg (98%);
$^1$H NMR (CD$_3$OD, 300 MHz): δ 8.08 (m, 1H), 7.97 (m, 1H), 7.86 (m, 1H), 6.78 (s, 1H), 6.58 (s, 1H), 4.32 (m, 1H), 4.10 (s, 3H), 4.01 (s, 3H), 3.84 (m, 2H), 3.75 (m, 1H), 3.57 (m, 1H), 3.41 (m, 1H), 2.98 (s, 3H), 2.43 (m, 1H), 2.31 (m, 1H);
MS (ES−): m/z 489 (M−1).

Example 39

(+)-trans-2-(2-Chloro-4-cyanophenyl)-5,7-dihydroxy-8-(2-hydroxymethyl-1-methylpyrrolidin-3-yl)-chromen-4-one A mixture of the compound of example (37)(0.25 g, 0.55 mmol), pyridine hydrochloride (0.25 g, 2.2 mmol) and a catalytic amount of quinoline was heated at 180° C. for a period of 2.5 hrs. The reaction mixture was diluted with methanol (50 mL) and basified with solid $Na_2CO_3$ to pH 10. The reaction mixture was filtered, and washed with methanol. The organic layer was concentrated and the residue purified by column chromatography using 0.01% ammonia and 4.5% methanol in chloroform as eluent to yield the compound, (+)-trans-2-(2-chloro-4-cyanophenyl)-5,7-dihydroxy-8-(2-hydroxymethyl-1-methyl-pyrrolidin-3-yl)-chromen-4-one, as a yellow solid.
Yield: 0.11 g (49.5%);
IR (KBr): 3396, 2234, 1656, 1615 $cm^{-1}$;
$^1$H NMR ($CD_3OD$, 300 MHz): δ 8.05 (s, 1H), 7.90 (m, 2H), 6.45 (s, 1H), 6.11 (s, 1H), 4.02 (m, 1H), 3.75 (dd, 2H), 3.49 (m, 2H), 3.21 (m, 1H), 2.76 (s, 3H), 2.23 (m, 2H);
MS (ES+): m/z 427 (M+1)

Example 40

(+)-trans-2-(2-Chloro-4-cyanophenyl)-5,7-dihydroxy-8-(2-hydroxymethyl-1-methylpyrrolidin-3-yl)-chromen-4-one hydrochloride The compound of example (39)(0.1 g, 0.23 mmol) was suspended in methanol (2 mL) and treated with ethereal HCl and the organic solvent evaporated to obtain the compound, (+)-trans-2-(2-chloro-4-cyanophenyl)-5,7-dihydroxy-8-(2-hydroxymethyl-1-methylpyrrolidin-3-yl)-chromen-4-one hydrochloride.
Yield: 0.1 g (92.6%);
MS (ES−): m/z 461 (M−1).

Example 41

(+)-trans-2-Chloro-4-trifluoromethylbenzoic acid 2-(2-acetoxymethyl-1-methyl-pyrrolidin-3-yl)-6-acetyl-3,5-dimethoxyphenyl ester A mixture of the compound of example (6) (1.16 g, 3.2 mmol), 2-chloro-4-trifluoromethylbenzoic acid (0.88 g, 4 mmol), DCC (1.35 g, 6.5 mmol) and DMAP (0.4 g, 3.27 mmol) were dissolved in dichloromethane (50 mL) and stirred at room temperature for 12 hrs. The reaction mixture is cooled to 0° C., the precipitated dicyclohexylurea was filtered and the organic layer concentrated and residue purified by column chromatography with 1% methanol in chloroform and 0.01% ammonia as eluent to obtain the compound, (+)-trans-2-chloro-4-trifluoromethylbenzoic acid 2-(2-acetoxymethyl-1-methyl-pyrrolidin-3-yl)-6-acetyl-3,5-dimethoxyphenyl ester.
Yield: 1.44 g (78.8%);
$^1$H NMR ($CDCl_3$, 300 MHz): δ 8.19 (d, 1H), 7.79 (s, 1H), 7.69 (d, 1H), 6.45 (s, 1H), 4.14 (m, 1H), 3.93 (s, 6H), 3.52 (m, 1H), 3.17 (m, 1H), 2.63 (m, 1H), 2.48 (s, 3H), 2.41 (s, 3H), 2.15 (m, 1H), 2.05 (m, 1H), 1.81 (s, 3H), 1.62 (m, 2H);
MS (ES+): m/z 558 (M+1).

Example 42

(+)-trans-2-(2-Chloro-4-trifluoromethylphenyl)-8-(2-hydroxymethyl-1-methyl pyrrolidin-3-yl)-5,7-dimethoxy-chromen-4-one To a solution of n-BuLi (15% solution in hexane, 2.2 mL, 5 mmol) in THF (10 mL), maintained at 0° C. under nitrogen atmosphere, hexamethyldisilazane (1.08 mL, 5.1 mmol) was added dropwise and stirred for 15 min. To this, a solution of the compound of example (41)(1.44 g, 2.5 mmol) in THF (10 mL) was added dropwise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8 to 9. The aqueous layer was extracted with chloroform (3×25 mL). The organic layer was washed with water (25 mL), brine (25 mL) and dried over anhydrous $Na_2SO_4$. The organic layer was concentrated under reduced pressure and dried under vacuum to yield acetic acid 3-{3-[3-(2-chloro-4-trifluoromethyl-phenyl)-3-oxo-propionyl]-2-hydroxy-4,6-dimethoxy-phenyl}-1-methyl-pyrrolidin-2-yl-methyl ester as an oil (1.3 g, 90.2%). This ester was dissolved in conc. HCl (10 mL) and stirred for 3 hrs. to effect cyclisation. At the end of 3 hrs, the reaction mixture was basified with solid $NaHCO_3$ to pH 8 to 9. The aqueous layer was extracted with chloroform (25×3 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.1% ammonia as eluent to yield the compound, (+)-trans-2-(2-chloro-4-trifluoromethylphenyl)-8-(2-hydroxymethyl-1-methyl pyrrolidin-3-yl)-5,7-dimethoxy-chromen-4-one as a yellow solid.
Yield: 0.56 g (48.2%);
$^1$H NMR ($CDCl_3$, 300 MHz): δ 7.95 (d, 1H), 7.78 (s, 1H), 7.69 (d, 1H), 6.61 (s, 1H), 6.46 (s, 1H), 4.21 (m, 1H), 4.01 (s, 3H), 3.93 (s, 3H), 3.71 (dd, 1H), 3.41 (d, 1H), 3.26 (m, 1H), 2.84 (m, 1H), 2.70 (m, 1H), 2.44 (s, 3H), 2.10 (m, 2H);
MS (ES+): m/z 497 (M+1).

Example 43

(+)-trans-2-(2-Chloro-4-trifluoromethyl-phenyl)-5,7-dihydroxy-8-(2-hydroxy-methyl-1-methylpyrrolidin-3-yl)-chromen-4-one A mixture of the compound of example (42) (0.25 g, 0.5 mmol), pyridine hydrochloride (0.25 g, 2.16 mmol) and a catalytic amount of quinoline was heated at 180° C. for a period of 2.5 hrs. The reaction mixture was diluted with methanol (25 mL) and basified with solid $Na_2CO_3$ to pH 10. The reaction mixture was filtered, and washed with methanol. The organic layer was concentrated and the residue purified by column chromatography using 0.1% ammonia and 4.5% methanol in chloroform as eluent to yield the compound, (+)-trans-2-(2-chloro-4-trifluoromethylphenyl)-5,7-dihydroxy-8-(2-hydroxy-methyl-1-methylpyrrolidin-3-yl)-chromen-4-one, as a yellow solid.
Yield: 0.15 g (63.7%);
$^1$H NMR ($CDCl_3$, 300 MHz): δ 7.99 (m, 2H), 7.83 (d, 1H), 6.65 (s, 1H), 6.41 (s, 1H), 4.24 (m, 1H), 3.90 (m, 2H), 3.70 (m, 1H), 3.60 (m, 1H), 3.41 (m, 1H), 2.99 (s, 3H), 2.54 (m, 1H), 2.28 (m, 1H);
MS (ES+): m/z 470 (M+1).

Example 44

(+)-trans-2-(2-Chloro-4-trifluoromethylphenyl)-5,7-dihydroxy-8-(2-hydroxy-methyl-1-methylpyrrolidin-3-yl)-chromen-4-one hydrochloride The compound of example (43) (0.1 g, 0.2 mmol) suspended in methanol (2 mL) and treated with ethereal HCl and the organic solvent evaporated to yield the compound, (+)-trans-2-(2-chloro-4-trifluoromethyl-phenyl)-5,7-dihydroxy-8-(2-hydroxymethyl-1-methyl-pyrrolidin-3-yl)-chromen-4-one hydrochloride.
Yield: 0.1 g (92.8%);
$^1$H NMR (CDCl$_3$, 300 MHz): δ 8.02 (d, 2H), 7.83 (d, 1H), 6.64 (s, 1H), 6.41 (s, 1H), 4.23 (m, 1H), 3.73 (m, 2H), 3.68 (m, 1H), 3.51 (m, 1H), 3.39 (m, 1H), 2.99 (s, 3H), 2.54 (m, 1H), 2.31 (m, 1H).

Example 45

(+)-trans-2-Chloro-4-nitro-benzoic acid 2-(2-acetoxymethyl-1-methyl-pyrrolidin-3-yl)-6-acetyl-3,5-dimethoxyphenyl ester 2-Chloro-4-nitro-benzoic acid (13 g, 64 mmol) and thionyl chloride (40 mL) were heated together at 85° C. for 3 hrs. Excess thionyl chloride was evaporated under reduced pressure and the residue was dried in vacuum and dissolved in THF (100 mL). This was added dropwise to a solution of the compound of example (6)(15 g, 42 mmol) and triethylamine (29.5 mL, 213 mmol) in THF (100 mL) maintained at 15-20° C. The reaction mixture was allowed to warm to room temperature and was stirred for 12 hrs. At the end of 12 hrs., the reaction mixture was concentrated to remove THF, acidified with dilute HCl, basified with 10% NaHCO$_3$ solution to pH 10, extracted with EtOAc (3×100 mL), washed with water (50 mL), brine (50 mL) and the organic layer dried over anhydrous Na$_2$SO$_4$. The organic layer was concentrated under reduced pressure to obtain the compound, (+)-trans-2-chloro-4-nitro-benzoic acid 2-(2-acetoxymethyl-1-methyl-pyrrolidin-3-yl)-6-acetyl-3,5-dimethoxyphenyl ester, as an oil which was utilized as such for further reaction without purification.
Yield: 24.8 g (71.7%);
$^1$H NMR (CDCl$_3$, 300 MHz): δ 8.35 (s, 1H), 8.25 (m, 2H), 6.47 (s, 1H), 4.17 (m, 1H), 3.94 (s, 6H), 3.59 (m, 1H), 3.17 (m, 1H), 2.80 (m, 1H), 2.49 (s, 6H), 2.46 (m, 2H), 2.17 (m, 1H), 1.95 (m, 1H), 1.83 (s, 3H);
MS (ES+): m/z 535 (M+1).

Example 46

(+)-trans-2-(2-Chloro-4-nitrophenyl)-8-(2-hydroxymethyl-1-methyl-pyrrolidin-3-yl)-5,7-dimethoxy-chromen-4-one A solution of the compound of example (45)(20 g, 37.5 mmol) in dioxane (150 mL) was added dropwise to a suspension of sodium hydride (60% dispersion, 5.68 g, 142 mmol) in dioxane (50 mL) and the reaction mixture stirred at room temperature for 12 hrs. The reaction mixture was quenched with dropwise addition of methanol and the solvents evaporated under reduced pressure. The residue was acidified with dilute HCl, basified with 10% NaHCO$_3$ solution to pH 8 to 9 and extracted with EtOAc (3×250 mL). The organic layer was washed with water (50 mL), brine (50 mL), dried over anhydrous Na$_2$SO$_4$ and concentrated under reduced pressure to give acetic acid 3-{3-[3-(2-chloro-4-nitrophenyl)-3-oxopropionyl]-2-hydroxy-4,6-dimethoxyphenyl}-1-methyl-pyrrolidin-2-ylmethyl ester as an oil (18.2 g). This ester was dissolved in conc. HCl (50 mL) and stirred at room temperature for 3 hrs. At the end of 3 hrs, the reaction mixture was basified with solid NaHCO$_3$ to pH 8 to 9. The aqueous layer was extracted with chloroform (3×250 mL) and washed with water (50 mL) and brine (50 mL). The organic layer was dried over anhydrous Na$_2$SO$_4$, concentrated under reduced pressure and dried over vacuum. The residue was purified by column chromatography with 3% methanol in chloroform and 0.1% ammonia as eluent to yield the compound (+)-trans-2-(2-chloro-4-nitrophenyl)-8-(2-hydroxymethyl-1-methylpyrrolidin-3-yl)-5,7-dimethoxy-chromen-4-one as a pale yellow solid.
Yield: 9.5 g (53.5%);
IR (KBr): 3447, 1648, 1600, 1570 cm$^{-1}$;
$^1$H NMR (CDCl$_3$, 300 MHz): δ 8.37 (d, 1H), 8.26 (dd, 1H), 8.09 (d, 1H), 6.67 (s, 1H), 6.46 (s, 1H), 4.18 (m, 1H), 4.01 (s, 3H), 3.98 (s, 3H), 3.67 (m, 1H), 3.32 (m, 1H), 3.19 (m, 1H), 2.62 (m, 2H), 2.36 (s, 3H), 2.04 (m, 2H);
MS (ES+): m/z 475 (M+1).

Example 47

(+)-trans-2-(2-Chloro-4-nitrophenyl)-8-(2-hydroxymethyl-1-methyl-pyrrolidin-3-yl)-5,7-dimethoxy-chromen-4-one hydrochloride The compound of example (46) (0.05 g, 0.105 mmol) was suspended in methanol (2 mL) and treated with ethereal HCl and the organic solvent evaporated to obtain the compound, (+)-trans-2-(2-chloro-4-nitrophenyl)-8-(2-hydroxymethyl-1-methyl-pyrrolidin-3-yl)-5,7-dimethoxy-chromen-4-one hydrochloride.
Yield: 0.05 g (53.7%); $^1$H NMR (CD$_3$OD, 300 MHz): δ 8.50 (d, 1H), 8.27 (dd, 1H), 8.09 (d, 1H), 6.79 (s, 1H), 6.62 (s, 1H), 4.28 (m, 1H), 4.11 (s, 3H), 4.02 (s, 3H), 3.88 (m, 2H), 3.72 (m, 1H), 3.50 (m, 2H), 2.99 (s, 3H), 2.49 (m, 1H), 2.26 (m, 1H); MS (ES+): m/z 511 (M+1).

Example 48

(+)-trans-2-(2-Chloro-4-nitrophenyl)-8-(2-hydroxymethyl-1-methyl-pyrrolidin-3-yl)-5,7-dimethoxy-chromen-4-one gluconate The compound of example (46) (6.4 g, 13.4 mmol) was suspended in methanol (300 mL) and treated with gluconic acid (2.63 g, 13.4 mmol) and the organic solvent evaporated to obtain the compound, (+)-trans-2-(2-chloro-4-nitro phenyl)-8-(2-hydroxymethyl-1-methyl-pyrrolidin-3-yl)-5,7-dimethoxy-chromen-4-one gluconate.
Yield: 8.5 g (93.9%);
m.p.: 137-140° C.;
IR (KBr): 3404, 1648, 1601, 1524 cm$^{-1}$;
$^1$H NMR (CD$_3$OD, 300 MHz): δ 8.50 (d, 1H), 8.33 (dd, 1H), 8.09 (d, 1H), 6.78 (s, 1H), 6.61 (s, 1H), 4.31 (m, 1H), 4.15 (s, 3H), 4.01 (s, 3H), 3.72 (m, 11H), 2.95 (s, 3H), 2.4 (m, 1H), 2.30 (m, 1H); $[α]_D^{25}$: +11.76° (c=0.76, MeOH);
MS (ES+): m/z 475 (M+1), Free base.

Example 49

(+)-trans-2-(2-Chloro-4-nitrophenyl)-5,7-dihydroxy-8-(2-hydroxymethyl-1-methylpyrrolidin-3-yl)-chromen-4-one A mixture of the compound of example (46) (4.2 g, 8.8 mmol), pyridine hydrochloride (4.2 g, 36 mmol) and a catalytic amount of quinoline was heated at 180° C. for a period of 2 hrs. The reaction mixture was cooled and diluted with methanol (50 mL) and basified with solid $Na_2CO_3$ to pH 10. The reaction mixture was filtered, and washed with methanol. The organic layer was concentrated and the residue purified by column chromatography using 0.1% ammonia and 3% methanol in chloroform as eluent to yield the compound, (+)-trans-2-(2-chloro-4-nitro-phenyl)-5,7-dihydroxy-8-(2-hydroxymethyl-1-methylpyrrolidin-3-yl)-chromen-4-one as a yellow solid.

Yield: 2.8 g (70.88%);
$^1$H NMR (CDCl$_3$, 300 MHz): δ 8.48 (d, 1H), 8.34 (dd, 1H), 8.02 (d, 1H), 6.48 (s, 1H), 6.12 (s, 1H), 4.03 (m, 1H), 3.74 (m, 2H), 3.64 (m, 1H), 3.60 (m, 1H), 3.22 (m, 1H), 2.77 (s, 3H), 2.22 (m, 2H);
MS (ES+): m/z 447 (M+1).

Example 50

(+)-trans-2-(2-Chloro-4-nitrophenyl)-5,7-dihydroxy-8-(2-hydroxymethyl-1-methylpyrrolidin-3-yl)-chromen-4-one hydrochloride The compound of example (49) (2.8 g, 6.2 mmol) was suspended in methanol (10 mL) and treated with ethereal HCl and the organic solvent evaporated to obtain the compound, (+)-trans-2-(2-chloro-4-nitrophenyl)-5,7-dihydroxy-8-(2-hydroxymethyl-1-methylpyrrolidin-3-yl)-chromen-4-one hydrochloride.

Yield: 2.7 g (92.5%);
$^1$H NMR (CD$_3$OD, 300 MHz): δ 8.51 (d, 1H), 8.36 (dd, 1H), 8.09 (d, 1H), 6.69 (s, 1H), 6.41 (s, 1H), 4.25 (m, 1H), 3.91 (m, 2H), 3.73 (m, 1H), 3.70 (m, 1H), 3.63 (m, 1H), 3.00 (s, 3H), 2.55 (m, 1H), 2.32 (m, 1H);
MS (ES+): m/z 483 (M+1);
$[α]_D^{25}$: +13.0° (c=0.2, methanol).

Example 51

(+)-trans-2-(4-Amino-2-chlorophenyl)-8-(2-hydroxymethyl-1-methyl-pyrrolidin-3-yl)-5,7-dimethoxy-chromen-4-one The compound of example (46) (1.0 g, 2.1 mmol), stannous chloride (1.9 g, 8.4 mmol) and EtOAc (5 mL) were stirred together at room temperature for 12 hrs.

At the end of 12 hrs., the reaction mixture was basified with 10% NaOH solution to pH 10 and extracted with EtOAc (3×10 mL). The organic layers were combined, washed with water (10 mL), brine (10 mL), dried over anhydrous Na$_2$SO4 and concentrated under reduced pressure to yield the compound, (+)-trans-2-(4-amino-2-chlorophenyl)-8-(2-hydroxymethyl-1-methyl-pyrrolidin-3-yl)-5,7-dimethoxy-chromen-4-one, as a solid.

Yield: 0.74 g (79%);
MS (ES+): 445 (M+1).

Example 52

(+)-trans-2-(4-Amino-2-chlorophenyl)-5,7-dihydroxy-8-(2-hydroxymethyl-1-methylpyrrolidin-3-yl)-chromen-4-one (Compound-1)

(+)-trans-2-(2-Chloro-4-methylaminophenyl)-5,7-dihydroxy-8-(2-hydroxymethyl-1-methylpyrrolidin-3-yl)-chromen-4-one (Compound-2)

A mixture of the compound of example (51)(0.7 g, 1.57 mmol), pyridine hydrochloride (0.7 g, 6 mmol) and a catalytic amount of quinoline was heated at 180° C. for a period of 2.5 hrs. The reaction mixture was cooled and diluted with methanol (25 mL) and basified with solid $Na_2CO_3$ to pH 10. The reaction mixture was filtered, and washed with methanol. The organic layer was concentrated and the residue purified by column chromatography using 0.1% ammonia and 3% methanol in chloroform as eluent to yield the compounds, (+)-trans-2-(4-amino-2-chlorophenyl)-5,7-dihydroxy-8-(2-hydroxymethyl-1-methylpyrrolidin-3-yl)-chromen-4-one (Compound-1) and (+)-trans-2-(2-chloro-4-methylaminophenyl)-5,7-dihydroxy-8-(2-hydroxymethyl-1-methyl-pyrrolidin-3-yl)-chromen-4-one (Compound-2) as yellow solids.

Compound-1: Yield: 0.25 g (38%); MS (ES+): 417 (M+1)
Compound-2: Yield: 0.13 g (19%); MS (ES+): 431 (M+1).

Example 53

(+)-trans-2-(4-Amino-2-chlorophenyl)-5,7-dihydroxy-8-(2-hydroxymethyl-1-methylpyrrolidin-3-yl)-chromen-4-one hydrochloride The compound (+)-trans-2-(4-Amino-2-chlorophenyl)-5,7-dihydroxy-8-(2-hydroxymethyl-1-methylpyrrolidin-3-yl)-chromen-4-one (0.25 g, 0.6 mmol) was suspended in methanol (2 mL) and treated with ethereal HCl and the organic solvent evaporated to yield the compound, (+)-trans-2-(4-amino-2-chloro phenyl)-5,7-dihydroxy-8-(2-hydroxymethyl-1-methylpyrrolidin-3-yl)-chromen-4-one hydrochloride.

Yield: 0.26 g (96%);
$^1$H NMR (CD$_3$OD, 300 MHz): δ 7.78 (d, 1H), 7.26 (d, 1H), 7.13 (dd, 1H), 6.56 (s, 1H), 6.36 (s, 1H), 4.30 (m, 1H), 3.91 (m, 2H), 3.80 (m, 1H), 3.60 (dd, 1H), 3.46 (m, 1H), 3.00 (s, 3H), 2.52 (m, 1H), 2.29 (m, 1H);
MS (ES+): 417 (M+1), free base; MS (ES−): 451 (M−1).

Example 54

(+)-trans-2-(2-Chloro-4-methylaminophenyl)-5,7-dihydroxy-8-(2-hydroxymethyl-1-methylpyrrolidin-3-yl)-chromen-4-one hydrochloride The compound, (+)-trans-2-(2-Chloro-4-methylaminophenyl)-5,7-dihydroxy-8-(2-hydroxymethyl-1-methyl-pyrrolidin-3-yl)-chromen-4-one (0.13 g, 0.3 mmol) was suspended in methanol (2 mL) and treated with ethereal HCl and the organic solvent evaporated to obtain the salt, (+)-trans-2-(2-chloro-4-methylaminophenyl)-5,7-dihydroxy-8-(2-hydroxymethyl-1-methyl-pyrrolidin-3-yl)-chromen-4-one hydrochloride.

Yield: 0.13 g (96%);
$^1$H NMR (CD$_3$OD, 300 MHz): δ 7.67 (d, 1H), 6.86 (d, 1H), 6.80 (dd, 1H), 6.54 (s, 1H), 6.34 (s, 1H), 4.32 (m, 1H), 3.94

(m, 2H), 3.64 (m, 1H), 3.58 (dd, 1H), 3.44 (m, 1H), 3.00 (s, 3H), 2.86 (s, 3H), 2.53 (m, 1H), 2.33 (m, 1H),
MS (ES+): 431 (M+1), free base MS (ES−): 465 (M−1).

Example 55

(+)-trans-2-Chloro-4-pyrrolidin-1-yl-benzoic acid 2-(2-acetoxymethyl-1-methyl-pyrrolidin-3-yl)-6-acetyl-3,5-dimethoxyphenyl ester 2-Chloro-4-pyrrolidin-1-yl-benzoic acid (1.0 g, 4.4 mmol), thionyl chloride (0.35 mL, 4.8 mmol), N-methylpyrrolidin-2-one (0.1 mL) and dichloromethane (20 mL) were stirred together at room temperature for 12 hrs. To this solution, the compound of example (6)(0.86 g, 2.4 mmol) was added and the mixture cooled to 0 to 5° C. After cooling, triethylamine (1.7 mL, 12.7 mmol) was added and the reaction mixture was allowed to warm to room temperature and stirred for 4 hrs. The mixture was diluted with chloroform (25 mL), washed with 10% NaHCO$_3$ (10 mL), water (10 mL), brine (10 mL) and the organic layer dried over anhydrous Na$_2$SO$_4$. The organic layer was concentrated under reduced pressure to yield the compound, (+)-trans-2-chloro-4-pyrrolidin-1-ylbenzoic acid 2-(2-acetoxymethyl-1-methyl-pyrrolidin-3-yl)-6-acetyl-3,5-dimethoxyphenyl ester as a solid which was utilized as such for further reaction without purification.
Yield: 1.37 g (100%);
MS (ES+): 559 (M+1).

Example 56

(+)-trans-2-(2-Chloro-4-pyrrolidin-1-yl-phenyl)-8-(2-hydroxymethyl-1-methyl-pyrrolidin-3-yl)-5,7-dimethoxy-chromen-4-one To a solution of n-BuLi (1.6 M in hexane, 3 mL, 4.8 mmol) in THF (10 mL), maintained at 0° C. under nitrogen atmosphere, hexamethyldisilazane (1 mL, 4.75 mmol) was added dropwise and stirred for 15 min. To this, a solution of the compound of example (55)(1.37 g, 2.45 mmol) in THF (5 mL) was added drop wise, maintaining the temperature at 0° C. After the addition, the reaction mixture was allowed to warm to room temperature and stirred for 2.5 hrs. The reaction mixture was acidified with dilute HCl, and basified with 10% sodium bicarbonate to pH 8-9. The aqueous layer was extracted with chloroform (3×50 mL). The organic layer was washed with water (25 mL), brine (25 mL) and dried over anhydrous Na$_2$SO$_4$. The organic layer was concentrated under reduced pressure and dried under vacuum to yield acetic acid 3-{3-[3-(2-chloro-4-pyrrolidin-1-yl-phenyl)-3-oxo-propionyl]-2-hydroxy-4,6-dimethoxy-phenyl}-1-methyl-pyrrolidin-2-ylmethyl ester as a brown solid (0.97 g, 70.8%). This ester was dissolved in 5 mL conc. HCl and stirred for 3 hrs. to effect cyclisation. At the end of 3 hrs, the reaction mixture was basified with solid Na$_2$CO$_3$ to pH 10. The aqueous layer was extracted with chloroform (3×25 mL) and washed with water (10 mL) and brine (10 mL). The organic layer was dried over anhydrous Na$_2$SO$_4$, concentrated under reduced pressure and dried over vacuum. The residue was purified by column chromatography with 3% methanol in chloroform and 0.1% ammonia as eluent to yield the compound, (+)-trans-2-(2-chloro-4-pyrrolidin-1-yl-phenyl)-8-(2-hydroxymethyl-1-methyl-pyrrolidin-3-yl)-5,7-dimethoxy-chromen-4-one as a brown solid.
Yield: 0.4 g (46.5%);

$^1$H NMR (CDCl$_3$, 300 MHz): δ 7.62 (d, 1H), 6.58 (m, 2H), 6.50 (m, 1H), 6.42 (s, 1H), 4.24 (m, 1H), 3.99 (s, 3H), 3.96 (s, 3H), 3.68 (m, 1H), 3.48 (m, 1H), 3.32 (m, 5H), 2.88 (m, 1H), 2.77 (m, 1H), 2.53 (s, 3H), 2.05 (m, 6H);
MS (ES+): 499 (M+1).

Example 57

(+)-trans-2-(2-Chloro-4-pyrrolidin-1-yl-phenyl)-5,7-dihydroxy-8-(2-hydroxy methyl-1-methylpyrrolidin-3-yl)-chromen-4-one A mixture of the compound of example (56)(0.4 g, 0.8 mmol), pyridine hydrochloride (0.4 g, 3.46 mmol) and a catalytic amount of quinoline was heated at 180° C. for a period of 2.5 hrs. The reaction mixture was diluted with methanol (50 mL) and basified with solid Na$_2$CO$_3$ to pH 10. The reaction mixture was filtered, and washed with methanol. The organic layer was concentrated and the residue purified by column chromatography using 0.1% ammonia and 3% methanol in chloroform as eluent to yield the compound, (+)-trans-2-(2-chloro-4-pyrrolidin-1-yl-phenyl)-5,7-dihydroxy-8-(2-hydroxymethyl-1-methylpyrrolidin-3-yl)-chromen-4-one as a yellow solid.
Yield: 23 mg (6.6%);
$^1$H NMR (CDCl$_3$, 300 MHz): δ 12.82 (s, 1H), 7.47 (d, 1H), 6.62 (d, 1H), 6.52 (dd, 1H), 6.45 (s, 1H), 6.30 (s, 1H), 4.2 (m, 1H), 3.88 (m, 2H), 3.34 (m, 5H), 2.96 (m, 1H), 2.68 (s, 3H), 2.40 (m, 1H), 2.09 (m, 6H);
MS (ES+): 471 (M+1).

Example 58

(+)-trans-2-(2-Chloro-4-pyrrolidin-1-yl-phenyl)-5,7-dihydroxy-8-(2-hydroxy methyl-1-methylpyrrolidin-3-yl)-chromen-4-one hydrochloride The compound of example (57) (23 mg, 0.049 mmol) was suspended in methanol (2 mL) and treated with ethereal HCl and the organic solvent evaporated to obtain the salt, (+)-trans-2-(2-chloro-4-pyrrolidin-1-yl-phenyl)-5,7-dihydroxy-8-(2-hydroxymethyl-1-methylpyrrolidin-3-yl)-chromen-4-one hydrochloride.
Yield: 23 mg (92.8%);
$^1$H NMR (CD$_3$OD, 300 MHz): δ 7.66 (d, 1H), 6.69 (d, 1H), 6.62 (dd, 1H), 6.54 (s, 1H), 6.36 (s, 1H), 4.32 (m, 1H), 3.90 (m, 2H), 3.71 (m, 1H), 3.57 (m, 1H), 3.61 (m, 1H), 3.37 (m, 4H), 3.06 (s, 3H), 2.54 (m, 1H), 2.29 (m, 1H)), 2.06 (m, 4H);
MS (ES−): 505 (M−1).

Example 59

(+)-trans-2-Chloro-4-isopropylaminobenzoic acid 2-(2-acetoxymethyl-1-methyl pyrrolidin-3-yl)-6-acetyl-3,5-dimethoxyphenyl ester 2-Chloro-4-isopropylaminobenzoic acid (1.0 g, 4.6 mmol), thionyl chloride (0.38 mL, 5.1 mmol), N-methylpyrrolidin-2-one (0.1 mL) and dichloromethane (20 mL) were stirred together at room temperature for 12 hrs. To this solution, the compound of example (6)(0.91 g, 2.5 mmol) was added and the mixture cooled to 0 to 5° C. After cooling, triethylamine (1.7 mL, 12 mmol) was added and the reaction allowed to warm to room temperature and stirred for 4 hrs. The reaction mixture was filtered to remove precipitated triethylamine hydrochloride and the organic layer concentrated under reduced pressure to get the title compound as a solid which was utilized as such for further reaction without purification.

Yield: 0.95 g (67%); MS (ES+): 547 (M+1).

Example 60

(+)-trans-2-(2-Chloro-4-isopropylaminophenyl)-8-(2-hydroxymethyl-1-methyl pyrrolidin-3-yl)-5,7-dimethoxy-chromen-4-one To a solution of n-BuLi (1.6 M in hexane, 2.22 mL, 3.56 mmol) in THF (10 mL), maintained at 0° C. under nitrogen atmosphere, hexamethyldisilazane (0.74 mL, 3.56 mmol) was added dropwise and stirred for 15 min. To this, a solution of the compound of example (59)(0.95 g, 1.78 mmol) in THF (5 mL) was added drop wise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8-9. The aqueous layer was extracted with chloroform (3×50 mL). The organic layer was washed with water (25 mL), brine (25 mL) and dried over anhydrous $Na_2SO_4$. The organic layer was concentrated under reduced pressure and dried under vacuum to yield acetic acid 3-{3-[3-(2-chloro-4-isopropylamino-phenyl)-3-oxo-propionyl]-2-hydroxy-4,6-dimethoxy-phenyl}-1-methyl-pyrrolidin-2-ylmethyl ester as a brown solid (0.95 g). This ester was dissolved in conc. HCl (5 mL) and stirred for 3 hrs. to effect cyclisation. At the end of 3 hrs, the reaction mixture was basified with solid $NaHCO_3$ to pH 8-9. The aqueous layer was extracted with chloroform (3×25 mL) and washed with water (10 mL) and brine (10 mL). The organic layer was dried over anhydrous $Na_2SO_4$, concentrated under reduced pressure and dried over vacuum to yield the compound, (+)-trans-2-(2-chloro-4-isopropylaminophenyl)-8-(2-hydroxy methyl-1-methylpyrrolidin-3-yl)-5,7-dimethoxy-chromen-4-one, as a brown solid which was taken ahead without further purification.

Yield: 0.7 g (92.5%)

Example 61

(+)-trans-2-(2-Chloro-4-isopropylaminophenyl)-5,7-dihydroxy-8-(2-hydroxy methyl-1-methyl-pyrrolidin-3-yl)-chromen-4-one A mixture of the compound of example (60)(0.7 g, 1.4 mmol), pyridine hydrochloride (0.7 g, 6 mmol) and a catalytic amount of quinoline was heated at 180° C. for a period of 2.5 hrs. The reaction mixture was diluted with methanol (25 mL) and basified with solid $Na_2CO_3$ to pH 10. The reaction mixture was filtered, and washed with methanol. The organic layer was concentrated and the residue purified by column chromatography using 0.1% ammonia and 3%) methanol in chloroform as eluent to yield the compound, (+)-trans-2-(2-chloro-4-isopropylamino-phenyl)-5,7-dihydroxy-8-(2-hydroxymethyl-1-methylpyrrolidin-3-yl)-chromen-4-one, as a yellow solid.

Yield: 20 mg (3%);

$^1$H NMR ($CDCl_3$, 300 MHz): δ 7.38 (d, 1H), 6.63 (d, 1H), 6.51 (dd, 1H), 6.39 (s, 1H), 6.27 (s, 1H), 4.15 (m, 1H), 3.94 (m, 2H), 3.67 (m, 1H), 3.27 (m, 1H), 2.9 (m, 2H), 2.65 (s, 3H), 2.43 (m, 2H), 1.25 (d, 6H);

MS (ES+): 459 (M+1).

Example 62

(+)-trans-2-(2-Chloro-4-isopropylaminophenyl)-5,7-dihydroxy-8-(2-hydroxy methyl-1-methylpyrrolidin-3-yl)-chromen-4-one hydrochloride The compound of example (61) (20 mg, 0.043 mmol) suspended in methanol (2 mL) and treated with ethereal HCl and the organic solvent evaporated to yield the salt, (+)-trans-2-(2-chloro-4-isopropylaminophenyl)-5,7-dihydroxy-8-(2-hydroxymethyl-1-methylpyrrolidin-3-yl)-chromen-4-one hydrochloride.

Yield: 20 mg (95%);

$^1$H NMR ($CD_3OD$, 300 MHz): δ 7.72 (d, 1H), 7.04 (d, 1H), 6.92 (dd, 1H), 6.58 (s, 1H), 6.37 (s, 1H), 4.35 (m, 1H), 3.95 (m, 1H), 3.8 (m, 1H), 3.75 (m, 2H), 3.65 (dd, 1H), 3.40 (m, 1H), 3.0 (s, 3H), 2.53 (m, 1H), 2.32 (m, 1H), 1.29 (d, 6H);

MS (ES−): 493 (M−1).

Example 63

(+)-trans-2,4-Dibromobenzoic acid 2-(2-acetoxymethyl-1-methylpyrrolidin-3-yl)-6-acetyl-3,5-dimethoxyphenyl ester A mixture of the compound of example (6)(0.84 g, 2.3 mmol), 2,4-dibromobenzoic acid (0.8 g, 2.8 mmol), DCC (0.98 g, 4.7 mmol) and DMAP (0.3 g, 2.3 mmol) were dissolved in dichloromethane (25 mL) and stirred at room temperature for 12 hrs. The reaction mixture is cooled to 0° C., the precipitated dicyclohexylurea was filtered and the organic layer concentrated and the residue purified by column chromatography with 1% methanol in chloroform and 0.1% ammonia as eluent to give the compound, (+)-trans-2,4-dibromo benzoic acid 2-(2-acetoxymethyl-1-methylpyrrolidin-3-yl)-6-acetyl-3,5-dimethoxyphenyl ester.

Yield: 1.14 g (78%);

$^1$H NMR ($CDCl_3$, 300 MHz): δ 8.19 (s, 1H), 7.55 (m, 2H), 6.44 (s, 1H), 4.2 (m, 2H), 3.91 (s, 6H), 3.60 (m, 1H), 3.18 (m, 1H), 2.84 (m, 1H), 2.60 (s, 3H), 2.48 (s, 3H), 2.13 (m, 1H), 1.94 (m, 2H), 1.80 (s, 3H);

MS (ES+): 614 (M+1).

Example 64

(+)-trans-2-(2,4-Dibromophenyl)-8-(2-hydroxymethyl-1-methylpyrrolidin-3-yl)-5,7-dimethoxy-chromen-4-one To a solution of n-BuLi (15% in hexane, 2.38 mL, 5.6 mmol) in THF (10 mL), maintained at 0° C. under nitrogen atmosphere, hexamethyldisilazane (1.67 mL, 8 mmol) was added dropwise and stirred for 15 min. To this, a solution of the compound of example (63)(1.14 g, 1.8 mmol) in THF (10 mL) was added drop wise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8 to 9. The aqueous layer was extracted with chloroform (3×25 mL). The organic layer was washed with water (25 mL), brine (25 mL) and dried over anhydrous $Na_2SO_4$. The organic layer was concentrated under reduced pressure and dried under vacuum to yield acetic acid 3-{3-[3-(2,4-dibromophenyl)-3-oxopropionyl]-2-hydroxy-4,6-dimethoxyphenyl}-1-methyl pyrrolidin-2-ylmethyl ester as a brown solid (1.2 g). This ester was dissolved in conc. HCl (10 mL) and stirred for 3 hrs. to effect cyclisation. At the end of 3 hrs, the reaction mixture was basified with solid NaHCO$_3$ to pH 10. The aqueous layer was extracted with chloroform (25×3 mL) and washed with water (25 mL) and brine (25 mL). The organic layer was dried over anhydrous Na$_2$SO$_4$, concentrated under reduced pressure and dried over vacuum. The residue was purified by column chromatography with 3% methanol in chloroform and 0.1% ammonia as eluent to yield the compound, (+)-trans-2-(2,4-dibromophenyl)-8-(2-hydroxymethyl-1-methylpyrrolidin-3-yl)-5,7-dimethoxy-chromen-4-one. as a yellow solid.

Yield: 0.6 g (58%);

$^1$H NMR (CDCl$_3$, 300 MHz): δ 7.81 (s, 1H), 7.59 (d, 1H), 7.51 (dd, 1H), 6.48 (s, 1H), 6.44 (s, 1H), 4.21 (m, 1H), 4.03 (s, 3H), 4.01 (s, 3H), 3.73 (m, 1H), 3.50 (m, 1H), 3.33 (m, 1H), 2.99 (m, 1H), 2.66 (m, 1H), 2.50 (s, 3H), 2.15 (m, 2H);

MS (ES+): 554 (M+1).

Example 65

(+)-trans-2-(2,4-Dibromophenyl)-5,7-dihydroxy-8-(2-hydroxymethyl-1-methyl pyrrolidin-3-yl)-chromen-4-one A mixture of the compound of example (64) (0.6 g, 1.08 mmol), pyridine hydrochloride (0.6 g, 5.19 mmol) and a catalytic amount of quinoline was heated at 180° C. for a period of 2.5 hrs. The reaction mixture was diluted with methanol (50 mL) and basified with solid Na$_2$CO$_3$ to pH 10. The reaction mixture was filtered, and washed with methanol. The organic layer was concentrated and the residue purified by column chromatography using 0.1% ammonia and % methanol in chloroform as eluent to yield the title compound as a yellow solid.

Yield: 0.2 g (22%); MS (ES+): 526 (M+1).

Example 66

(+)-trans-2-(2,4-Dibromophenyl)-5,7-dihydroxy-8-(2-hydroxymethyl-1-methyl pyrrolidin-3-yl)-chromen-4-one hydrochloride The compound of example (65) (25 mg, 0.047 mmol) suspended in methanol (2 mL) and treated with ethereal HCl and the organic solvent evaporated to get the salt, (+)-trans-2-(2,4-dibromophenyl)-5,7-dihydroxy-8-(2-hydroxymethyl-1-methylpyrrolidin-3-yl)-chromen-4-one hydrochloride.

Yield: 25 mg (93.5%);

$^1$H NMR (CD$_3$OD, 300 MHz): δ 7.95 (m, 1H), 7.73 (m, 2H), 6.52 (s, 1H), 6.38 (s, 1H), 3.90 (m, 1H), 3.85 (m, 2H), 3.60 (m, 2H), 3.4 (m, 1H), 2.97 (s, 3H), 2.53 (m, 1H), 2.28 (m, 1H);

MS (ES−): 560 (M−1)$^+$

Example 67

(+)-trans-2-Bromo-4-chlorobenzoic acid 2-(2-acetoxymethyl-1-methyl-pyrrolidin-3-yl)-6-acetyl-3,5-dimethoxyphenyl ester A mixture of the compound of example (6)(1.12 g, 3.2 mmol), 2-bromo-4-chlorobenzoic acid (0.9 g, 3.8 mmol), DCC (1.32 g, 6.4 mmol) and DMAP (0.4 g, 3.2 mmol) were dissolved in dichloromethane (25 mL) and stirred at room temperature for 12 hrs. The reaction mixture was cooled to 0° C., the precipitated dicyclohexylurea was filtered and the organic layer concentrated and the residue was purified by column chromatography with 1% methanol in chloroform and 0.1% ammonia as eluent to yield the title compound, (+)-trans-2-bromo-4-chloro-benzoic acid 2-(2-acetoxymethyl-1-methyl-pyrrolidin-3-yl)-6-acetyl-3,5-dimethoxy-phenyl ester.

Yield: 0.6 g (33%);

MS (ES+): 569 (M+1).

Example 68

(+)-trans-2-(2-Bromo-4-chlorophenyl)-8-(2-hydroxymethyl-1-methylpyrrolidin-3-yl)-5,7-dimethoxy-chromen-4-one To a solution of n-BuLi (15% in hexane, 0.9 mL, 2 mmol) in THF (10 mL), maintained at 0° C. under nitrogen atmosphere, hexamethyldisilazane (0.44 mL, 2 mmol) was added dropwise and stirred for 15 min. To this, a solution of the compound of example (67) (0.6 g, 1 mmol) in THF (10 mL) was added dropwise, maintaining the temperature at 0° C. After the addition, the reaction was allowed to warm to room temperature and stirred for 2.5 hrs. The reaction mixture was acidified with dilute HCl, and basified with 10% sodium bicarbonate to pH 8 to 9. The aqueous layer was extracted with chloroform (3×25 mL). The organic layer was washed with water (25 mL), brine (25 mL) and dried over anhydrous Na$_2$SO$_4$. The organic layer was concentrated under reduced pressure and dried under vacuum to yield acetic acid 3-{3-[3-(2-bromo-4-chlorophenyl)-3-oxo propionyl]-2-hydroxy-4,6-dimethoxyphenyl}-1-methyl-pyrrolidin-2-ylmethyl ester as a brown solid (1.2 g). This ester was dissolved in conc. HCl (10 mL) and stirred for 3 hrs. to effect cyclisation. At the end of 3 hrs, the reaction mixture was basified with solid NaHCO$_3$ to pH 8 to 9. The aqueous layer was extracted with chloroform (25×3 mL) and washed with water (25 mL) and brine (25 mL). The organic layer was dried over anhydrous Na$_2$SO$_4$, concentrated under reduced pressure and dried under vacuum. The residue was purified by column chromatography with 3% methanol in chloroform and 0.1% ammonia as eluent to yield the compound, (+)-trans-2-(2-bromo-4-chloro phenyl)-8-(2-hydroxymethyl-1-methylpyrrolidin-3-yl)-5,7-dimethoxy-chromen-4-one as a yellow solid.

Yield: 0.3 g (53.6%);

MS (ES+): 509 (M+1).

Example 69

(+)-trans-2-(2-Bromo-4-chlorophenyl)-5,7-dihydroxy-8-(2-hydroxymethyl-1-methylpyrrolidin-3-yl)-chromen-4-one A mixture of the compound of example (68)(0.3 g, 0.59 mmol), pyridine hydrochloride (0.3 g, 2.6 mmol) and a catalytic amount of quinoline was heated at 180° C. for a period of 2.5 hrs. The reaction mixture was diluted with methanol (25 mL) and basified with solid Na$_2$CO$_3$ to pH 10. The reaction mixture was filtered, and washed with methanol. The organic layer was concentrated and the residue purified by column chromatography using 0.1% ammonia and 3% methanol in chloroform as eluent to yield the compound, (+)-trans-2-(2-bromo-4-chlorophenyl)-5,7-dihydroxy-8-(2-hydroxymethyl-1-methyl pyrrolidin-3-yl)-chromen-4-one, as a yellow solid.

Yield: 0.04 g (14%);

MS (ES+): 481 (M+1).

Example 70

(+)-trans-2-(2-Bromo-4-chlorophenyl)-5,7-dihydroxy-8-(2-hydroxymethyl-1-methylpyrrolidin-3-yl)-chromen-4-one hydrochloride The compound of example (69) (34 mg, 0.07 mmol) was suspended in methanol (2 mL) and treated with ethereal HCl and the organic solvent evaporated to get the salt, (+)-trans-2-(2-bromo-4-chlorophenyl)-5,7-dihydroxy-8-(2-hydroxymethyl-1-methylpyrrolidin-3-yl)-chromen-4-one hydrochloride.

Yield: 34 mg (93%);

$^1$HNMR (CD$_3$OD, 300 MHz): δ 7.98 (m, 1H), 7.8 (m, 2H), 6.5 (s, 1H), 6.37 (s, 1H), 4.17 (m, 1H), 3.88 (m, 2H), 3.59 (m, 2H), 3.43 (m, 1H), 3.00 (s, 3H), 2.49 (m, 1H), 2.28 (m, 1H);

MS (ES−): 515 (M−1).

Example 71

(±)-trans-8-(2-Hydroxymethyl-1-methylpyrrolidin-3-yl)-5,7-dimethoxy-2-(2-methoxyphenyl)-chromen-4-one To a suspension of 50% sodium hydride in mineral oil (1.39 g, 29.1 mmol) in N,N-dimethylformamide (60 mL) maintained under nitrogen atmosphere and cooled to 0° C., (±)-trans-1-[2-hydroxy-3-(2-hydroxymethyl-1-methyl-pyrrolidin-3-yl)-4,6-dimethoxyphenyl]-ethanone (3 g, 9.7 mmol) was added portionwise and stirred for 15 mins. At the end of 15 mins., 2-methoxy methylbenzoate (4.8 g, 29 mmol) was added dropwise and the reaction stirred at 0° C. for 1 hr. Excess sodium hydride was destroyed by careful addition of methanol. The reaction mixture was acidified with dilute HCl, and basified with 10% sodium bicarbonate to pH 9. The reaction mixture was concentrated under reduced pressure and dried under vacuum to yield 1-[2-hydroxy-3-(2-hydroxymethyl-1-methylpyrrolidin-3-yl)-4,6-dimethoxyphenyl]-3-(2-methoxyphenyl)-propane-1,3-dione as an oil (1.4 g). This β-diketone was dissolved in conc. HCl (50 mL) and stirred for 3 hrs. to effect cyclisation. At the end of 3 hrs, the reaction mixture was basified with solid NaHCO$_3$ to pH 10. The aqueous layer was extracted with chloroform (50×3 mL) and washed with water (25 mL) and brine (25 mL). The organic layer was dried over anhydrous Na$_2$SO$_4$, concentrated under reduced pressure and dried over vacuum. The residue was purified by column chromatography with 3% methanol in chloroform and 0.1% ammonia as eluent to yield the compound, (±)-trans-8-(2-hydroxymethyl-1-methylpyrrolidin-3-yl)-5,7-dimethoxy-2-(2-methoxyphenyl)-chromen-4-one.

Yield: 1.4 g (34%);

$^1$H NMR (CDCl$_3$, 300 MHz): δ 7.97 (d, 1H), 7.44 (t, 1H), 7.09 (t, 1H), 7.01 (d, 1H), 6.91 (s, 1H), 6.43 (s, 1H), 4.27 (m, 1H), 4.00 (s, 3H), 3.96 (s, 3H), 3.90 (s, 3H), 3.70 (dd, 1H), 3.42 (d, 1H), 3.23 (m, 1H), 2.72 (m, 2H), 2.41 (s, 3H), 2.08 (m, 2H);

MS (ES+): 426 (M+1).

Example 72

(±)-trans-5,7-Dihydroxy-8-(2-hydroxymethyl-1-methylpyrrolidin-3-yl)-2-(2-hydroxyphenyl)-chromen-4-one (Compound-1)

(±)-trans-5,7-Dihydroxy-8-(2-hydroxymethyl-1-methylpyrrolidin-3-yl)-2-(2-methoxyphenyl)-chromen-4-one (Compound-2)

(±)-trans-5-Hydroxy-8-(2-hydroxymethyl-1-methylpyrrolidin-3-yl)-7-methoxy-2-(2-methoxyphenyl)-chromen-4-one (Compound-3)

A mixture of the compound of example (71)(70 mg, 0.165 mmol), pyridine hydrochloride (700 mg, 6.09 mmol) was heated at 180° C. for a period of 2.5 hrs. The reaction mixture was diluted with methanol (50 mL) and basified with solid Na$_2$CO$_3$ to pH 10. The reaction mixture was filtered, and washed with methanol. The organic layer was concentrated and the residue purified by column chromatography using 0.1% ammonia and 3% methanol in chloroform as eluent to yield the compounds, (±)-trans-5,7-dihydroxy-8-(2-hydroxymethyl-1-methylpyrrolidin-3-yl)-2-(2-hydroxyphenyl)-chromen-4-one (Compound-1), (±)-trans-5,7-dihydroxy-8-(2-hydroxymethyl-1-methylpyrrolidin-3-yl)-2-(2-methoxyphenyl)-chromen-4-one (Compound-2), and (±)-trans-5-hydroxy-8-(2-hydroxymethyl-1-methylpyrrolidin-3-yl)-7-methoxy-2-(2-methoxyphenyl)-chromen-4-one (Compound-3).

(Compound-1): Yield: 17 mg (27%);

$^1$H NMR (CDCl$_3$, 300 MHz): δ 7.90 (dd, 1H), 7.36 (m, 1H), 7.00 (s, 1H), 6.96 (m, 2H), 6.18 (s, 1H), 4.20 (m, 1H), 3.79 (dd, 1H), 3.65 (dd, 1h), 3.55 (m, 1h), 3.45 (m, 2H), 2.81 (s, 3H), 2.34 (m, 2H);

MS (ES+): 384 (M+1).

(Compound-2): Yield: 20 mg (30%);

$^1$H NMR (CDCl$_3$, 300 MHz): δ12.77 (s, 1H), 7.82 (dd, 1H), 7.44 (m, 1H), 7.05 (m, 2H), 6.88 (s, 1H), 6.27 (s, 1H), 4.20 (m, 1H), 3.95 (m, 1H), 3.91 (s, 3H), 3.80 (m, 1H), 3.30 (m, 2H), 2.84 (m, 1H), 2.67 (s, 3H), 2.50 (m, 1H), 2.12 (m, 1H);

MS (ES+): 398 (M+1).

(Compound-3): Yield: 12 mg (18%);

$^1$HNMR (CDCl$_3$, 300 MHz): δ 13.12 (s, 1H), 8.03 (m, 1H), 7.48 (m, 1H), 7.11 (m, 1H), 7.02 (m, 1H), 6.99 (s, 1H), 6.42 (s, 1H), 4.21 (m, 1H), 3.93 (s, 3H), 3.91 (s, 3H), 3.58 (m, 2H), 3.11 (m, 1H), 2.70 (m, 2H), 2.39 (s, 3H), 2.05 (m, 2H);

MS (ES+): 412 (M+1).

Example 73

(±)-trans-5,7-Dihydroxy-8-(2-hydroxymethyl-1-methylpyrrolidin-3-yl)-2-(2-hydroxyphenyl)-chromen-4-one hydrochloride The compound-1 of example 72 (15 mg, 0.039 mmol) was suspended in methanol (2 mL) and treated with ethereal HCl and the organic solvent evaporated to get the salt, (±)-trans-5,7-dihydroxy-8-(2-hydroxymethyl-1-methylpyrrolidin-3-yl)-2-(2-hydroxyphenyl)-chromen-4-one hydrochloride.

Yield: 14 mg (85%);

$^1$H NMR (CD$_3$OD, 300 MHz): δ 7.97 (dd, 1H), 7.38 (m, 1H), 7.11 (s, 1H), 7.00 (m, 2H), 6.34 (s, 1H), 4.42 (m, 1H), 3.90 (m, 2H), 3.79 (m, 1H), 3.63 (dd, 1H), 3.49 (m, 1H), 3.01 (s, 3H), 2.58 (m, 1H), 2.36 (m, 1H);

MS (ES+): 420 (M+1)$^+$

Example 74

(+) Acetic acid 3-[2-(2-chlorophenyl)-5,7-dihydroxy-4-oxo-4H-chromen-8-yl]-1-methylpyrrolidin-2-ylmethyl ester The compound of example (9) (2 g, 5 mmol) was stirred in dry dichloromethane (40 mL) with acetic anhydride (2.50 mL, 26.4 mmol) and catalytic amount of dimethylaminopyridine at 25° C. After 1 h. saturated sodium carbonate solution (30 mL) was added to the reaction mixture and stirred for 15 min. The organic layer was separated and aqueous layer was extracted with CHCl$_3$ (3×50 mL). The combined organic layer was concentrated and product obtained was purified using a silica gel column and 3% methanol in CHCl$_3$+1% liquor NH$_3$ as eluent to obtain the compound, (+) acetic acid 3-[2-(2-chlorophenyl)-5,7-dihydroxy-4-oxo-4H-chromen-8-yl]-1-methylpyrrolidin-2-ylmethyl ester Yield: 1.3 g (60%);

IR (KBr): 3421, 3069, 2953, 1742, 1659 cm$^{-1}$;

$^1$H NMR (CDCl$_3$, 300 MHz): δ 12.60 (s, 1H), 7.54 (m, 2H), 7.45 (m, 2H), 6.44 (s, 1H), 6.31 (s, 1H), 4.30 (m, 1H), 4.20 (m, 1H), 4.02 (m, 1H), 3.42 (t, 1H), 3.32 (t, 1H), 2.77 (m, 1H), 2.62 (s, 3H), 2.43 (m, 1H), 2.00 (m, 1H), 1.90 (s, 3H).

Example 75

(+) Acetic acid 3-[2-(2-chlorophenyl)-5,7-dihydroxy-4-oxo-4H-chromen-8-yl]-1-methylpyrrolidin-2-ylmethyl ester hydrochloride Compound of example (74) (0.2 g, 0.38 mmol) was suspended in IPA (5 mL) and 3.5% HCl (25 mL) was added. The suspension was heated to get a clear solution. The solution was cooled and solid filtered to obtain the title compound, (+) acetic acid 3-[2-(2-chlorophenyl)-5,7-dihydroxy-4-oxo-4H-chromen-8-yl]-1-methylpyrrolidin-2-ylmethyl ester hydrochloride Yield: 1.00 g (93%); MS (ES+): m/z 444 (M+1), free base.

Example 76

(+)-trans-Acetic acid 8-(2-acetoxymethylpyrrolidin-3-yl)-2-(2-chlorophenyl)-5-hydroxy-4-oxo-4H-chromen-7-yl ester A solution of the compound of example (10) (10 g, 22 mmol) in pyridine (100 mL) was cooled to 0° C. Acetyl chloride (5.7 mL, 80 mmol) was added dropwise and the reaction mixture was warmed to room temperature followed by heating at reflux for 12 hrs. The mixture was concentrated under reduced pressure and the residue purified by column chromatography using 5% methanol in chloroform as the eluent to give the title compound, (+)-trans-acetic acid 8-(2-acetoxymethylpyrrolidin-3-yl)-2-(2-chlorophenyl)-5-hydroxy-4-oxo-4H-chromen-7-yl ester.

Yield: 5 g (45%);

$^1$H NMR (CDCl$_3$, 300 MHz): δ 7.54 (d, 1H), 7.44 (m, 3H), 6.53 (s, 1H), 6.44 (s, 1H), 4.35 (m, 1H), 4.17 (m, 2H), 3.48 (m, 1H), 3.35 (m, 1H), 2.79 (m, 1H), 2.62 (s, 3H), 2.44 (m, 1H), 2.42 (s, 3H), 1.92 (m, 1H), 2.0 (s, 3H);

MS (ES+): m/z 486 (M+1).

Example 77

(+)-trans-Benzoic acid 8-(2-benzoyloxymethylpyrrolidin-3-yl)-2-(2-chloro phenyl)-5-hydroxy-4-oxo-4H-chromen-7-yl ester A solution of the compound of example (10)(0.5 g, 1.1 mmol) in pyridine (3 mL) was cooled to 0° C. Benzoyl chloride (1 mL, 8.62 mmol) was added dropwise and the reaction mixture was warmed to room temperature followed by heating at reflux for 12 hrs. The mixture was concentrated under reduced pressure and the residue purified by column chromatography using 5% methanol in chloroform as the eluent to give the compound, (+)-trans-benzoic acid 8-(2-benzoyloxymethylpyrrolidin-3-yl)-2-(2-chlorophenyl)-5-hydroxy-4-oxo-4H-chromen-7-yl ester.

Yield: 0.2 g (28%);

$^1$H NMR (CDCl$_3$, 300 MHz): δ 8.25 (m, 1H), 8.09 (m, 1H), 7.91 (m, 1H), 7.50 (m, 11H), 6.68 (s, 1H), 6.34 (s, 1H), 4.55 (m, 2H), 4.32 (dd, 1H), 3.69 (m, 1H), 3.40 (m, 1H), 2.90 (m, 1H), 2.72 (s, 3H), 2.58 (m, 1H), 2.12 (m, 1H);

MS (ES+): m/z 610 (M+1).

Example 78

(+)-trans-Benzoic acid 8-(2-benzoyloxymethylpyrrolidin-3-yl)-2-(2-chloro phenyl)-5-hydroxy-4-oxo-4H-chromen-7-yl ester hydrochloride The compound of example (77) (0.2 g, 0.328 mmol) was suspended in methanol (2 mL) and treated with ethereal HCl and the organic solvent evaporated to get the salt, (+)-trans-benzoic acid 8-(2-benzoyloxymethyl pyrrolidin-3-yl)-2-(2-chlorophenyl)-5-hydroxy-4-oxo-4H-chromen-7-yl ester hydrochloride.

Yield: 0.2 g (94.5%);

$^1$H NMR (CD$_3$OD, 300 MHz): δ 8.2 (m, 1H), 8.02 (m, 1H), 7.81 (m, 1H), 7.49 (m, 11H), 6.85 (s, 1H), 6.29 (s, 1H), 4.69 (m, 1H), 4.5 (m, 3H), 3.89 (m, 1H), 3.62 (m, 1H), 3.12 (s, 3H), 2.74 (m, 1H), 2.48 (m, 1H);

MS (ES+): m/z 610 (M+1), free base.

Example 79

(+)-trans-Octanoic acid 2-(2-chlorophenyl)-5-hydroxy-8-(1-methyl-2-octanoyloxymethylpyrrolidin-3-yl)-4-oxo-4H-chromen-7-yl ester A solution of the compound (10)(0.5 g, 1.2 mmol) in pyridine (3 mL) was cooled to 0° C. Octanoyl chloride, prepared by refluxing octanoic acid (0.41 mL, 3.12 mmol) in thionyl chloride (1 mL) for 30 mins. followed by evaporation to dryness, was added dropwise and the reaction mixture warmed to room temperature followed by heating at reflux for 12 hrs. The mixture was concentrated under reduced pressure and the residue purified by column chromatography using 5% methanol in chloroform as the eluent to give the title compound.

Yield: 0.2 g (30.5%); $^1$H NMR (CDCl$_3$, 300 MHz): δ 12.60 (s, 1H), 7.55 (m, 4H), 6.44 (s, 1H), 6.31 (s, 1H), 4.31 (m, 1H), 4.18 (m, 1H), 4.03 (m, 1H), 3.42 (m, 1H), 3.32 (m, 1H), 2.76 (m, 1H), 2.62 (s, 3H), 2.45 (m, 1H), 2.34 (t, 2H), 2.17 (m, 2H), 1.95 (m, 1H), 1.63 (m, 2H), 1.48 (m, 2H), 1.27 (m, 16H), 0.86 (m, 6H).

Example 80

(+)-trans-Acetic acid 3-[2-(2-chlorophenyl)-5-hydroxy-7-methoxy-4-oxo-4H-chromen-8-yl]-1-methylpyrrolidin-2-ylmethyl ester To a solution of the compound of example (8)(2.0 g, 4.65 mmol) and dimethylaminopyridine (10 mg) in dichloromethane (20 mL), acetic anhydride (0.48 mL, 5.07 mmol) was added dropwise and the reaction mixture stirred for 15 mins. At the end of 15 mins., the reaction mixture was diluted with chloroform (20 mL), the organic layer washed with 10% $NaHCO_3$, water (10 mL) and brine (10 mL). The organic layer was dried over anhydrous $Na_2SO_4$ and concentrated under reduced pressure. The residue was dissolved in dichloromethane (20 mL), followed by the addition of borontrifluoride diethyl etherate (1.72 mL, 13.9 mmol) and dimethyl sulfide (1.1 mL, 14 mmol) and stirred at room temperature for 1 hr. The reaction mixture was poured into ice, basified with 10% $Na_2CO_3$ and extracted with chloroform (2×50 mL). The organic layers were combined, washed with water (10 mL), brine (10 mL), dried over anhydrous $Na_2SO_4$ and concentrated under reduced pressure. The residue was purified by column chromatography using 20% petroleum ether in chloroform and 0.1% ammonia as eluent to give the compound, (+)-trans-acetic acid 3-[2-(2-chlorophenyl)-5-hydroxy-7-methoxy-4-oxo-4H-chromen-8-yl]-1-methylpyrrolidin-2-ylmethyl ester Yield: 1.22 g (58%);
$^1H$ NMR ($CDCl_3$, 300 MHz): δ 12.88 (s, 1H), 7.50 (m, 4H), 6.47 (s, 1H), 6.44 (s, 1H), 4.04 (m, 2H), 3.95 (m, 1H), 3.90 (s, 3H), 3.13 (m, 1H), 2.74 (m, 1H), 2.50 (m, 1H), 2.36 (s, 3H), 2.13 (m, 1H), 1.95 (m, 1H), 1.72 (s, 3H);
MS (ES+): m/z 458 (M+1).

Example 81

(+)-trans-2-(2-Chlorophenyl)-5-hydroxy-8-(2-hydroxymethyl-1-methylpyrrolidin-3-yl)-7-methoxy-chromen-4-one Method A Compound of example (80) (1.4 g, 3.0 mmol) was dissolved in methanol (6 mL) to which 2% aqueous NaOH solution (6 mL) was added and the mixture was heated with stirring at 50-60° C. for 1 hr. At the end of this period, the mixture was acidified with dilute HCl followed by basification with 10% $Na_2CO_3$ solution to pH 9. The mixture was extracted with EtOAc (3×25 mL) and the organic layers washed with water (10 mL), brine (10 mL), dried over anhydrous $Na_2SO_4$, concentrated under reduced pressure and the residue purified by column chromatography using 1% isopropanol in chloroform and 0.1% ammonia as eluent to give the compound, (+)-trans-2-(2-chlorophenyl)-5-hydroxy-8-(2-hydroxymethyl-1-methylpyrrolidin-3-yl)-7-methoxy-chromen-4-one.

Yield: 1.2 g (97%);
IR (KBr): 3446, 1656, 1608 $cm^{-1}$;
$^1H$ NMR ($CDCl_3$, 300 MHz): δ 12.90 (s, 1H), 7.74 (m, 1H), 7.48 (m, 3H), 6.57 (s, 1H), 6.44 (s, 1H), 4.11 (m, 1H), 3.91 (s, 3H), 3.63 (dd, 1H), 3.36 (d, 1H), 3.14 (m, 1H), 2.72 (m, 1H), 2.55 (m, 1H), 2.33 (s, 3H), 2.01 (m, 2H);
MS (ES+): m/z 416 (M+1)$^+$.

Method B

Compound of example (8) (0.1 g, 0.23 mmol) was treated with HBr (5 mL, 47%) at 100° C. for 3.5 h. Reaction mixture was poured over ice, basified with $Na_2CO_3$ solution (10%, 40 mL), extracted with ethyl acetate and concentrated. Product obtained was purified by column chromatography and 5% methanol+1% liquor $NH_3$ in $CHCl_3$ as eluant to obtain the title compound.

Yield: 0.085 g (84%); $^1H$ NMR ($CDCl_3$, 300 MHz): δ 12.90 (s, 1H), 7.74 (m, 1H), 7.48 (m, 3H), 6.57 (s, 1H), 6.44 (s, 1H), 4.11 (m, 1H), 3.91 (s, 3H), 3.63 (dd, 1H), 3.36 (d, 1H), 3.14 (m, 1H), 2.72 (m, 1H), 2.55 (m, 1H), 2.33 (s, 3H), 2.01 (m, 2H); MS (ES+): m/z 416 (M+1).

Example 82

(+)-trans-2-(2-Chlorophenyl)-5-hydroxy-8-(2-hydroxymethyl-1-methylpyrrolidin-3-yl)-7-methoxy-chromen-4-one hydrochloride The compound of example (81) (50 mg, 0.11 mol) was suspended in methanol (2 mL) and treated with ethereal HCl and the organic solvent evaporated to get the salt, (+)-trans-2-(2-chlorophenyl)-5-hydroxy-8-(2-hydroxymethyl-1-methyl pyrrolidin-3-yl)-7-methoxy-chromen-4-one hydrochloride.

Yield: 53 mg (100%);
IR (KBr): 3297, 1663, 1608, 1581 $cm^{-1}$;
$^1H$ NMR ($CD_3OD$, 300 MHz): δ 8.12 (d, 1H), 7.91 (m, 3H), 6.96 (s, 1H), 6.89 (s, 1H), 4.62 (m, 1H), 4.34 (s, 3H), 4.17 (m, 2H), 4.03 (m, 1H), 3.90 (m, 1H), 3.71 (m, 1H), 3.31 (s, 3H), 2.75 (m, 1H), 2.62 (m, 1H); MS (ES+): m/z 416 (M−36.5);
$[\alpha]_D^{25}$: +15.32° (c=0.27, methanol).

Example 83

(+)-trans-2-(2-Chlorophenyl)-5-hydroxy-8-(2-hydroxymethyl-1-methylpyrrolidin-3-yl)-7-methoxy-chromen-4-one gluconate The compound of example (81) (50 mg, 0.12 mmol) was suspended in methanol (1 mL) and water (1 mL) and stirred. To this, gluconic acid (24 mg, 0.12 mmol) was added, stirred and the solution evaporated to dryness to get the salt, (+)-trans-2-(2-chlorophenyl)-5-hydroxy-8-(2-hydroxymethyl-1-methyl pyrrolidin-3-yl)-7-methoxy-chromen-4-one gluconate Yield: 74 mg (100%); IR (KBr): 3445, 1654, 1609 $cm^{-1}$;
$^1H$ NMR ($CD_3OD$, 300 MHz): δ 7.80 (d, 1H), 7.59 (m, 3H), 6.64 (s, 1H), 6.57 (s, 1H), 4.27 (m, 1H), 4.07 (m, 2H), 4.02 (s, 3H), 3.76 (m, 7H), 2.92 (s, 3H), 2.33 (m, 2H); $[\alpha]_D^{25}$: +18.17° (c=0.73, methanol)

Example 84

(+)-trans-Acetic acid-3-[2-(2-chlorophenyl)-5,7-dihydroxy-4-oxo-4H-chromen-8-yl]-1-methylpyrrolidin-2-ylmethyl ester To a solution of the compound of example (10)(1 g, 2.28 mmol) and triethylamine (1.6 mL, 11.4 mmol) in methylene chloride (10 mL), acetic anhydride (0.7 mL, 7.4 mmol) was added and stirred for 30 min. at ambient temperature. The reaction mixture was quenched with saturated sodium carbonate solution (10 mL) and stirred for 30 min. The organic layer was separated, washed with aqueous sodium carbonate (10 mL), water (10 mL), dried over anhydrous sodium sulphate and evaporated under reduced pressure to get the compound, (+)-trans-acetic acid-3-[2-(2-chlorophenyl)-5,7-dihydroxy-4-oxo-4H-chromen-8-yl]-1-methylpyrrolidin-2-ylmethyl ester, which was used as such without further purification.

Yield: 1.1 g (99%);
$^1$H NMR (CDCl$_3$, 300 MHz) δ 12.59 (s, 1H), 7.45 (m, 4H), 6.44 (s, 1H), 6.31 (s, 1H), 4.32 (m, 1H), 4.19 (m, 1H), 4.05 (m, 1H), 3.44 (m, 1H), 3.30 (m, 1H), 2.79 (m, 1H), 2.62 (s, 3H), 2.42 (m, 1H), 1.98 (m, 1H), 1.92 (s, 3H);
MS (ES+): 444 (M+1).

Example 85

(+)-trans-Acetic acid 3-[2-(2-chlorophenyl)-5-hydroxy-7-(2-methoxyethoxy methoxy)-4-oxo-4H-chromen-8-yl]-1-methylpyrrolidin-2-ylmethyl ester The compound of example (84)((1.11 g, 2.50 mmol) was dissolved in dry DMF (15 mL) under nitrogen atmosphere and cooled to 0° C. Sodium hydride (50%, 0.14 g, 2.9 mmol) was added and the mixture stirred for 30 min. A solution of 2-methoxyethoxymethyl chloride (0.33 mL, 2.9 mmol) in dry DMF was added dropwise and the reaction maintained at 10° C. overnight. The reaction was poured into ice water (10 mL), acidified with acetic acid to pH 5, basified with aqueous Na$_2$CO$_3$ (pH 9), and extracted with ethyl acetate (2×25 mL). The organic layer was separated, washed with water (15 mL), brine (15 mL), dried over anhydrous sodium sulphate and concentrated under reduced pressure to dryness to yield the compound, (+)-trans-acetic acid-3-[2-(2-chlorophenyl)-5-hydroxy-7-(2-methoxyethoxymethoxy)-4-oxo-4H-chromen-8-yl]-1-methyl pyrrolidin-2-ylmethyl ester Yield: 1.1 g (92%);
$^1$H NMR (CDCl$_3$, 300 MHz): δ 12.78 (s, 1H), 7.56 (m, 4H), 6.68 (s, 1H), 6.48 (s, 1H), 5.39 (s, 2H), 4.20 (m, 2H), 4.05 (m, 1H), 3.83 (m, 2H), 3.58 (m, 2H), 3.38 (s, 3H), 2.56 (m, 3H), 2.16 (s, 3H), 1.81 (s, 3H), 1.62 (m, 2H);
MS (ES+): 532 (M+1).

Example 86

(+)-trans-2-(2-Chlorophenyl)-5-hydroxy-8-(2-hydroxymethyl)-1-methyl pyrrolidin-3-yl)-7-(2-methoxyethoxymethoxy)-chromen-4-one The compound of example (85) (1.1 g, 2.07 mmol) was dissolved in 15 mL of 1% solution of sodium hydroxide in 1:1 methanol-water mixture and stirred at room temperature for 1 hr. At the end of 1 hr, the reaction mixture was diluted with ice water, acidified with acetic acid (pH 5), basified with aqueous Na$_2$CO$_3$ (pH 9), and extracted with ethyl acetate (2×25 mL). The organic layer was separated, washed with water (15 mL), brine (15 mL), dried over anhydrous sodium sulphate and concentrated under reduced pressure. The residue purified by column chromatography using 1% isopropanol in chloroform and 0.1% ammonia as the eluent to give the title compound, (+)-trans-2-(2-chloro phenyl)-5-hydroxy-8-(2-hydroxymethyl)-1-methylpyrrolidin-3-yl)-7-(2-methoxy ethoxymethoxy)-chromen-4-one.

Yield: 0.43 g (38.7%);
$^1$H NMR (CDCl$_3$, 300 MHz): δ 12.84 (s, 1H), 7.73 (d, 1H), 7.50 (m, 3H), 6.62 (s, 1H), 6.57 (s, 1H), 5.41 (s, 2H), 4.30 (q, 1H), 3.85 (m, 3H), 3.59 (m, 4H), 3.37 (m, 1H), 3.35 (s, 3H), 2.96 (m, 1H), 2.72 (s, 3H), 2.39 (m, 1H), 2.24 (m, 1H);
MS (ES+): 490 (M+1).

Example 87

(+)-trans-2-(2-Chlorophenyl)-5-hydroxy-8-(2-hydroxymethyl)-1-methylpyrrolidin-3-yl)-7-(2-methoxyethoxymethoxy)-chromen-4-one gluconate To a solution of the compound of example (86)(0.55 g, 1.12 mmol) in methanol (5 mL), (+)-gluconic acid (0.22 g, 1.12 mmol) was added and the mixture stirred at room temperature for 30 min. The solvent was removed under reduced pressure to get the salt, (+)-trans-2-(2-chlorophenyl)-5-hydroxy-8-(2-hydroxymethyl)-1-methylpyrrolidin-3-yl)-7-(2-methoxyethoxymethoxy)-chromen-4-one gluconate.

Yield: 0.77 g (100%);
IR (KBr): 3385, 1656, 1606 cm$^{-1}$;
$^1$H NMR (CD$_3$OD, 300 MHz): δ 7.62 (d, 1H), 7.54 (m, 3H), 6.74 (s, 1H), 6.57 (s, 1H), 5.49 (s, 2H), 4.29 (m, 1H), 4.07 (s, 2H), 3.76 (m, 13H), 3.34 (s, 3H), 2.90 (s, 3H), 2.38 (m, 2H);
MS (ES+): 490 (M+1)$^+$, free base;
$[\alpha]_D^{25}$: +15.33° (c=0.6, methanol).

Example 88

(+)-trans-2-(2-Chlorophenyl)-8-(2-hydroxymethyl-1-methylpyrrolidin-3-yl)-5,7-dimethoxy-chromen-4-one hydrochloride The compound of example (8) (50 mg, 0.116 mmol) was suspended in methanol (2 mL) and stirred. To this ethereal HCl was added and the solution stirred and evaporated to get the salt, (+)-trans-2-(2-chlorophenyl)-8-(2-hydroxymethyl-1-methylpyrrolidin-3-yl)-5,7-dimethoxy-chromen-4-one hydrochloride.

Yield: 50 mg (93%);
IR (KBr): 3421, 1647, 1599, 1471 cm$^{-1}$;
$^1$H NMR (CD$_3$OD, 300 MHz): δ 7.95 (d, 1H), 7.56 (m, 3H), 6.76 (s, 1H), 6.47 (s, 1H), 4.36 (m, 1H), 3.95 (s, 3H), 3.85 (s, 3H), 3.82 (m, 2H), 3.68 (m, 2H), 3.35 (m, 1H), 2.99 (s, 3H), 2.36 (m, 2H);
MS (ES+): m/z 430 (M+1), free base;
$[\alpha]_D^{25}$: +3.76° (c=0.28, methanol)

Example 89

(+)-trans-2-(2-Chlorophenyl)-8-(2-hydroxymethyl-1-methylpyrrolidin-3-yl)-5,7-dimethoxy-chromen-4-one citrate The compound of example (8) (50 mg, 0.116 mmol) was suspended in methanol (2 mL) and stirred. To this citric acid (23 mg, 0.12 mmol) was added and the solution stirred and evaporated to get the title salt, (+)-trans-2-(2-chloro-phenyl)-8-(2-hydroxymethyl-1-methyl-pyrrolidin-3-yl)-5,7-dimethoxy-chromen-4-one citrate.

Yield: 73 mg (100%);
$^1$H NMR (CD$_3$OD, 300 MHz): δ 7.79 (d, 1H), 7.57 (m, 3H), 6.77 (s, 1H), 6.48 (s, 1H), 4.35 (m, 1H), 4.10 (s, 3H), 4.02 (s, 3H), 3.98 (m, 2H), 3.69 (m, 2H), 3.31 (m, 1H), 3.01 (s, 3H), 2.76 (m, 4H), 2.29 (m, 2H).

Example 90

(+)-trans-2-(2-Chlorophenyl)-8-(2-hydroxymethyl-1-methylpyrrolidin-3-yl)-5,7-dimethoxy-chromen-4-one tartarate The compound of example (8) (50 mg, 0.116 mmol) was suspended in methanol (2 mL) and stirred. To this tartaric acid (17 mg, 0.113 mmol) was added and the solution stirred and evaporated to get the salt, (+)-trans-2-(2-chlorophenyl)-8-(2-hydroxymethyl-1-methylpyrrolidin-3-yl)-5,7-dimethoxy-chromen-4-one tartarate.

Yield: 7 mg (100%);
$^1$H NMR (CD$_3$OD, 300 MHz): δ 7.76 (d, 1H), 7.57 (m, 3H), 6.75 (s, 1H), 6.46 (s, 1H), 4.22 (m, 1H), 4.08 (s, 3H), 4.01 (s, 3H), 3.77 (m, 1H), 3.49 (m, 3H), 3.31 (m, 2H), 3.05 (m, 1H), 2.78 (s, 3H), 2.26 (m, 2H);
MS (ES+): m/z 430 (M), free base;
$[α]_D^{25}$: +5.35° (c=0.21, methanol)

Example 91

(+)-trans-2-(2-Chlorophenyl)-8-(2-hydroxymethyl-1-methylpyrrolidin-3-yl)-5,7-dimethoxy-chromen-4-one glutamate The compound of example (8) (50 mg, 0.116 mmol) was suspended in methanol (2 mL) and stirred. To this glutamic acid (17 mg, 0.115 mmol) was added and the solution stirred and evaporated to get the salt, (+)-trans-2-(2-chlorophenyl)-8-(2-hydroxymethyl-1-methylpyrrolidin-3-yl)-5,7-dimethoxy-chromen-4-one glutamate.

Yield: 67 mg (100%);
$^1$H NMR (CD$_3$OD, 300 MHz): δ 7.79 (d, 1H), 7.57 (m, 3H), 6.77 (s, 1H), 6.48 (s, 1H), 4.41 (m, 4H), 4.10 (s, 3H), 4.02 (s, 3H), 3.98 (m, 1H), 3.85 (m, 2H), 3.69 (m, 4H), 2.95 (s, 3H), 2.38 (m, 2H).

Example 92

(+)-trans-2-(2-Chlorophenyl)-8-(2-hydroxymethyl-1-methylpyrrolidin-3-yl)-5,7-dimethoxy-chromen-4-one maleate The compound of example (8) (50 mg, 0.116 mmol) was suspended in methanol (2 mL) and stirred. To this maleic acid (14 mg, 0.116 mmol) was added and the solution stirred and evaporated to get the salt, (+)-trans-2-(2-chlorophenyl)-8-(2-hydroxymethyl-1-methylpyrrolidin-3-yl)-5,7-dimethoxy-chromen-4-one maleate.

Yield: 5 mg (78%);
$^1$H NMR (CD$_3$OD, 300 MHz): δ 7.78 (d, 1H), 7.62 (d, 1H), 7.56 (t, 1H), 7.49 (t, 1H), 6.76 (s, 1H), 6.47 (s, 1H), 6.25 (s, 2H), 4.35 (m, 1H), 4.09 (s, 3H), 4.01 (s, 3H), 3.83 (m, 2H), 3.69 (m, 1H), 3.56 (m, 1H), 3.32 (m, 1H), 2.95 (s, 3H), 2.41 (m, 1H), 2.28 (m, 1H).

Example 93

(+)-trans-2-(2-Chlorophenyl)-8-(2-hydroxymethyl-1-methylpyrrolidin-3-yl)-5,7-dimethoxy-chromen-4-one nitrate The compound of example (8) (50 mg, 0.116 mmol) was suspended in methanol (2 mL) and stirred. To this nitric acid (7.1 mg, 0.113 mmol) was added and the solution stirred and evaporated to get the title salt, (+)-trans-2-(2-chlorophenyl)-8-(2-hydroxymethyl-1-methylpyrrolidin-3-yl)-5,7-dimethoxy-chromen-4-one nitrate.

Yield: 57 mg (99%);
$^1$H NMR (CD$_3$OD, 300 MHz): δ 7.79 (d, 1H), 7.53 (m, 3H), 6.77 (s, 1H), 6.49 (s, 1H), 4.35 (m, 1H), 4.10 (s, 3H), 4.02 (s, 3H), 3.86 (m, 2H), 3.74 (m, 1H), 3.57 (m, 1H), 3.39 (m, 1H), 2.96 (s, 3H), 2.43 (m, 1H), 2.32 (m, 1H).

Example 94

(+)-trans-2-(2-Chlorophenyl)-8-(2-hydroxymethyl-1-methylpyrrolidin-3-yl)-5,7-dimethoxy-chromen-4-one acetate The compound of example (8) (50 mg, 0.116 mmol) was suspended in methanol (2 mL) and stirred. To this acetic acid (7 mg, 0.11 mmol) was added and the solution stirred and evaporated to get the title salt, (+)-trans-2-(2-chlorophenyl)-8-(2-hydroxymethyl-1-methylpyrrolidin-3-yl)-5,7-dimethoxy-chromen-4-one acetate.

Yield: 56 mg (100%);
$^1$H NMR (CD$_3$OD, 300 MHz): δ 7.79 (d, 1H), 7.57 (m, 3H), 6.77 (s, 1H), 6.48 (s, 1H), 4.35 (m, 1H), 4.17 (s, 3H), 4.02 (s, 3H), 3.98 (m, 1H), 3.86 (m, 2H), 3.70 (m, 1H), 3.57 (m, 1H), 3.31 (s, 3H), 2.95 (s, 3H), 2.43 (m, 1H), 2.30 (m, 1H);
$[α]_D^{25}$: +2.85° (c=0.14, methanol).

Example 95

(+)-trans-2-(2-Chlorophenyl)-8-(2-hydroxymethyl-1-methylpyrrolidin-3-yl)-5,7-dimethoxy-chromen-4-one gluconate The compound of example (8) (50 mg, 0.116 mmol) was suspended in methanol (2 mL) and stirred. To this gluconic acid (21 mg, 0.11 mmol) was added and the solution stirred and evaporated to get the salt, (+)-trans-2-(2-chlorophenyl)-8-(2-hydroxymethyl-1-methylpyrrolidin-3-yl)-5,7-dimethoxy-chromen-4-one gluconate.

Yield: 71 mg (100%);
IR (KBr): 3445, 1648, 1560 cm$^{-1}$;
$^1$H NMR (CD$_3$OD, 300 MHz): δ 7.61 (d, 1H), 7.59 (m, 3H), 6.76 (s, 1H), 6.73 (s, 1H), 4.75 (m, 2H), 4.09 (s, 3H), 3.82 (s, 3H), 3.70 (m, 9H), 3.30 (m, 1H), 2.89 (s, 3H), 2.34 (m, 2H);
MS (ES+): m/z 430 (M+1), free base;
$[α]_D^{25}$: +2.85° (c=0.14, methanol);
Analysis: (C$_{29}$H$_{36}$ClN$_{12}$O.H$_2$O) C, 54.31 (54.08), H, 5.90 (5.94), N, 2.49 (2.17), Cl, 5.62 (5.34), Water 3.30 (2.79).

Example 96

(+)-trans-2-(2-Chlorophenyl)-5,7-dihydroxy-8-(2-hydroxymethyl-1-methyl pyrrolidin-3-yl)-chromen-4-one hydrochloride (This compound is the (−)-trans enantiomer of the compound illustrated in example 10. The (−)-trans enantiomer was prepared to compare its activity with that of its corresponding (+)-trans enantiomer.)

(A) (+)-trans-[1-Methyl-3-(2,4,6-trimethoxyphenyl)-pyrrolidin-2-yl]-methanol (+)-DBTA (112.7 g, 314.0 mmol) was added to compound of example (4) (88.5 g, 314 mmol) followed by addition of methanol (600 mL). The mixture was refluxed for 10 min., stirred slowly at room temperature for 3 h., the crystallised salt was filtered and dried.

Yield: 80.5 g (40%); $[α]_D^{25}$=+82.11° (c=0.7, methanol). The salt was stirred with 10% aqueous solution of Na$_2$CO$_3$ (255 mL) and EtOAc (200×3 mL) to obtain the free base in the EtOAc layer. The EtOAc layer was concentrated to obtain the title compound.

Yield: 30 g (98.5%); [α]$_D^{25}$=+20.2° (c=0.7, methanol); $^1$H NMR (CDCl$_3$, 300 MHz): δ 6.13 (s, 2H), 3.90 (m, 1H), 3.79 (s, 9H), 3.57 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

(B) (+)-trans-Acetic acid 3-(3-acetyl-2-hydroxy-4,6-dimethoxyphenyl)-1-methyl pyrrolidin-2-yl methyl ester BF$_3$-etherate (36.8 g, 259 mmol) was added dropwise, with stirring, at 0° C., under N$_2$ atmosphere to a solution of compound of example ((96-(A))(14.6 g, 51.9 mmol) in acetic anhydride (24.26 mL, 26.2 g, 256 mmol). The reaction mixture was stirred at room temperature for 2 h. It was poured over crushed ice (1 kg), basified using a saturated aqueous Na$_2$CO$_3$ solution and extracted using EtOAc (3×200 mL). The organic extract was washed with brine, dried (anhydrous Na$_2$SO$_4$) and concentrated to get title compound.

Yield: 17.8 g (98%); $^1$H NMR (CDCl$_3$, 300 MHz): δ 6.1 (s, 1H), 4.22 (m, 2H), 4.15 (m, 1H), 3.94 (s, 3H), 3.92 (s, 3H), 3.82 (m, 1H), 3.57 (m, 1H), 3.23 (m, 1H), 2.85 (s, 3H), 2.64 (s, 3H), 2.28 (m, 2H), 2.01 (s, 3H).

(C) (+)-trans-1-[2-Hydroxy-3-(2-hydroxymethyl-1-methylpyrrolidin-3-yl)-4,6-dimethoxyphenyl]ethanone To a solution of compound of example (96-(B)) (17.8 g, 50.7 mmol) in methanol (40 mL) was added with stirring, at room temperature, a 10% aqueous NaOH (40 mL) solution. The temperature of the reaction mixture was raised to 50° C. for 45 min. It was cooled to room temperature, acidified using conc. HCl and concentrated to remove methanol. It was basified using a saturated aqueous Na$_2$CO$_3$ solution. The precipitated title compound was filtered, washed with water and dried.

Yield: 10.2 g (65%); mp: 173-174° C.; [α]$_D^{25}$=+4.12° (c=0.7, methanol);
$^1$H NMR (CDCl$_3$, 300 MHz): δ 5.96 (s, 1H), 3.93 (m, 1H), 3.91 (s 3H), 3.90 (s, 3H), 3.58 (dd, 1H), 3.42 (d, 1H), 3.23 (m, 1H), 2.80 (m, 1H), 2.63 (s, 3H), 2.62 (m, 1H), 2.40 (s, 3H), 2.00 (m, 2H); MS (ES+): m/z 310 (M+1).

(D) (−)-trans-2-(2-Chlorophenyl)-8-(2-hydroxymethyl-1-methylpyrrolidin-3-yl)-5,7-dimethoxy-chromen-4-one Sodium hydride (50%, 0.54 g, 11.25 mmol) was added in portions to a solution of compound of example (96-(C)) (0.7 g, 2.2 mmol) in dry DMF (15 mL) at 0° C., under nitrogen atmosphere and with stirring. After 10 min., methyl 2-chlorobenzoate (1.15 g, 6.75 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated Na$_2$CO$_3$ (pH 10) and extracted using CHCl$_3$ (3×200 mL). The organic layer was dried (anhydrous Na$_2$SO$_4$) and concentrated. To the residue, conc. HCl (25 mL) was added and stirred at room temperature for 2 h. The reaction mixture was poured over crushed ice (300 g) and made basic using a saturated aqueous Na$_2$CO$_3$ solution. The mixture was extracted using CHCl$_3$ (3×200 mL). The organic extract was washed with water, dried (anhydrous Na$_2$SO$_4$) and concentrated to obtain the title compound.

Yield: 0.625 g (65%); mp: 95-97° C.; IR (KBr): 3431, 1648, 1598, 1571 cm$^{-1}$; [α]$_D^{25}$=−4.95° (c=0.7, methanol); $^1$H NMR (CDCl$_3$, 300 MHz): δ 7.70 (dd, 1H), 7.68 (m, 3H), 6.50 (s, 1H), 6.44 (s, 1H), 4.20 (m, 1H), 4.00 (s, 3H), 3.96 (s, 3H), 3.66 (dd, 1H), 3.37 (d, 1H), 3.15 (m, 1H), 2.77 (d, 1H), 2.54 (m, 1H), 2.33 (s, 3H), 2.05 (m, 2H); MS (ES+): m/z 430 (M+1).

(E) (−)-trans-2-(2-Chlorophenyl)-5,7-dihydroxy-8-(2-hydroxymethyl-1-methyl pyrrolidin-3-yl)-chromen-4-one Molten pyridine hydrochloride (2 g, 17.3 mmol) was added to compound of example (96-(D)) (0.2 g, 0.46 mmol) and heated at 180° C. for 1.5 h. The reaction mixture was cooled to 25° C., diluted with MeOH (10 mL) and basified using Na$_2$CO$_3$ to pH 10. The mixture was filtered and the organic layer was concentrated. The residue was suspended in water (5 mL), stirred for 30 min., filtered and dried to obtain the title compound.

Yield: 0.125 g (67.6%); mp: 228-230° C.; IR (KBr): 3422, 3135, 1664, 1623, 1559 cm$^{-1}$; MS (ES+): m/z 402 (M+1); Analysis: C$_{21}$H$_{20}$ClNO$_5$.0.5H$_2$O C, 61.81 (61.33); H, 4.62 (5.00); N, 3.75 (3.33); Cl, 8.47 (8.45).

(F) (−)-trans-2-(2-Chlorophenyl)-5,7-dihydroxy-8-(2-hydroxymethyl-1-methyl pyrrolidin-3-yl)-chromen-4-one hydrochloride The Compound of example (96-(E)) (4.09 g, 10.18 mmol) was suspended in IPA (5 mL) and 3.5% HCl (25 mL) was added. The suspension was heated to get a clear solution. The solution was cooled and solid filtered to obtain the title compound.

Yield: 4.47 g (99%); mp: 180-184° C.; [α]$_D^{25}$=−20.2° (c=0.4, methanol);
$^1$H NMR (CD$_3$OD, 300 MHz): δ 7.80 (d, 1H), 7.60 (m, 3H), 6.54 (s, 1H), 6.37 (s, 1H), 4.23 (m, 1H), 3.89 (m, 2H), 3.63 (m, 1H), 3.59 (dd, 1H), 3.38 (m, 1H), 2.97 (s, 3H), 2.51 (m, 1H), 2.30 (m, 1H); MS (ES+): m/z 402 (M−36.5); Analysis: C$_{21}$H$_{21}$Cl$_2$NO$_5$C, 57.2 (57.55); H, 4.92 (4.83); N, 2.98 (3.20); Cl, 15.74 (16.18).

Example 97

(−)-trans-2-(2-Chloro-4-nitrophenyl)-5,7-dihydroxy-8-(2-hydroxymethyl-1-methyl pyrrolidin-3-yl)-chromen-4-one hydrochloride (This compound is the (−)-trans enantiomer of the compound illustrated in example 50. The (−)-trans enantiomer was prepared to compare its activity with that of its corresponding (+)-trans enantiomer)

(A). (−)-trans-2-Chloro-4-nitro-benzoic acid 2-(2-acetoxymethyl-1-methyl pyrrolidin-3-yl)-6-acetyl-3,5-dimethoxyphenyl ester 2-Chloro-4-nitrobenzoic acid (3.55 g, 17 mmol) and thionyl chloride (2 mL) were heated together at 85° C. for 3 hrs. Excess thionyl chloride was evaporated under reduced pressure and the residue was dried in vacuum and dissolved in THF (50 mL). This was added dropwise to a solution of the compound of example (96-(B))(4 g, 11 mmol) and triethylamine (15 mL, 108 mmol) in THF (100 mL) maintained at 15-20° C. The reaction mixture was allowed to warm to room temperature and was stirred for 12 hrs. At the end of 12 hrs., the reaction mixture was concentrated to remove THF, acidified with dilute HCl, basified with 10% NaHCO$_3$ solution to pH 10, extracted with EtOAc (3×100 mL), washed with water (50 mL), brine (50 mL) and the organic layer dried over anhydrous $Na_2SO_4$. The organic layer was concentrated under reduced pressure to get the title compound as an oil which was utilized as such for further reaction without purification.

Yield: 1.62 g (25%); $^1$H NMR (CDCl$_3$, 300 MHz): δ 8.35 (d, 1H), 8.25 (m, 2H), 6.45 (s, 1H), 4.10 (m, 1H), 3.94 (s, 6H), 3.59 (m, 1H), 3.17 (m, 1H), 2.70 (m, 1H), 2.49 (s, 3H), 2.46 (m, 2H), 2.35 (s, 3H), 2.17 (m, 1H), 1.95 (m, 1H), 1.83 (s, 3H); MS (ES+): m/z 535 (M+1).

(B). (−)-trans-2-(2-Chloro-4-nitrophenyl)-8-(2-hydroxymethyl-1-methylpyrrolidin-3-yl)-5,7-dimethoxy-chromen-4-one To a solution of n-BuLi (15% in hexane, 2.54 mL, 5.8 mmol) in THF (25 mL), maintained at 0° C. under nitrogen atmosphere, hexamethyldisilazane (1.25 mL, 5.8 mmol) was added dropwise and stirred for 15 min. To this, a solution of (−)-trans-2-chloro-4-nitro-benzoic acid 2-(2-acetoxymethyl-1-methyl-pyrrolidin-3-yl)-6-acetyl-3,5-dimethoxy-phenyl ester (1.6 g, 3 mmol) in THF (25 mL) was added dropwise, maintaining the temperature at 0° C. After the addition, the reaction was allowed to warm to room temperature and stirred for 2.5 hrs. The reaction mixture was acidified with dilute HCl, basified with 10% NaHCO$_3$ solution to pH 8 to 9. The aqueous layer was extracted with chloroform (3×50 mL). The organic layer was washed with water (25 mL), brine (25 mL), dried over anhydrous $Na_2SO_4$. The organic layer was concentrated under reduced pressure and under vacuum to yield acetic acid 3-{3-[3-(2-chloro-4-nitro phenyl)-3-oxopropionyl]-2-hydroxy-4,6-dimethoxyphenyl}-1-methylpyrrolidin-2-ylmethyl ester as a yellow solid (1.6 g). This ester was dissolved in conc. HCl (16 mL) and stirred at room temperature for 3 hrs to effect cyclisation. At the end of 3 hrs, the reaction mixture was basified with solid NaHCO$_3$ to pH 8 to 9. The aqueous layer was extracted with chloroform (3×50 mL) and washed with water (25 mL) and brine (25 mL). The organic layer was dried over anhydrous $Na_2SO_4$, concentrated under reduced pressure and dried over vacuum. The residue was purified by column chromatography with 3% methanol in chloroform and 0.1% ammonia as eluent to yield the title compound as a yellow solid.

Yield: 0.71 g (50%); IR (KBr): 3447, 1648, 1600, 1570 cm$^{-1}$, $^1$H NMR (CDCl$_3$): δ 8.37 (d, 1H), 8.26 (dd, 1H), 8.09 (d, 1H), 6.67 (s, 1H), 6.46 (s, 1H), 4.18 (m, 1H), 4.01 (s, 3H), 3.98 (s, 3H), 3.67 (m, 1H), 3.32 (m, 1H), 3.19 (m, 1H), 2.62 (m, 2H), 2.36 (s, 3H), 2.04 (m, 2H); MS (ES+): m/z 475 (M+1).

(C) (−)-trans-2-(2-Chloro-4-nitrophenyl)-5,7-dihydroxy-8-(2-hydroxymethyl-1-methylpyrrolidin-3-yl)-chromen-4-one A mixture of (−)-trans-2-(2-chloro-4-nitrophenyl)-8-(2-hydroxymethyl-1-methyl pyrrolidin-3-yl)-5,7-dimethoxy-chromen-4-one (0.4 g, 0.8 mmol), pyridine hydrochloride (0.48 g, 4.1 mmol) and a catalytic amount of quinoline was heated at 180° C. for a period of 2 hrs. The reaction mixture was cooled and diluted with methanol (50 mL) and basified with solid $Na_2CO_3$ to pH 10. The reaction mixture was filtered, and washed with methanol. The organic layer was concentrated and the residue purified by column chromatography using 0.1% ammonia and 3% methanol in chloroform as eluent to yield the title compound as a yellow solid.

Yield: 0.24 g (65%); MS (ES+): m/z 447 (M+1).

(D). (−)-trans-2-(2-Chloro-4-nitrophenyl)-5,7-dihydroxy-8-(2-hydroxymethyl-1-methylpyrrolidin-3-yl)-chromen-4-one hydrochloride (−)-trans-2-(2-Chloro-4-nitrophenyl)-5,7-dihydroxy-8-(2-hydroxymethyl-1-methyl pyrrolidin-3-yl)-chromen-4-one (0.2 g, 0.4 mmol) was suspended in methanol (10 mL) and treated with ethereal HCl and the organic solvent evaporated to get the title salt.

Yield: 0.18 g (85%); $^1$H NMR (CD$_3$OD, 300 MHz): δ 8.51 (d, 1H), 8.36 (dd, 1H), 8.09 (d, 1H), 6.69 (s, 1H), 6.41 (s, 1H), 4.25 (m, 1H), 3.91 (m, 2H), 3.73 (m, 1H), 3.70 (m, 1H), 3.63 (m, 1H), 3.00 (s, 3H), 2.55 (m, 1H), 2.32 (m, 1H); MS (ES+): m/z 483 (M+1).

Example 98

(Comparative Example: Prepared as Per the Method Disclosed in Published US Patent Application No. 2004/0106581)

(−)-trans-[1-Methyl-3-(2,4,6-trimethoxyphenyl)-pyrrolidin-2-yl]-methanol

Compound of example 4 (27.3 g, 97.1 mmol), was dissolved in methanol (100 mL) and heated to 70° C. To this hot solution was added (+) DBTA (36.51 g, 101.9 mmol) and the heating was continued for 10 min. It was concentrated to get a solid (63.81 g), which was crystallized using methanol (45 mL) and isopropanol (319 mL). Filtration and an isopropanol wash with subsequent drying afforded the crystalline tartarate salt (13.14 g), $[α]_D^{25}$=+55.34° (c=1.14, methanol). This product was then recrystallized using methanol (10 mL) and isopropanol (40 mL). It was isolated as described above, yield: 9.04 g, $[α]_D^{25}$=+49.67° (c=1.248, methanol). The free base was obtained from this product as follows.

The salt (9 g) was suspended in ethyl acetate (100 mL). To this suspension 5% aqueous NaHCO$_3$ solution (100 mL) was added and the mixture was stirred for 30 minutes. The organic portion was separated and the aqueous portion was further extracted using ethyl acetate (2×50 mL). The organic portions were combined and concentrated to obtain the compound, (−)-trans-[1-Methyl-3-(2,4,6-trimethoxyphenyl)pyrrolidin-2-yl]methanol Yield: 3.6 g (26.3%).

$[α]_D^{25}$=−17.6° (c=1.1, methanol).

$^1$H NMR (CDCl$_3$): δ 6.13 (s, 2H), 3.90 (m, 1H), 3.79 (s, 9H), 3.51 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

MS (ES+): m/z 282 (M+1).

Figure 2:
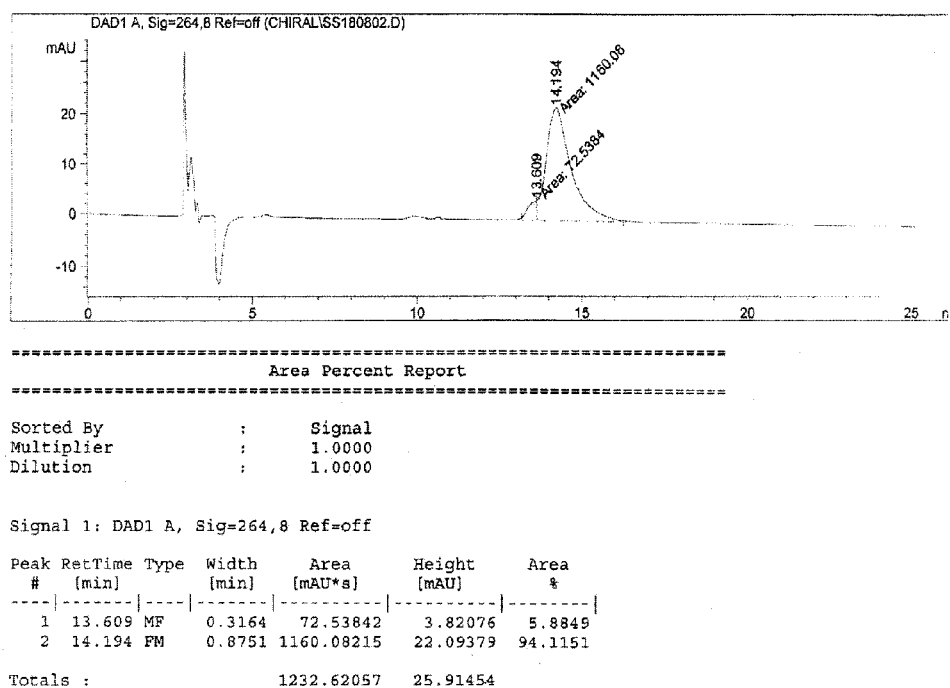
FIG. 2: Chiral HPLC (Chiralcel OD-H (250×4.6 mm) Column) of (−)-trans-[1-methyl-3-(2,4,6-trimethoxyphenyl)-pyrrolidin-2-yl]methanol obtained as described in Example 98 (Prior art method).

This compound was subjected to chiral HPLC. Chiral HPLC was done using column Chiralcel OD-H (250×4.6 mm) and solvent system haxane:ethanol (92:08) with TFA (0.4%). The results are recorded at 264 nm with solvent flow rate of 1 mL/min. As depicted in FIG. 2, the chiral HPLC showed 88.3% e.e of the compound, (−)-trans-[1-Methyl-3-(2,4,6-trimethoxyphenyl)pyrrolidin-2-yl]-methanol.

Biological Testing

The efficacy of the (+)-trans enantiomers of the compounds of formula I in inhibiting the activity of cyclin-dependent kinases can be determined by a number of pharmacological assays well known in the art, such as described below or, for example, in Losiewics, M. D., et al. Biochem. Biophys. Res. Commun., 1994, 201, 589. The kinases, cyclins, and substrates used in the in vitro kinase assay can be proteins isolated from mammalian cells, or alternatively, they can be proteins produced recombinantly. The exemplified pharmacological assays as described herein below have been carried out with the compounds of the present invention and their salts.

CDK4/Cyclin D1 Kinase Assay and CDK2/Cyclin E Kinase Assay

The assays measure phosphorylation of retinoblastoma protein (Rb) by CDK4 or CDK2 upon activation by cyclin D1 or cyclin E, respectively, through the transfer of $(\gamma^{32}P)$-phosphate from $\gamma^{32}P$-ATP in a 96-well filter plate assay.

Materials

CDK4 or CDK2 was co-expressed with cyclin D1 or cyclin E, respectively, by a baculovirus expression system in insect cells. For this, $1 \times 10^7$ Sf9 cells were coinfected with baculoviruses containing human CDK-4 or 2 and cyclin D1 or E genes and after 72 hours cells were lysed in 500 µl of a lysis buffer (50 mM HEPES (pH 7.5), 10 mM $MgCl_2$, 1 mM DTT, 5 µg/ml of aprotinin, 5 µg/ml of leupeptin, 0.1 mM NaF, 0.2 mM phenylmethylsulfonyl fluoride (PMSF), and sodium orthovanadate. Centrifuged lysate was purified on a GST-sepharose column. Purity of the proteins was checked by SDS-PAGE followed by western blots using specific antibodies (Santacruz Biotec, USA) to CDK4 or CDK2.

GST-retinoblastoma (Rb) (aa 776-928) fusion protein is expressed in the bacteria *E. coli* and purified by GSH-Sepharose affinity chromatography. The GST-Rb bound to these beads served as the substrate in the assay.

Readout

Quantitation was by scintillation detection of $(^{32}P)$-GST-Rb in 96-well filter plates using Top Count scintillation 96-well counter (Packard, USA).

Procedure

The CDK4 or CDK2 enzyme assay was run in 96-well format using Millipore ultiscreen filtration plates. All assay steps took place in a single filter plate (Unifilter plates, Packard, USA). The filtration wells were pre-wet with kinase buffer (100 µl/well) and the solution was then removed by the application of vacuum, with the filter plate on a vacuum manifold and the vacuum on. 50 µl of GST-Rb bound to GSH-Sepharose beads in kinase buffer (0.5 µg GST-Rb/50 µl) was added to each well and vacuum was applied to remove the buffer. A further 25 µl of a reaction mix containing ATP (cold+hot) and phosphatase inhibitors diluted in kinase buffer were added to each well, followed by the addition of test compound (4× final concentration in kinase buffer) or kinase buffer (control) in an additional 25 µl volume. Finally 50 µl (100 ng) of human CDK-4/D1 or CDK-2/E enzyme in kinase buffer was added to each well to initiate the reaction. The reaction was incubated for 30 min at 30° C. After the reaction was complete, vacuum was applied and the plate was washed with the wash buffer (TNEN buffer) three times. The filter plate was air-dried and placed in a Multiscreen adapter plate. To each well, 30 µl Packard Microscint-O cocktail was added and the plate was covered with a Top-Seal A film. The plate was counted in a Packard Top Count Scintillation Counter for 10 min. Flavopiridol was used as a standard inhibitor in all the experiments.

The concentration of compound at which 50% of phosphokinase activity of CDK4-cyclin D1 and CDK2-cyclin E was inhibited ($IC_{50}$) was calculated for representative compounds and their pharmaceutically acceptable salts described in the Examples. The results are indicated in Table 1.

TABLE 1

| | $IC_{50}(\mu M)$ | |
|---|---|---|
| Compound(s) | CDK4-CYCLIN D1 | CDK2-CYCLIN E |
| Compound of Example 10 | 0.065 | 2.8 |
| Compound of Example 96-(F) | NA | 21 |
| Compound of Example 50 | 0.045 | 1.7 |
| Compound of Example 97-(D) | 1 | >10 |
| Flavopiridol | 60 | 360 |

In Vitro Cell Proliferation and Cytotoxicity Assays

Exponentially growing cultures of ten human cancerous cell lines (Calu1 lung, A-549 lung, HT-29 colon, HL-60 Promyelocytic Leukemia, PC-3 Prostate, H-460 Lung, MDA-MB-231 Breast, MCF-7 Breast, HeLa Cervix, Colo-205 Colon, H9 Lymphoma (T Cells), U-937 Histiocytic Lymphoma (monocytes) and CaCO-2 Colon) obtained from NCCS, Pune, India were used. The in vitro cell proliferation (NCl, USA protocol) and cytotoxicity assays were carried out using standard procedures viz. $^3$H-Thymidine uptake and MTS assay, respectively (For $^3$H-Thymidine uptake: Cell Biology, A Laboratory Handbook, 1998, Vol 1 Ed Julio E. Celis, and For MTS assay: Promega Protocol, USA, 2000). In the $^3$H-Thymidine uptake assay, cells were harvested after 72 hours onto GF/B unifilter plates (Packard, USA) using a Packard Filtermate Universal harvester and the plates were counted on a Packard TopCount 96-well liquid scintillation counter. The concentration of compound at which 50% of proliferative activity was inhibited ($IC_{50}$) and the degree of toxicity of compound were calculated for representative compounds and their pharmaceutically acceptable salts described in the Examples. The results are indicated in Table 2 below.

TABLE 2

| | Thymidine Assay ($IC_{50} \mu M$) | | | MTS Cytotoxocity ($IC_{50} \mu M$) | | |
|---|---|---|---|---|---|---|
| Compound(s) | Calu1 (Lung) | A-549 (Lung) | HT-29 (Colon) | Calu1 (Lung) | A-549 (Lung) | HT-29 (Colon) |
| Compound of Example 10 | <0.3 | 0.18 | 0.68 | 0.88 | 0.7 | 0.58 |
| Compound of Example 96-(F) | *NA | 10 | 25 M | 16.3 | 16 | 17.9 |
| Compound of Example 50 | <0.3 | 1.2 | 1.5 | 1.4 | 1.2 | 1.1 |
| Compound of Example 97-(D) | ND | *NA | 10 | ND | *NA | *NA |

*No Statistically Significant Inhibition Observed
NA—Not Active
ND—Not Done

The results indicate that the (+)-trans enantiomer of compounds of formula (I) is a more potent inhibitor than its (−)-trans enantiomer. Hence, administration of the (+) trans enantiomer of compounds of formula (I) substantially free of the (−)-trans enantiomer provides a reduction in the required dose of drug.

We claim:

1. An enantiomerically pure compound represented by the following formula (I) or a pharmaceutically acceptable salt thereof:

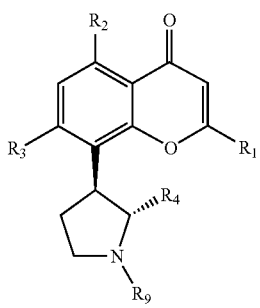

(I)

wherein:
  $R_1$ is 2-chloro-4-trifluoromethylphenyl;
  $R_2$ and $R_3$ are each independently selected from:
    hydroxyl or $OR_8$;
      wherein $R_8$ is substituted or unsubstituted, $C_1$-$C_{10}$-alkyl, $C_1$-$C_4$-alkanoyl, or substituted or unsubstituted aroyl;
  $R_4$ is $CH_2OH$; and
  $R_9$ is hydrogen or $C_1$-$C_4$-alkyl.

2. The enantiomerically pure compound of formula I according to claim 1 or a pharmaceutically acceptable salt thereof selected from:
  (+)-trans-2-(2-Chloro-4-trifluoromethylphenyl)-8-(2-hydroxymethyl-1-methyl-pyrrolidin-3-yl)-5,7-dimethoxy-chromen-4-one;
  (+)-trans-2-(2-Chloro-4-trifluoromethylphenyl)-5,7-dihydroxy-8-(2-hydroxymethyl-1-methylpyrrolidin-3-yl)-chromen-4-one; and
  (+)-trans-2-(2-Chloro-4-trifluoromethylphenyl)-5,7-dihydroxy-8-(2-hydroxymethyl-1-methyl-pyrrolidin-3-yl)-chromen-4-one hydrochloride.

3. A process for the preparation of an enantiomerically pure compound of formula (I) as claimed in claim 1, comprising the steps of:
  (a) treating the enantiomerically pure resolved (−)-trans enantiomer of a compound represented by formula (VIA):

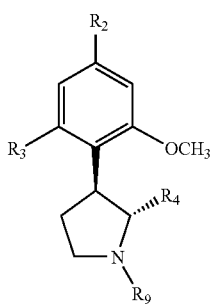

VIA wherein:
  $R_2$ and $R_3$ are each independently selected from:
    halogen, hydroxyl, and $OR_8$;
      wherein $R_8$ is substituted or unsubstituted $C_1$-$C_{10}$-alkyl, $C_1$-$C_4$-alkanoyl, or substituted or unsubstituted aroyl;
  $R_4$ is $C_1$-$C_4$-alkylenehydroxyl; and
  $R_9$ is hydrogen or $C_1$-$C_4$-alkyl;
with acetic anhydride in the presence of a Lewis acid catalyst selected from:
  boron trifluoride, diethyl etherate, zinc chloride, aluminium chloride, and titanium chloride;
to obtain resolved acetylated compound of formula (VIIA):

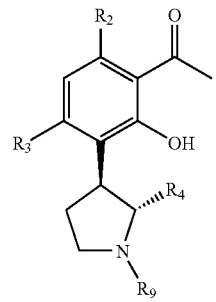

VIIA wherein, $R_2$, $R_3$ and $R_9$ are as defined and $R_4$ is $CH_2OC(O)CH_3$;

(b) reacting the resolved acetylated compound of formula (VIIA) from step (a) with an acid of formula $R_1COOH$ or an acid chloride of formula $R_1COCl$ or an acid anhydride of formula $(R_1CO)_2O$ or an ester of formula $R_1COOCH_3$, wherein $R_1$ is as defined in claim 1, in the presence of a base and a solvent to obtain a compound of formula (VIIIA):

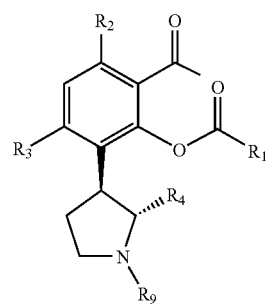

VIIIA wherein $R_1$, $R_2$, $R_3$, and $R_9$ are as defined herein above and $R_4$ is $CH_2OC(O)CH_3$;

(c) treating the resolved compound of formula (VIIIA) with a base selected from:
  lithium hexamethyldisilazide, sodium hexamethyldisilazide, potassium hexamethyldisilazide, sodium hydride, and potassium hydride;
to obtain the corresponding resolved β-diketone compound of formula (IXA):

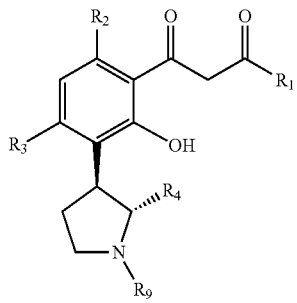

wherein $R_1$, $R_2$, $R_3$ and $R_9$ are as defined herein above and $R_4$ is $CH_2OC(O)CH_3$;

(d) treating the β-diketone compound of formula (M) with an acid to obtain the corresponding resolved cyclized compound of formula (XA):

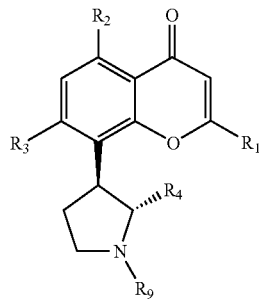

wherein $R_1$, $R_2$, $R_3$ and $R_9$ are as defined herein above, $R_4$ is $CH_2OH$;

(e) treating the resolved compound of formula (XA) with a dealkylating agent selected from:
   pyridine hydrochloride, boron tribromide, boron trifluoride etherate; and
   aluminium trichloride;
to effect dealkylation at a temperature ranging from 120-180° C. to obtain the enantiomerically pure compound of formula (I).

4. A pharmaceutical composition comprising:
a therapeutically effective amount of the enantiomerically pure compound of formula (I) as claimed in claim 1, or a pharmaceutically acceptable salt thereof; and
a pharmaceutically acceptable carrier; and
optionally, an additive.

5. A pharmaceutical composition as claimed in claim 4, further comprising:
   at least one other anti-proliferative agent selected from cytotoxic or anticancer agents.

6. A method for the treatment of cancer in a mammal which comprises:
administering to said mammal a therapeutically effective amount of the enantiomerically pure compound of formula (I) as claimed in claim 1, or a pharmaceutically acceptable salt thereof; wherein the cancer is lung cancer or colon cancer.

7. The method of claim 6;
wherein the enantiomerically pure compound of formula (I), or a pharmaceutically acceptable salt thereof, is administered either sequentially or simultaneously with a therapeutically effective amount of at least one other anti-proliferative agent selected from cytotoxic or anticancer agents.

8. The pharmaceutical composition of claim 4;
wherein the therapeutically effective amount of the enantiomerically pure compound of formula (I) is the compound selected from:
   (+)-trans-2-(2-Chloro-4-trifluoromethylphenyl)-8-(2-hydroxymethyl-1-methyl-pyrrolidin-3-yl)-5,7-dimethoxy-chromen-4-one;
   (+)-trans-2-(2-Chloro-4-trifluoromethylphenyl)-5,7-dihydroxy-8-(2-hydroxymethyl-1-methylpyrrolidin-3-yl)-chromen-4-one; and
   (+)-trans-2-(2-Chloro-4-trifluoromethylphenyl)-5,7-dihydroxy-8-(2-hydroxymethyl-1-methyl-pyrrolidin-3-yl)-chromen-4-one hydrochloride.

9. The method of claim 6;
wherein the therapeutically effective amount of the enantiomerically pure compound of formula (I) is the compound selected from:
   (+)-trans-2-(2-Chloro-4-trifluoromethylphenyl)-8-(2-hydroxymethyl-1-methyl-pyrrolidin-3-yl)-5,7-dimethoxy-chromen-4-one;
   (+)-trans-2-(2-Chloro-4-trifluoromethylphenyl)-5,7-dihydroxy-8-(2-hydroxymethyl-1-methylpyrrolidin-3-yl)-chromen-4-one; and
   (+)-trans-2-(2-Chloro-4-trifluoromethylphenyl)-5,7-dihydroxy-8-(2-hydroxymethyl-1-methyl-pyrrolidin-3-yl)-chromen-4-one hydrochloride.

* * * * *